(12) United States Patent
Brinkmann et al.

(10) Patent No.: US 9,879,095 B2
(45) Date of Patent: *Jan. 30, 2018

(54) BISPECIFIC ANTIBODIES COMPRISING A DISULFIDE STABILIZED-FV FRAGMENT

(71) Applicant: Hoffmann-La Roche Inc., Nutley, NJ (US)

(72) Inventors: Ulrich Brinkmann, Weilheim (DE); Alexander Haas, Munich (DE); Silke Metz, Bad Toelz (DE); Juergen Michael Schanzer, Munich (DE)

(73) Assignee: HOFFMAN-LA ROCHE INC., Nutley, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/773,167

(22) Filed: Feb. 21, 2013

(65) Prior Publication Data

US 2013/0267686 A1 Oct. 10, 2013

Related U.S. Application Data

(63) Continuation of application No. PCT/EP2011/064476, filed on Aug. 23, 2011.

(30) Foreign Application Priority Data

Aug. 24, 2010 (EP) .................... 10173914

(51) Int. Cl.
C07K 16/00 (2006.01)
A61K 39/00 (2006.01)
C07K 16/46 (2006.01)
C07K 16/28 (2006.01)
C07K 16/32 (2006.01)

(52) U.S. Cl.
CPC ............ *C07K 16/468* (2013.01); *C07K 16/00* (2013.01); *C07K 16/2863* (2013.01); *C07K 16/32* (2013.01); *C07K 2317/31* (2013.01); *C07K 2317/56* (2013.01); *C07K 2317/624* (2013.01); *C07K 2317/64* (2013.01); *C07K 2319/00* (2013.01)

(58) Field of Classification Search
CPC .......... C07K 2317/31; C07K 2317/565; C07K 2317/92; C07K 16/2863; C07K 2317/56; C07K 2317/624; C07K 2317/24; C07K 2317/622; C07K 2317/35; A61K 2039/505; A61K 2039/507; A61K 47/48561; A61K 39/39558

See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,120,649 A | 10/1978 | Schechter |
| 4,137,230 A | 1/1979 | Hashimoto et al. |
| 4,150,149 A | 4/1979 | Wolfsen et al. |
| 4,151,042 A | 4/1979 | Higahide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,544 A | 11/1982 | Goldberg |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howley et al. |
| 4,424,219 A | 1/1984 | Hashimoto et al. |
| 4,444,744 A | 4/1984 | Goldberg |
| 4,450,254 A | 5/1984 | Isley et al. |
| 4,560,655 A | 12/1985 | Baker |
| 4,601,978 A | 7/1986 | Karin |
| 4,657,866 A | 4/1987 | Kumar |
| 4,665,077 A | 5/1987 | Stringfellow et al. |
| 4,737,456 A | 4/1988 | Weng et al. |
| 4,767,704 A | 8/1988 | Cleveland |
| 4,816,567 A | 3/1989 | Cabilly et al. |
| 4,927,762 A | 5/1990 | Darfler |

(Continued)

FOREIGN PATENT DOCUMENTS

| | | |
|---|---|---|
| CN | 1173878 A | 2/1998 |
| CN | 1176659 A | 3/1998 |

(Continued)

OTHER PUBLICATIONS

Merchant et al (Nature Biotechnology, 1998, 16:677-681).*
Aggarwal et al. (Jan. 22, 2008). "Fibroblast activation protein peptide substrates identified from human collagen I derived gelatin clevage sites," *Biochemistry* 47(3):1076-1086.
Anonymous. (1997). "Production in yeasts of stable antibody fragments," *Expert Opinion on Therapeutic Patents* 7(2):179-183.

(Continued)

*Primary Examiner* — Julie Wu

(74) *Attorney, Agent, or Firm* — Morrison & Foerster LLP

(57) ABSTRACT

The present invention relates to bispecific antibodies, methods for their production, pharmaceutical compositions containing said antibodies, and uses thereof.

19 Claims, 31 Drawing Sheets

(56) References Cited

U.S. PATENT DOCUMENTS

| | | |
|---|---|---|
| 4,965,199 A | 10/1990 | Capon |
| 4,975,278 A | 12/1990 | Senter et al. |
| 5,053,394 A | 10/1991 | Ellestad et al. |
| 5,114,721 A | 5/1992 | Cohen et al. |
| 5,122,469 A | 6/1992 | Mather et al. |
| 5,143,844 A | 9/1992 | Abrahmsen et al. |
| 5,202,238 A | 4/1993 | Fell, Jr. et al. |
| 5,204,244 A | 4/1993 | Fell et al. |
| 5,208,020 A | 5/1993 | Chari et al. |
| 5,264,365 A | 11/1993 | Georgiou et al. |
| 5,362,852 A | 11/1994 | Geoghegan |
| 5,416,064 A | 5/1995 | Chari et al. |
| 5,500,362 A | 3/1996 | Robinson et al. |
| 5,508,192 A | 4/1996 | Georgiou et al. |
| 5,532,142 A | 7/1996 | Johnston et al. |
| 5,571,894 A | 11/1996 | Wels et al. |
| 5,587,458 A | 12/1996 | King et al. |
| 5,591,828 A | 1/1997 | Bosslet et al. |
| 5,624,821 A | 4/1997 | Winter et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,237 A | 7/1997 | Carter et al. |
| 5,663,149 A | 9/1997 | Pettit et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,113 A | 4/1998 | Lee |
| 5,739,116 A | 4/1998 | Hamann et al. |
| 5,747,654 A | 5/1998 | Pastan et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,798,229 A | 8/1998 | Strittmatter et al. |
| 5,821,333 A | 10/1998 | Carter et al. |
| 5,821,337 A | 10/1998 | Carter et al. |
| 5,824,483 A | 10/1998 | Houston |
| 5,840,523 A | 11/1998 | Simmons et al. |
| 5,869,046 A | 2/1999 | Presta et al. |
| 5,877,296 A | 3/1999 | Hamann et al. |
| 5,932,448 A | 8/1999 | Tso et al. |
| 5,959,083 A | 9/1999 | Bosslet et al. |
| 5,959,177 A | 9/1999 | Hein et al. |
| 6,027,888 A | 2/2000 | Georgiou et al. |
| 6,040,498 A | 3/2000 | Stomp et al. |
| 6,083,715 A | 7/2000 | Georgiou et al. |
| 6,136,564 A | 10/2000 | Kopetzki |
| 6,166,185 A | 12/2000 | Davis et al. |
| 6,171,586 B1 | 1/2001 | Lam et al. |
| 6,194,551 B1 | 2/2001 | Idusogie et al. |
| 6,239,259 B1 | 5/2001 | Davis et al. |
| 6,248,516 B1 | 6/2001 | Winter et al. |
| 6,267,958 B1 | 7/2001 | Andya et al. |
| 6,350,860 B1 | 2/2002 | Buyse et al. |
| 6,417,429 B1 | 7/2002 | Hein et al. |
| 6,420,548 B1 | 7/2002 | Vezina et al. |
| 6,511,663 B1 | 1/2003 | King et al. |
| 6,534,628 B1 | 3/2003 | Nilsson et al. |
| 6,558,672 B1 | 5/2003 | Pastan et al. |
| 6,586,207 B2 | 7/2003 | Tirrell et al. |
| 6,602,684 B1 | 8/2003 | Umana et al. |
| 6,660,843 B1 | 12/2003 | Feige et al. |
| 6,833,441 B2 | 12/2004 | Wang et al. |
| 6,835,809 B1 | 12/2004 | Liu et al. |
| 6,897,044 B1 | 5/2005 | Braslawsky et al. |
| 6,919,426 B2 | 7/2005 | Boone et al. |
| 6,946,292 B2 | 9/2005 | Kanda et al. |
| 6,982,321 B2 | 1/2006 | Winter |
| 7,125,978 B1 | 10/2006 | Vezina et al. |
| 7,129,330 B1 | 10/2006 | Little et al. |
| 7,355,008 B2 | 4/2008 | Stavenhagen et al. |
| 7,381,408 B2 | 6/2008 | Mezo et al. |
| 7,507,796 B2 | 3/2009 | Little et al. |
| 7,642,228 B2 | 1/2010 | Carter et al. |
| 7,651,688 B2 | 1/2010 | Hanai et al. |
| 7,666,622 B2 | 2/2010 | Sharma et al. |
| 7,695,936 B2 | 4/2010 | Carter et al. |
| 7,919,257 B2 | 4/2011 | Hoogenboom et al. |
| 7,942,042 B2 | 5/2011 | Kawakita et al. |
| 8,216,805 B2 | 7/2012 | Carter et al. |
| 8,227,577 B2 | 7/2012 | Klein et al. |
| 8,242,247 B2 | 8/2012 | Klein et al. |
| 8,268,314 B2 | 9/2012 | Baehner et al. |
| 8,304,713 B2 | 11/2012 | Pradel |
| 8,309,300 B2 | 11/2012 | Jununtual et al. |
| 8,796,424 B2 | 8/2014 | Croasdale et al. |
| 8,871,912 B2 | 10/2014 | Davis et al. |
| 2002/0155537 A1 | 10/2002 | Carter et al. |
| 2003/0027751 A1 | 2/2003 | Kovesdi et al. |
| 2003/0124129 A1 | 7/2003 | Oliner |
| 2003/0170230 A1 | 9/2003 | Caterer et al. |
| 2003/0176352 A1 | 9/2003 | Min et al. |
| 2003/0195156 A1 | 10/2003 | Min et al. |
| 2003/0219817 A1 | 11/2003 | Zhu |
| 2003/0229023 A1 | 12/2003 | Oliner et al. |
| 2003/0236193 A1 | 12/2003 | Oliner et al. |
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0214988 A1 | 10/2004 | Tirrell et al. |
| 2004/0220388 A1 | 11/2004 | Metens et al. |
| 2004/0259075 A1 | 12/2004 | Dimitrov et al. |
| 2005/0054048 A1 | 3/2005 | Grasso et al. |
| 2005/0064509 A1 | 3/2005 | Bradbury et al. |
| 2005/0079170 A1 | 4/2005 | Le Gall et al. |
| 2005/0100543 A1 | 5/2005 | Hansen et al. |
| 2005/0123476 A1 | 6/2005 | Bugge et al. |
| 2005/0152894 A1 | 7/2005 | Krummen et al. |
| 2005/0163782 A1 | 7/2005 | Glaser et al. |
| 2005/0169933 A1 | 8/2005 | Steeves et al. |
| 2005/0186208 A1 | 8/2005 | Fyfe et al. |
| 2005/0238649 A1 | 10/2005 | Doronina et al. |
| 2005/0249722 A1 | 11/2005 | Beliard et al. |
| 2005/0260186 A1 | 11/2005 | Bookbinder et al. |
| 2006/0008845 A1 | 1/2006 | Kondejewski et al. |
| 2006/0063921 A1 | 3/2006 | Moulder et al. |
| 2006/0104968 A1 | 5/2006 | Bookbinder et al. |
| 2006/0122370 A1 | 6/2006 | Oliner et al. |
| 2006/0134709 A1 | 6/2006 | Stavenhagen et al. |
| 2006/0160184 A1 | 7/2006 | Hoogenboom et al. |
| 2006/0280747 A1 | 12/2006 | Fuh et al. |
| 2007/0014794 A1 | 1/2007 | Carter et al. |
| 2007/0071675 A1 | 3/2007 | Wu et al. |
| 2007/0071742 A1 | 3/2007 | Fang et al. |
| 2007/0141065 A1 | 6/2007 | Fuh et al. |
| 2007/0178552 A1 | 8/2007 | Arathoon et al. |
| 2007/0269369 A1 | 11/2007 | Gegg et al. |
| 2007/0274985 A1 | 11/2007 | Dubel et al. |
| 2007/0274998 A1 | 11/2007 | Utku |
| 2007/0287170 A1 | 12/2007 | Davis et al. |
| 2008/0063641 A1 | 3/2008 | Huang et al. |
| 2008/0187954 A1 | 8/2008 | Kallmeier et al. |
| 2008/0234183 A1 | 9/2008 | Hallbrink et al. |
| 2009/0023811 A1 | 1/2009 | Biadatti et al. |
| 2009/0060910 A1 | 3/2009 | Johnson |
| 2009/0117105 A1 | 5/2009 | Hu et al. |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0194692 A1 | 8/2009 | Kobaru |
| 2009/0232811 A1 | 9/2009 | Klein et al. |
| 2010/0081796 A1* | 4/2010 | Brinkmann et al. ....... 530/387.3 |
| 2010/0111967 A1 | 5/2010 | Baehner et al. |
| 2010/0254989 A1 | 10/2010 | Bossenmaier et al. |
| 2010/0256338 A1 | 10/2010 | Brinkmann et al. |
| 2010/0256339 A1 | 10/2010 | Bossenmaier et al. |
| 2010/0256340 A1 | 10/2010 | Brinkmann et al. |
| 2010/0316645 A1 | 12/2010 | Imhof-Jung et al. |
| 2010/0322934 A1 | 12/2010 | Imhof-Jung et al. |
| 2010/0322935 A1 | 12/2010 | Croasdale et al. |

(56) References Cited

U.S. PATENT DOCUMENTS

| | | |
|---|---|---|
| 2011/0054151 A1 | 3/2011 | Lazar et al. |
| 2012/0149879 A1 | 6/2012 | Brinkmann et al. |
| 2012/0164726 A1 | 6/2012 | Klein et al. |
| 2012/0184718 A1 | 7/2012 | Bruenker et al. |
| 2012/0225071 A1 | 9/2012 | Klein et al. |
| 2012/0237506 A1 | 9/2012 | Bossenmaier et al. |
| 2012/0237507 A1 | 9/2012 | Bossenmaier et al. |
| 2012/0302737 A1 | 11/2012 | Christensen et al. |
| 2012/0321627 A1 | 12/2012 | Baehner et al. |
| 2013/0022601 A1 | 1/2013 | Brinkmann et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0156772 A1 | 6/2013 | Bossenmaier et al. |
| 2013/0266568 A1 | 10/2013 | Brinkmann et al. |
| 2013/0267686 A1 | 10/2013 | Brinkmann et al. |
| 2013/0273054 A1 | 10/2013 | Bossenmaier et al. |
| 2014/0249296 A1 | 9/2014 | Ploegh |
| 2014/0294810 A1 | 10/2014 | Lowman et al. |
| 2014/0370019 A1 | 12/2014 | Bruenker et al. |
| 2015/0004166 A1 | 1/2015 | Baehner et al. |
| 2015/0030598 A1 | 1/2015 | Croasdale et al. |
| 2015/0133638 A1 | 5/2015 | Wranik et al. |
| 2015/0166670 A1 | 6/2015 | Castoldi et al. |
| 2015/0232541 A1 | 8/2015 | Fenn |
| 2015/0232560 A1 | 8/2015 | Heindl et al. |
| 2015/0291704 A1 | 10/2015 | Beck |

FOREIGN PATENT DOCUMENTS

| | | |
|---|---|---|
| CN | 1232039 A | 10/1999 |
| CN | 1603345 A | 4/2005 |
| CN | 101037671 A | 9/2007 |
| CN | 101065151 A | 10/2007 |
| CN | 101205255 A | 6/2008 |
| CN | 101218251 A | 7/2008 |
| CN | 101355966 A | 1/2009 |
| EP | 0 307 434 B1 | 3/1989 |
| EP | 0 339 217 B1 | 11/1989 |
| EP | 0 340 109 A2 | 11/1989 |
| EP | 0 404 097 B1 | 12/1990 |
| EP | 0 425 235 B1 | 5/1991 |
| EP | 0 637 593 A1 | 2/1995 |
| EP | 1 391 213 A1 | 2/2004 |
| EP | 1 870 459 A1 | 12/2007 |
| EP | 2 050 764 A1 | 4/2009 |
| EP | 2 443 154 B1 | 4/2012 |
| JP | 2008-531049 A | 8/2008 |
| RU | 2005/124281 A1 | 1/2006 |
| RU | 2295537 C2 | 3/2007 |
| WO | WO-87/00195 A1 | 1/1987 |
| WO | WO-90/03430 A1 | 4/1990 |
| WO | WO-90/08187 A1 | 7/1990 |
| WO | WO-90/11294 A1 | 10/1990 |
| WO | WO-91/01133 A1 | 2/1991 |
| WO | WO-91/06305 A1 | 5/1991 |
| WO | WO-92/04053 A1 | 3/1992 |
| WO | WO-93/01161 A1 | 1/1993 |
| WO | WO-93/06217 A1 | 4/1993 |
| WO | WO-93/11161 A1 | 6/1993 |
| WO | WO-93/16185 A2 | 8/1993 |
| WO | WO-93/16185 A3 | 8/1993 |
| WO | WO-93/21232 A1 | 10/1993 |
| WO | WO-94/09131 A1 | 4/1994 |
| WO | WO-94/10202 A1 | 5/1994 |
| WO | WO-94/11026 A2 | 5/1994 |
| WO | WO-94/29350 A2 | 12/1994 |
| WO | WO-95/09917 A1 | 4/1995 |
| WO | WO-96/27011 A1 | 9/1996 |
| WO | WO-96/27612 A1 | 9/1996 |
| WO | WO-97/01580 A1 | 1/1997 |
| WO | WO-97/14719 A1 | 4/1997 |
| WO | WO-97/28267 A1 | 8/1997 |
| WO | WO-98/45331 A2 | 10/1998 |
| WO | WO-98/45331 A3 | 10/1998 |
| WO | WO-98/45332 A2 | 10/1998 |
| WO | WO-98/45332 A3 | 10/1998 |
| WO | WO-98/48032 A2 | 10/1998 |
| WO | WO-98/48032 A3 | 10/1998 |
| WO | WO-98/50431 A2 | 11/1998 |
| WO | WO-99/37791 A1 | 7/1999 |
| WO | WO-99/54342 A1 | 10/1999 |
| WO | WO-99/66951 A2 | 12/1999 |
| WO | WO-99/66951 A3 | 12/1999 |
| WO | WO-99/66951 C1 | 12/1999 |
| WO | WO-00/24770 A2 | 5/2000 |
| WO | WO-00/24770 A3 | 5/2000 |
| WO | WO-00/29004 A1 | 5/2000 |
| WO | WO-00/35956 A1 | 6/2000 |
| WO | WO-00/61739 A1 | 10/2000 |
| WO | WO-01/77342 A1 | 10/2001 |
| WO | WO-01/085795 A1 | 11/2001 |
| WO | WO-01/90192 A2 | 11/2001 |
| WO | WO-02/02781 A1 | 1/2002 |
| WO | WO-02/051870 A2 | 7/2002 |
| WO | WO-02/088172 A2 | 11/2002 |
| WO | WO-02/092620 A2 | 11/2002 |
| WO | WO-02/092620 A3 | 11/2002 |
| WO | WO-02/096948 A2 | 12/2002 |
| WO | WO-03/012069 A2 | 2/2003 |
| WO | WO-03/030833 A2 | 4/2003 |
| WO | WO-03/030833 A3 | 4/2003 |
| WO | WO-03/035694 A2 | 5/2003 |
| WO | WO-03/035835 A2 | 5/2003 |
| WO | WO-03/055993 A1 | 7/2003 |
| WO | WO-03/057134 A2 | 7/2003 |
| WO | WO-03/057134 A3 | 7/2003 |
| WO | WO-03/066660 A2 | 8/2003 |
| WO | WO-03/073238 A2 | 9/2003 |
| WO | WO-03/073238 A3 | 9/2003 |
| WO | WO-03/097105 A1 | 11/2003 |
| WO | WO-03/106501 A1 | 12/2003 |
| WO | WO-2004/032961 A1 | 4/2004 |
| WO | WO-2004/058298 A1 | 7/2004 |
| WO | WO-2004/065417 A2 | 8/2004 |
| WO | WO-2004/065540 A2 | 8/2004 |
| WO | WO-2004/072117 A2 | 8/2004 |
| WO | WO-2004/072117 A3 | 8/2004 |
| WO | WO-2004/092215 A2 | 10/2004 |
| WO | WO-2004/092215 A3 | 10/2004 |
| WO | WO-2005/000900 A1 | 1/2005 |
| WO | WO-2005/001025 A2 | 1/2005 |
| WO | WO-2005/001025 A3 | 1/2005 |
| WO | WO-2005/004809 A2 | 1/2005 |
| WO | WO-2005/004809 A3 | 1/2005 |
| WO | WO-2005/005635 A2 | 1/2005 |
| WO | WO-2005/005635 A3 | 1/2005 |
| WO | WO-2005/011735 A1 | 2/2005 |
| WO | WO-2005/018572 A2 | 3/2005 |
| WO | WO-2005/027966 A2 | 3/2005 |
| WO | WO-2005/035572 A2 | 4/2005 |
| WO | WO-2005/035572 A3 | 4/2005 |
| WO | WO-2005/035727 A2 | 4/2005 |
| WO | WO-2005/035727 A3 | 4/2005 |
| WO | WO-2005/044853 A2 | 5/2005 |
| WO | WO-2005/044859 A2 | 5/2005 |
| WO | WO-2005/051976 A2 | 6/2005 |
| WO | WO-2005/044853 A3 | 7/2005 |
| WO | WO-2005/063816 A2 | 7/2005 |
| WO | WO-2005/063816 A3 | 7/2005 |
| WO | WO-2005/074524 A2 | 8/2005 |
| WO | WO-2005/075514 A2 | 8/2005 |
| WO | WO-2006/020258 A2 | 2/2006 |
| WO | WO-2006/031370 A2 | 3/2006 |
| WO | WO-2006/031370 A3 | 3/2006 |
| WO | WO-2006/034488 A2 | 3/2006 |
| WO | WO-2006/034488 A3 | 3/2006 |
| WO | WO-2006/044908 A2 | 4/2006 |
| WO | WO-2006/044908 A3 | 4/2006 |
| WO | WO-2006/045049 A1 | 4/2006 |
| WO | WO-2006/068953 A2 | 6/2006 |
| WO | WO-2006/068953 A3 | 6/2006 |
| WO | WO-2006/082515 A2 | 8/2006 |
| WO | WO-2006/082515 A3 | 8/2006 |

(56) References Cited

FOREIGN PATENT DOCUMENTS

| | | |
|---|---|---|
| WO | WO-2006/089364 A1 | 8/2006 |
| WO | WO-2006/091209 A2 | 8/2006 |
| WO | WO-2006/091209 A3 | 8/2006 |
| WO | WO-2006/093794 A1 | 9/2006 |
| WO | WO-2006/103100 A2 | 10/2006 |
| WO | WO-2006/113665 A2 | 10/2006 |
| WO | WO-2006/114700 A2 | 11/2006 |
| WO | WO-2006/116260 A2 | 11/2006 |
| WO | WO-2007/024715 A2 | 3/2007 |
| WO | WO-2007/031875 A2 | 3/2007 |
| WO | WO-2007/044887 A2 | 4/2007 |
| WO | WO-2007/044887 A3 | 4/2007 |
| WO | WO-2007/048037 A2 | 4/2007 |
| WO | WO-2007/048037 A3 | 4/2007 |
| WO | WO-2007/068895 A1 | 6/2007 |
| WO | WO-2007/084181 A2 | 7/2007 |
| WO | WO-2007/084181 A3 | 7/2007 |
| WO | WO-2007/085837 A1 | 8/2007 |
| WO | WO-2007/089445 A2 | 8/2007 |
| WO | WO-2007/089445 A3 | 8/2007 |
| WO | WO-2007/095338 A2 | 8/2007 |
| WO | WO-2007/108013 A2 | 9/2007 |
| WO | WO/2007/109254 A2 | 9/2007 |
| WO | WO-2007/110205 A2 | 10/2007 |
| WO | WO-2007-110205 A3 | 10/2007 |
| WO | WO-2008/005828 A2 | 1/2008 |
| WO | WO-2008/005828 A3 | 1/2008 |
| WO | WO-2008/017963 A2 | 2/2008 |
| WO | WO-2008/017963 A3 | 2/2008 |
| WO | WO-2008/077077 A2 | 6/2008 |
| WO | WO-2008/077077 A3 | 6/2008 |
| WO | WO-2008/077546 A1 | 7/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2009/018386 A1 | 2/2009 |
| WO | WO-2009/021745 A1 | 2/2009 |
| WO | WO-2009/021754 A2 | 2/2009 |
| WO | WO-2009/023843 A1 | 2/2009 |
| WO | WO-2009/030780 A2 | 3/2009 |
| WO | WO-2009/030780 A3 | 3/2009 |
| WO | WO-2009/032782 A2 | 3/2009 |
| WO | WO-2009/032782 A3 | 3/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/126944 A1 | 10/2009 |
| WO | WO-2010/034441 A1 | 4/2010 |
| WO | WO-2010/035012 A1 | 4/2010 |
| WO | WO-2010/040508 A1 | 4/2010 |
| WO | WO-2010/040508 A8 | 4/2010 |
| WO | WO-2010/040508 A9 | 4/2010 |
| WO | WO-2010/045193 A1 | 4/2010 |
| WO | WO-2010/065882 A1 | 6/2010 |
| WO | WO-2010/069532 A1 | 6/2010 |
| WO | WO-2010/087994 A2 | 8/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/003557 A1 | 1/2011 |
| WO | WO-2011/028952 A1 | 3/2011 |
| WO | WO-2011/034605 A2 | 3/2011 |
| WO | WO-2011/133886 A2 | 10/2011 |
| WO | WO-2012/025525 A1 | 3/2012 |
| WO | WO-2012/025530 A1 | 3/2012 |
| WO | WO-2012/116927 A1 | 9/2012 |
| WO | WO-2013/003555 A1 | 1/2013 |
| WO | WO-2013/026833 A1 | 2/2013 |
| WO | WO-2013/092716 A1 | 6/2013 |
| WO | WO-2013/119966 A2 | 8/2013 |
| WO | WO-2013/174873 A1 | 11/2013 |
| WO | WO-2014/012085 A2 | 1/2014 |
| WO | WO-2014/049003 A1 | 4/2014 |
| WO | WO-2014/144357 A1 | 9/2014 |
| WO | WO-2016/055432 A2 | 4/2016 |
| WO | WO-2016/055432 A3 | 4/2016 |
| WO | WO-2016/087416 A1 | 6/2016 |

OTHER PUBLICATIONS

Atwell et al. (1997). "Stable Heterodimers from Remodeling the Domain Interface of a Homodimer using a phage display library," *J. Mol. Biol.* 270:26-35.

Avgeris et al. (May 2010). "Kallikrein-related peptidase genes as promising biomarkers for prognosis and monitoring of human malignancies," *Biol. Chem* 391(5):505-511.

Bao et al. (Jul. 2010). "HER2-mediated upregulation of MMP-1 is involved in gastric cancer cell invasion," *Arch Biochem Biophys* 499(1-2):49-55.

Barnes et al. (2000). "Advances in animal cell recombinant protein production: GS-NS0 expression system," *Cytotechnology* 32:109-123.

Barnes et al. (2001). "Characterization of the stability of recombinant protein production in the GS-NS0 expression system," *Biotech Bioeng.* 73:261-270.

Bera et al. (Aug. 21, 1998). "A bivalent disulfide-stabilized Fv with improved antigen binding to erbB2," *J. Mol. Biol.* 281(3):475-483.

Boado et al. (Feb. 15, 2010). "IgG-single chain Fv fusion protein therapeutic for Alzheimer's disease: Expression in CHO cells and pharmacokinetics and brain delivery in the rhesus monkey," *Biotechnology and Bioengineering* 105(3):627-635.

Boerner et al. (1991). "Production of antigen-specific human monoclonal antibodies from in vitro-primed human splenocytes," *J. Immunol.* 147(1):86-95.

Briggs et al. (Jan. 2010). "Cystatin E/M suppresses legumain activity and invasion of human melanoma," *BMC Cancer* 10:17.

Brinkmann, U. et al. (1993). "A recombinant immunotoxin containing a disulfide-stabilized Fv fragment," *PNAS* 90(16):7538-7542.

Brüggemann et al. (1993). "Designer mice: the production of human antibody repertoires in transgenic animals," *Year Immunol.* 7:33-40.

Brüggemann et al. (Nov. 1, 1987). "Comparison of the effector functions of human immunoglobulins using a matched set of chimeric antibodies," *J. Exp. Med.* 166(5):1351-1361.

Brunhouse et al. (1979). "Isotypes of IgG: Comparison of the primary structures of three pairs of isotypes which differ in their ability to activate complement," *Mol. Immunol.* 16:907-917.

Burton et al. (Nov. 27, 1980). "The C1q receptor site on immunoglobulin G," *Nature* 288:338-344.

Carter et al. (May 1992). "Humanization of an anti-p185$^{HER2}$ antibody for human cancer therapy," *PNAS* 89:4285-4289.

Carter. (2001). "Bispecific human IgG by design," *J. Immunol. Methods* 248:7-15.

Chernaia. (Sep.-Oct. 1998). "[Cathepsin L from human brain tumor. Purification and contents]." Ukr Biokhim Zh. 70(5):97-103 (Article in Russian).

Chung, D.E. et al. (Oct. 1, 2006). "Development of a novel albumin-binding prodrug that is cleaved by urokinase-type-plasminogen activator (uPA)," *Bioorg Med Chem Lett.* 16(19):5157-5163.

Cohen et al. (Aug. 1972). "Nonchromosomal antibiotic resistance in bacteria: Genetic transformation of *Escherichia coli* by R-factor DNA," *PNAS* 69(8):2110-2114.

Cole et al. (1985). "The EBV-hybridoma technique and its application to human lung cancer," *Monoclonal Antibodies and Cancer Therapy* pp. 77-96.

Coloma et al. (Feb. 1997). "Design and production of novel tetravalent bispecific antibodies," *Nat. Biotechnol.* 15(2):159-163.

Cordingley et al. (1990). "Substrate requirements of human rhinovirus 3C protease for peptide cleavage in vitro," *J. Biol. Chem.* 265(16):9062-9065.

(56) References Cited

OTHER PUBLICATIONS

Cortesio et al. (Mar. 10, 2008). "Calpain 2 and PTP1B function in a novel pathway with Src to regulate invadopodia dynamics and breast cancer cell invasion," *J. Cell Biol.* 180(5):957-971.
Crawford et al. (Jun. 2002). "Matrix metalloproteinase-7 is expressed by pancreatic cancer precursors and regulates acinar-to-ductal metaplasia in exocrine pancreas," *J. Clin. Invest.* 109(11):1437-1444.
Cudic et al. (Aug. 2009). "Extracellular proteases as targets for drug development," *Curr. Protein Pept Sci* 10(4):297-307.
Cullen et al. (Apr. 2010). "Granzymes in cancer and immunity," *Cell Death Differ* 17(4):616-623
Davies et al. (2001). "Expression of GnTIII in a recombinant anti-CD20 CHO production cell line: Expression of antibodies with altered glycoforms leads to an increase in ADCC through higher affinity for FcγRIII," *Biotechnol. Bioeng.* 74:288-294.
Deyev et al. (Sep. 2008). "Multivalency: the hallmark of antibodies used for optimization of tumor targeting by design," *BioEssays* 30(9):904-918.
Donaldson et al. (Nov. 15, 2009) "Design and development of masked therapeutic antibodies to limit off-target effects: Application to anti-EGFR antibodies," *Cancer Biology & Therapy* 8(22):2145-2150.
Durocher et al. (2002). "High-level and high-throughput recombinant protein production by transient transfection of suspension-growing human 293-EBNA1 cells," *Nucl. Acids Res.* 30(2)(e9):1-9.
Fischer et al. (2007). "Bispecific antibodies: Molecules that enable novel therapeutic strategies," *Pathobiology* 74:3-14.
Flatman et al. (2007). "Process analytics for purification of monoclonal antibodies," *J. Chromatogr B* 848:79-87.
Galamb et al. (2008). "Inflammation, adenoma and cancer: Objective classification of colon biopsy specimens with gene expression signature," *Dis. Markers* 25(1):1-16.
Geisse et al. (1996). "Eukaryotic expression systems: A comparison," *Protein Expr. Purtif* 8:271-282.
Gerspach et al. (2006). "Target-selective activation of a TNF prodrug by urokinase-type plasminogen activator (uPA) mediated proteolytic processing at the cell surface," *Cancer Immunol. Immunother* 55:1590-1600.
Graham et al. (1973). "A new technique for the assay of infectivity of huma adenovirus 5 DNA," *Virology* 52:456-467.
Henry et al. (Mar. 15, 2007). "Clinical implications of fibroblast activation protein in patients with colon cancer," *Clin Cancer Res.* 13(6):1736-1741.
Hezareh et al. (Dec. 2001). "Effector function activities of a panel of mutants of a broadly neutralizing antibody against human immunodeficiency virus type 1," *J. Virol.* 75(24):12161-12168.
Hollander. (Mar. 2009). "Bispecific antibodies for cancer therapy," *Immunotherapy* 1(2):211-222.
Holliger et al. (Sep. 2005). "Engineered antibody fragments and the rise of single domains," *Nature Biotech* 23(9):1126-1136.
Hoogenboom et al. (1992). "By-passing immunisation. Human antibodies from synthetic repertoires of germline $V_H$ gene segments rearranged in vitro," *J. Mol. Biol.* 227:381-388.
Idusogie et al. (2000). "Mapping of the C1q binding site on rituxan, a chimeric antibody with a human IgG1 Fc," *J. Immunol.* 164:4178-4184.
International Search Report mailed on Dec. 6, 2011, for PCT Patent Application No. PCT/EP2011/064476 filed on Aug. 23, 2011, seven pages.
Jakobovits et al. (1993). "Germ-line transmission and expression of a human-derived yeast artificial chromosome," *Nature* 362:255-258.
Jakobovits et al. (Mar. 1993). "Analysis of homozygous mutant chimeric mice: Deletion of the immunoglobulin heavy-chain joining region blocks B-cell development and antibody production," *PNAS* 90:2551-2555.
Jefferis et al. (1998). "IgG-Fc-mediated effector functions: molecular definition of interaction sites for effector ligands and the role of glycosylation," *Immunol. Rev.* 163:59-76.

Jia et al. (Jun. 29, 2010). "A novel trifunctional IgG-like bispecific antibody to inhibit HIV-1 infection and enhance lysis of HIV by targeting activation of complement," *Virology Journal* 7(142):1-4.
Johnson et al. (2000). "Kabat database and its applications: 30 years after the first variability plot," *Nucleic Acids Res.* 28(1):214-218.
Kabat et al. (Jul. 1975). "Evolutionary and structural influences on light chain constant ($C_L$) region of human and mouse immunoglobulins," *PNAS* 72(7):2785-2788.
Karadag et al. (Apr. 15, 2006, e-pub. Dec. 22, 2005). "ADAM-9 (MDC-9/meltrin-γ), a member of the a disintegrin and metalloproteinase family, regulates myeloma-cell-induced interleukin-6 production in osteoblasts by direct interaction with the αvβ5 integrin," *Blood* 107(8):3271-3278.
Kaufman. (2000). "Overview of vector design for mammalian gene expression," *Mol. Biotechnol.* 16:151-160.
Kazama et al. (Jan. 6, 1995). "Hepsin, a putative membrane-associated serine protease, activates human factor VII and initiates a pathway of blood coagulation on the cell surface leading to thrombin formation," *J. Biol. Chem.* 270(1):66-72.
Kleinschmidt et al. (Mar. 21, 2003). "Design of a modular immunotoxin connected by polyionic adapter peptides," *J. Mol. Biol.* 327(2):445-452.
Kontermann et al. (Apr. 30, 2010). "Chapter 14: Disulfide-stabilized Fv fragments," *Antibody Engineering* 2:181-189.
Lamkanfi et al. (Jan. 2009). "Inflammasomes: guardians of cytosolic sanctity," *Immunol. Rev.* 227(1):95-105.
Lee et al. (Jun. 16, 2009). "Using substrate specificity of antiplasmin-cleaving enzyme for fibroblast activation protein inhibitor design," *Biochemistry* 48(23):5149-5158.
Leeman et al. (2002). "The Structure, Regulation, and Function of Human Matrix Metalloproteinase-13," *Crit. Rev Biochem Mol. Biol.* 37(3):149-166.
Lifely et al. (1995). "Glycosylation and biological activity of CAMPATH-1H expressed in different cell lines and grown under different culture conditions," *Glycobiology* 5(8):813-822.
Liotta et al. (Mar. 6, 1980). "Metastatic Potential Correlates with Enzymatic Degradation of Basement Membrane Collagen," *Nature* 284(5751):67-68.
Lopez-Otin et al. (Apr. 2010). "The regulatory crosstalk between kinases and proteases in cancer," *Nat. Rev. Cancer* 10(4):278-292.
Love et al. (1989). "Recombinant antibodies possessing novel effector functions," *Methods Enzymol.* 178:515-527.
Lu et al. (Aug. 2009). "ADAMTS1 and MMP1 proteolytically engage EGF-like ligands in an osteolytic signaling cascade for bone metastasis," *Genes Dev.* 23(16):1882-1894.
Lukas et al. (Dec. 1981) "Inhibition of C1-mediated immune hemolysis by monomeric and dimeric peptides from the second constant domain of human immunoglobulin G," *J. lmmunol.* 127(6):2555-2560.
Lund et al. (1995). "Oligosaccharide-protein interactions in IgG can modulate recognition by Fc gamma receptors," *FASEB* 9:115-119.
Makrides et al. (1999). "Components of Vectors for Gene Transfer and Expression in Mammalian Cells," *Protein Expr. Purif* 17:183-202.
Mamoune et al. (Aug. 1, 2003). "Calpain-2 as a target for limiting prostate cancer invasion," *Cancer Res.* 63(15):4632-4640.
Marks et al. (1991). "By-passing immunization. Human antibodies from V-gene libaries displayed on phage," *J. Mol. Biol.* 222:581-597.
Marvin et al. (Jun. 2005). "Recombinant approaches to IgG-like bispecific antibodies," *Acta Pharmacol. Sin* 26(6):649-658.
Marvin et al. (2006). "Bispecific antibodies for dual-modality cancer therapy: Killing two signaling cascades with one stone," *Curr. Opin. Drug Discov. Devl.* 9(2):184-193.
Matrisian et al. (Oct. 1999). "Cancer biology: Extracellular proteinases in malignancy" *Curr. Biol.* 9(20):R776-R778.
Merchant et al. (Jul. 1998). "An efficient route to human bispecific IgG," *Nat. Biotechnol.* 16:677-681.
Michaelson et al. (Mar. 2009, e-pub. Mar. 11, 2009). "Anti-tumor activity of stability-engineered IgG-like bispecific antibodies targeting TRAIL-R2 and LTβR," *mAbs* 1(2):128-141.

(56) References Cited

OTHER PUBLICATIONS

Mimura et al. (Dec. 7, 2001, e-pub. Sep. 20, 2001). "Role of oligosaccharide residues of IgG1-Fc in FcγRIIb binding," *J. Biol. Chem.* 276(49):45539-45547.
Minn et al. (Jul. 28, 2005). "Genes that Mediate Breast Cancer Metastasis to Lung," *Nature* 436(7050):518-524.
Morgan et al. (1995). "The N-terminal end of the $C_H2$ domain human IgG1 anti-HLA-DR is necessary for C1q, FcγRI and FcγRIII binding," *Immunology* 86:319-324.
Morrison et al. (Nov. 1984). "Chimeric human antibody molecules: Mouse antigen-binding domains with human constant region domains," *PNAS* 81:6851-6855.
Morrison. (2007). "Two heads are better than one," *Nature biotechnology* 25(11):1233-1234.
Mukhopadhyay et al. (2010). "Matrix metalloproteinase-12 is a therapeutic target for asthma in childen and young adults," *J Allergy Clin Immunol.* 126(1):70-76.
Müller et al. (2007). "Recombinant bispecific antibodies for cellular cancer immunotherapy," *Current Opin. Mol. Thera.* 9(4):319-326 (2007).
Netzel-Arnett et al. (Apr. 15, 1991). Sequence Specificities of Human Fibroblast and Neutrophil Collagenaes, *J. Biol.Chem.* 266(11):6747-6755.
Netzel-Arnett et al. (Jun. 29, 1993). "Comparative sequence specificities of human 72- and 92-kDa gelatinases (type IV collagenases) and PUMP (matrilysin)," *Biochemistry* 32(25):6427-6432.
Neuberger et al. (Mar. 21, 1985). "A hapten-specific chimaeric IgE antibody with human physiological effector function," *Nature* 314:268-270.
Niwa et al. (2005, e-pub. Sep. 22, 2005). "IgG subclass-independent improvement of antibody-dependent cellular cytotoxicity by fucose removal from $Asn^{297}$-linked oligosaccharides," *J. Immunol. Methods* 306:151-160.
Norderhaug et al. (1997). "Versatile vectors for transiet and stable expression of recombinant antibody molecules in mammalian cells," *J. Immunol. Methods* 204:77-87.
Orcutt et al. (Apr. 2010, e-pub. Dec. 17, 2009). "A modular IgG-scFv bispecific antibody topology," *Protein Engineering, Des. & Selection* 23(4):221-228.
Orlandi et al. (May 1989). "Cloning immunoglobulin variable domains for expression by the polymerase chain reaction," *PNAS* 86:3833-3837.
PreScission Protease, GE Healthcare Catologue No. 27-0843-01, located http://www.gelifesciences.com/webapp/wcs/stores/servlet/productById/en/GELifeScience, last visited on Jul. 10, 2013, one page.
Radaev et al. (May 11, 2001). "Recognition of IgG by Fcγ receptor. The role of Fc glycosylation and the binding of peptide inhibitors," *J. Biol. Chem.* 276(19):16478-16483.
Rajagopal et al. (1997). "A form of anti-Tac(Fv) which is both single-chain and disulfide stabilized: comparison with its single-chain and disulfide-stabilized homologs," *Prot. Engin.* 10(12):1453-1459.
Raju. (Apr. 2003). "Glycosylation variations with expression systems and their impact on biological activity of therapeutic immunoglobulins," *Bioprocess Int.* 1:44-53.
Rawlings. (2009, e-pub. Nov. 2, 2009). "A large and accurate collection of peptidase clevages in the MEROPS database," *Database (Oxford)*, pp. 1-14.
Reiter et al. (Jul. 15, 1994). "Improved binding and antitumor activity of a recombinant anti-erbB2 immunotoxin by disulfide stabilization of the Fv fragment," *JBC* :269(28):18327-18331.
Reiter et al. (1994). "Cytotoxic and antitumor activity of a recombinant immunotoxin composed of disulfide-stabilized anti-Tac Fv fragment and truncated Pseudomonas exotoxin," *International Journal of Cancer* 58:142-149.
Reiter et al. (May 15, 1994). "Antitumor activity and pharmacokinetics in mice of a recombinant immunotoxin containing a disulfide-stabilized Fv fragment," *Cancer Research* 54:2714-2718.

Reiter, Y. et al. (Feb. 1996, e-pub, Feb. 1, 1996). "Antibody engineering of recombinant Fv immunotoxins for improved targeting of cancer: disulfide-stabilized Fv immunotoxins," *Clin. Cancer Res.* 2(2):245-252.
Reiter et al. (1995). "Disulfide stabilization of antibody Fv: computer predictions and experimental evaluation," *Protein Engineering* 8(12):1323-1331.
Reiter et al. (Mar. 1995). "Construction of a functional disulfide-stabilized TCR Fv indicates that antibody and TCR Fv frameworks are very similar in structure," *Immunity* 2:281-287.
Reiter, Y. et al. (Oct. 1996), "Engineering antibody Fv fragments for cancer detection and therapy: Disulfide-stabilized Fv fragments," *Nature Biotechnology* 14:1239-1245.
Ridgway et al. (1996). "'Knobs-into-holes' engineering of antibody $C_H3$ domains for heavy chain heterodimerization," *Protein Eng.* 9(7):617-621.
Riechmann et al. (Mar. 24, 1988). "Reshaping human antibodies for therapy," *Nature* 332(6162):323-327.
Routier et al. (1997). "The glcosylation pattern of humanized IgGI antibody (DI.3) expressed in CHO cells," *Glycoconjugate J.* 14:201-207.
Ruppert et al. (1997). "Protease levels in breast, ovary and other gynecological tumor tissues: Prognostic importance in breast cancer," *Cancer Detect. Prev.* 21(5):452-459.
Schlaeger. (1996). "The protein hydrolysate, Primatone RL, is a cost-effective multiple growth promoter of mammalian cell culture in serum-containing and serum-free media and displays anti-apoptosis properties," J. Immunol. Methods 194: 191-199.
Schlaeger et al. (1999). "Transient gene expression in mammalian cells grown in serum-free suspension culture," *Cytotechnology* 30:71-83.
Schmiedl, A. et al. (Oct. 2000). "Expression of a bispecific dsFv-dsFv' antibody fragment in *Escherichia coli*," *Protein Engineering* 13(10):725-734.
Scott et al. (Nov. 2010). "Biologic protease inhibitors as novel therapeutic agents," *Biochimie* 92(11):1681-1688.
Shen, J. et al. (Jan. 10, 2007, e-pub. Oct. 26, 2006). "Single variable domain antibody as a versatile building block for the construction of IgG-like bispecific antibodies," *J. of Immunological Methods* 318(1-2):65-74.
Shen, J. et al. (Apr. 21, 2006, e-pub, Feb. 15, 2006). "Single variable domain-IgG fusion: A novel recombinant approach to Fc domain-containing bispecific antibodies," *J. of Biological Chemistry* 281(16):10706-10714.
Shields et al. (Jul. 26, 2002). "Lack of fucose on human IgG1 N-linked oligosaccharide improves binding to human Fcγ RIII and antibody-dependent cellular toxicity," *J. Biol. Chem.* 277(30):26733-26740.
Shields et al. (Mar. 2, 2001). "High resolution mapping of the binding site on human IgG1 for FcγRI, FcγRII, FcγRIII, and FcRn and design for IgG1 variants with improved binding to the FcγR," *J. Biol. Chem.* 276(9):6591-6604.
Shinkawa et al. (2003). "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.* 278(5):3466-3473.
Simmons et al. (2002). "Expression of full-length immunoglobulins in *Escherichia coli*: Rapid and efficient production of aglycosylated antibodies," *J. Immunol. Methods* 263:133-147.
Stetler-Stevenson. (1994-1995). "Progelatinase A activation during tumor cell invasion," *Invasion Metastasis* 14(1-6):259-268.
Thommesen et al. (2000). "Lysine 322 in the human IgG3 $C_H2$ domain is crucial for antibody dependent complement activation," *Mol. Immunol.* 37:995-1004.
Tripathi et al. (2008, e-pub. Sep. 9, 2008). "Laminin-332 is a substrate for hepsin, a protease associated with prostate cancer progression," *JBC* 283:30576-30584.
Umana et al. (Feb. 1999). "Engineered glycoforms of an antineuroblastoma IgG1 with optimized antibody-dependent cellular cytotoxic activity," *Nature Biotechnol.* 17:176-180.
Van Dijk et al. (2001). "Human antibodies as next generation therapeutics," *Curr. Opin. Chem. Biol.* 5:368-374.

(56) References Cited

OTHER PUBLICATIONS

Van't Veer et al. (Jan. 31, 2002). "Gene expression profiling predicts clinical outcome of breast cancer," *Nature* 415(6871):530-536.
Vazquez-Ortiz et al. (Jun. 30, 2005). "Overexpression of cathespin F, matrix metalloproteinases 11 and 12 in cervical cancer," *BMC Cancer* 5:68.
Velasco et al. (Oct. 28, 1994). "Human cathepsin O. Molecular cloning from a breast carcinoma, production of the active enzyme in *Escherichia coli*, and expression analysis in human tissues," *J. Biol Chem* 269(43):27136-27142.
Veveris-Lowe et al. (2007). "Seminal Fluid Characterization for Male Fertility and Prostate Cancer: Kallikrein-Related Serine Proteases and whole Proteome Approaches," *Semin Thromb Hemost*. 33(1):87-99.
Vijayalakshmi. (1998). "Antibody Purification Methods," *App. Biochem. Biotech* 75:93-102.
Walker et al. (Jun. 1994). "Efficient and rapid affinity purification of proteins using recombinant fusion proteases," *Bio/Technology* 12:601-605.
Webber et al. (1995). "Preparation and characterization of a disulfide-stabilized Fv fragment of the anti-Tac antibody: comparison with its single-chain analog," *Molecular Immunology* 32(4):249-258.
Werner. (Aug. 1998). "Appropriate mammalian expression systems for biopharmaceuticals," *Arzneimittelforschung* 48:870-880.
Wielockx et al. (Apr.-Jun. 2004). "Matrilysin (matrix metalloproteinase-7): A new promising drug target in cancer and inflammation!" *Cytokine Growth Factor Rev*. 15(2-3): 111-115.
Wright et al. (Aug. 2010). "ADAM28: a potential oncogene involved in asbestos-related lung adenocarcinomas," *Genes Chromosomes Cancer* 49(8):688-698.
Wright et al. (Jan. 1997), "Effect of glycosylation on antibody function: implications for genetic engineering," *Trends Biotechnol*. 15:26-32.
Written Opinion of the International Searching Authority mailed on Dec. 6, 2011, for PCT Patent Application No. PCT/EP2011/064476 filed on Aug. 23, 2011, four pages.
Wu et al. (Nov. 2007). "Simultaneous targeting of multiple disease mediators by a dual-variable-domain immunoglobulin" *Nature Biotech*. 25(11):1290-1297.
Brinkmann et al. "Disulfide-stabilized Fv fragments," Chapter 14 in 2 in *Antibody Engineering*, Kontermaan et al. eds., vol. 2, Springer-Verlag, Berlin Heidelberg, Germany, pp. 181-189, (Apr. 30, 2010).
Ausubel et al., Short Protocols in Molecular Biology, Greene Publishing and Wiley Interscience, New York, New York, (Table of Contents), (1987).
Borgström et al., "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," *Cancer Research* 56:4032-4039, (1996).
Burgess et al., "Possible dissociation of the heparin-binding and mitogenic activities of heparin-binding (acidic fibroblast) growth factor-1 from its receptor-binding activities by site-directed mutagenesis of a single lysine residue," *Journal of Cell Biology* 111:2129-2138, (Nov. 1990).
Caron et al., "Engineered humanized dimeric forms of IgG are more effective antibodies," *J. Exp. Med.* 176(4):1191-1195, (Oct. 1, 1992).
Carro et al., "Serum insulin-like growth factor I regulates brain amyloid-β levels," *Nature Medicine* 8(12):1390-1397, (2002, e-pub. Nov. 4, 2002).
Chan et al., "Variable Region Domain Exchange in Human IgGs Promotes Antibody Complex Formation with Accompanying Structural Changes and Altered Effector Functions," *Molecular Immunology* 41:(5)527-538, (2004).
Chitnis et al., "The type 1 insulin-like growth factor receptor pathway," *Clin. Cancer Res.* 14(20):6364-6370, (Oct. 16, 2008).
Coxon et al., "Combined treatment of angiopoietin and VEGF pathway antagonists enhances antitumor activity in preclinical models of colon carcinoma," *99th AACR Annual Meeting*, Abstract #1113, (Apr. 2008).
Edelman et al., "The covalent structure of an entire γG immunoglobulin molecule," *Proc. Natl. Acad. Sci. USA* 63:78-85, (1969).
Gold et al., "A novel bispecific, trivalent antibody construct for targeting pancreatic carcinoma," *Cancer Res.* 68(12):4819-4826, (2008).
Goldenberg et al., "Bi-Specific Antibodies that Bind Specific Target Tissue and Targeted Conjugates," Derwent Information Ltd., 12 pages, (2012).
Grote et al., "Bispecific Antibody Derivatives Based on Full-Length IgG Formats," Chapter 16 in *Methods in Molecular Biology* 901:247-263, (2012).
Gunasekaran et al., "Enhancing antibody Fc heterodimer formation through electrostatic steering effects: Applications to bispecific molecules and monovalent IgG," *The Journal of Biological Chemistry* 285(25):19637-19646, (Jun. 18, 2010).
Hartog et al., "The Insulin-like growth factor 1 receptor in cancer: Old focus, new future," European Journal of Cancer, Pergamon Press, Oxford, GB, 43(13):1895-1904, (Aug. 23, 2007).
Hust et al., "Single Chain Fab (scFab) Fragment," *BMC Biotechnology* 7(14):1-15, (Mar. 8, 2007).
Ibragimova et al., "Stability of the β-Sheet of the WW domain: A molecular dynamics simulation study," *Biophysical Journal* 77:2191-2198, (Oct. 1999).
International Search Report mailed on Dec. 6, 2011, for PCT Patent Application No. PCT/EP2011/064468 filed on Aug. 23, 2011, seven pages.
Jendreyko et al., "Simultaneous, Phenotypic Knockout of VEGF-R2 and Tie-2 With an Intradiabody Enhances Antiangiogenic Effects in Vivo," Therapieoptimierung and Risikostratifizierung, Scripps Research Institute, 218:143-151, (2006).
Kabat et al., Sequences of Proteins of Immunological Interest (Table of Contents and Introduction), 5th edition, Bethesda, MD: Public Health Service, NIH, vol. 1, (1991).
Kim et al., "Inhibition of Vascular Endothelial Growth Factor-Induced Angiogenesis Suppresses Tumour Growth In Vivo," *Nature* 362:841-844, (1993).
Kobayashi et al., "Similarities in the Biodistribution of Iodine-Labeled Anti-Tac Single-Chain Disulfide-Stabilized Fv Fragment and Anti-Tac Disulfide-Stabilized Fv Fragment," *Nuclear Medicine & Biology* 25:387-393, (1998).
Kodukula et al., "Biosynthesis of phosphatidylinositol glycan-anchored membrane proteins. Design of a simple protein substrate to characterize the enzyme that cleaves the COOH-terminal signal peptide," *The Journal of Biological Chemistry* 266(7):4464-4470 (Mar. 5, 1991).
Lazar et al., "Transforming growth factor α: Mutation of aspartic acid 47 and leucine 48 results in different biological activities," *Molecular and Cellular Biology* 8(3):1247-1252, (Mar. 1988).
Liang et al., "Cross-species Vascular Endothelial Growth Factor (VEGF)-blocking Antibodies Completely Inhibit the Growth of Human Tumor Xenografts and Measure the Contribution of Stromal VEGF," *Journal of Biological Chemistry* 281(2):951-961, (2006).
Lin et al., "Structure-Function relationships in glucagon: Properties of highly purified des-his-, monoiodo-, and [Des-Asn$^{28}$, Thr$^{29}$](homoserine lactone$^{27}$)-glucagon," *Biochemistry USA* 14:1559-1563, (1975).
Liu et al., "Clinical and imaging diagnosis of primary hepatic lymphoma," *J First Mil Med. Univ*, 25(10):1290-1292, three pages, (2005). (Translation of the Abstract Only.).
Lu et al., "A Fully Human Recombinant IgG-Like Bispecific Antibody to Both the Epidermal growth Factor Receptor and the Insulin-Like Growth Factor Receptor for Enhanced Antitumor Activity," *The Journal of Biological Chemistry* 280(20):19665-19672, (May 20, 2005).
Meissner et al., "Transient Gene Expression: Recombinant Protein Production with Suspension-Adapted HEK293-EBNA Cells," *Biotechnology and Bioengineering* 75:197-203, (2001).

(56) References Cited

OTHER PUBLICATIONS

Melnyk et al., Vascular Endothelial Growth Factor Promotes Tumor Dissemination by a Mechanism Distinct from Its Effect on Primary Tumor Growth, *Cancer Research* 56:921-924, (1996).
Miller et al., "Design, Construction, and In Vitro Analyses of Multivalent Antibodies," *J. Immunol.* 170:4854-4861, (2003).
Milstein et al., "Hybrid Hybridomas and Their Use in Immunohistochemistry" *Nature* 305: 537-540, (Oct 6, 1983).
Morrison et al., "Variable region domain exchange influences the functional properties of IgG," *Journal of Immunology, American Association of Immunologists* 160:2802-2808, (Jan 1, 1998).
Morrison. "Success in Specification," *Nature* 368:812-813, (Apr. 1994).
Müller et al., "The first constant domain ($C_H1$ and $C_L$) of an antibody used as heterodimerization domain for bispecific miniantibodies," *FEBS Letters* 422:259-264, (1998).
Müller et al., "Bispecific Antibodies," Chapter 2 in Handbook of Therapeutic Antibodies, Dübel, S. ed., Wiley-VCH Verlag GmbH & Company KGaA, Weinheim, pp. 345-378, (2007).
Ohno et al., "Antigen-binding specificities of antibodies are primarily determined by seven residues of $V_H$," *Proc. Natl. Acad. Sci. USA* 82(9):2945-2949, (May 1985).
Oliner et al., Suppression of Angiogenesis and Tumor Growth by Selective Inhibition of Angiopoietin-2, *Cancer Cell* 6:507-516, (2004).
Pace et al., "How to Measure and Predict the Molar Absorption Coefficient of a Protein," *Protein Science* 4(11): 2411-2423, (Nov. 1995).
Pakula et al., "Genetic analysis of protein stability and function," *Annu. Rev. Genet.* 23:289-310, (1989).
Plückthun et al., "New Protein Engineering Approaches to Multivalent and Bispecific Antibody Fragments," *Immunotechnology* 3:83-105, (1997).
Roitt et al., "Immunology" English Translation by McElroy Translation Company, Moscow "Mir" (2000), p. 110-111, eight pages.
Rossi, E.A. et al., "Multivalent Anti-CD20/Anti-CD22 Bispecific Antibody Fusion Proteins Made by the DNL Method Show Potent Lymphoma Cytotoxicity," *Blood, American Society of Hematology* 8:11, pp. 707A, (2006).
Sambrook et al., Molecular Cloning: A Laboratory Manual "The Table of Contents" Cold Spring Harbor, New York: Cold Spring Harbor Laboratory Press, (1989).
Schaefer et al., "Immunoglobulin domain crossover as a generic approach for the production of bispecific IgG antibodies," *Proc. Natl. Acad. Sci. U.S.A.* 108(27):11187-11192, (Jul. 5, 2011, e-pub. Jun. 20, 2011).
Schmidt et al., "Suppression of Metastasis Formation by a Recombinant Single Chain Antibody-Toxin Targeted to Full-length and Oncogenic Variant EGF Receptors," *Oncogene* 18:1711-1721, (1999).
Schoonjans, et al., "Fab Chains as an Efficient Heterodimerization Scaffold for the Production of Recombinant Bispecific and Trispecific Antibody Derivatives," *Journal of Immunology* 165:7050-7057, (2000).
Schwartz et al., "A superactive insulin: [B10-aspartic acid]insulin(human)," *Proc. Natl. Acad. Sci. USA* 84:6408-6411, (Sep. 1987).
Simon et al., "Antibody Domain Mutants Demonstrate Autonomy of the Antigen Binding Site," *The EMB O Journal* 9(4):1051-1056, (1990).
Singer, M. and Berg, P. "Genes and genomes," Moscoer, MIR 1(1998) 63-64 (With English Translation.).
Stevenson et al., "A chimeric antibody with dual Fc regions (*bis* FabFc) prepared by manipulations at the IgG hinge," *Anti-cancer Drug Des.* 3(4):219-230, (Mar. 1989).
U.S. Appl. No. 13/773,167, filed Feb. 21, 2013, for Brinkmann et al.
U.S. Appl. No. 13/773,013, filed Feb. 21, 2013, for Brinkmann et al.
Van Spriel et al., "Immunotherapeutic perspective for bispecific antibodies," *Immunology Today* 21(8):391-397, (Aug. 2000).
Warren et al., "Regulation of Vascular Endothelial Growth Factor of Human Colon Cancer Tumorigenesis in a Mouse Model of Experimental Liver Metastasis," *J. Clin. Invest.* 95:1789-1797, (1995).
Willems et al., "Optimizing expression and purification from cell culture medium of trispecific recombinant antibody derivatives" *Journal of Chromatography B* 786:161-176, (2003).
Woof et al., "Human antibody-FC receptor interactions illuminated by crystal structures," *Nat. Rev. Immunol.* 4:1-11, (2004).
Written Opinion of the International Searching Authority mailed on Dec. 6, 2011, for PCT Patent Application No. PCT/EP2011/064468 filed on Aug. 23, 2011, four pages.
Xie et al., "A New format of bispecific antibody: Highly efficient heterodimerization, expression and tumor cell lysis," *J. of Immunol. Methods* 296:95-101, (2005).
Zuo et al. "An efficient route to the production of an IgG-like bispecific antibody," *Protein Engineering* 13(5):361-367, (2000).
Chilean Office Action dated Jan. 11, 2012, for Chilean Application No. 3781-2008, 19 pages.
Chilean Office Action dated Aug. 1, 2012, for Chilean Application No. 2008003779, 22 pages.
Chinese Office Action dated Mar. 28, 2012, for Chinese Application No. 200880120258.8, 10 pages.
Korean Office Action dated Feb. 24, 2012, for Korean Patent Application No. 20107013773, 6 pages.
Citations from Israeli Office Action, dated Feb. 29, 2012, in Israeli Patent Application No. 205285, 2 pages.
Japanese Office Action dated Aug. 14, 2012, for Japanese Patent Application No. 2010-538440, 12 pages.
Japanese Office Action dated Aug. 14, 2012, for Japanese Patent Application No. 2010-538441, 11 pages.
Korean Office Action dated Jan. 31, 2012, for Korean Patent Application No. 2010-7013760, 11 pages.
European Search Report dated Mar. 14, 2006, for European Patent Application No. 07024864.6, 8 pages.
European Search Report dated Aug. 31, 2009, for European Patent Application No. 09005108.7, 6 pages.
Taiwanese Search Report for Taiwanese Patent Application No. 099110151, filed on Apr. 1, 2010, Completion of Search Sep. 12, 2012, 1 page.
International Search Report mailed on Aug. 5, 2010, for PCT Application No. PCT/EP2010/003559, filed on Jun. 14, 2010, 10 pages.
Arié et al. (2001). "Chaperone Function of FkpA, a Heat Shock Prolyl Isomerase, in the Periplasm of *Escherichia coli*," *Mol. Microbiol.* 39(1):199-210.
Arndt, K.M. et al. (Sep. 7, 2001). "Helix-stabilized Fv (hsFv) antibody fragments: substituting the constant domains of a Fab fragment for a heterodimeric coiled-coil domain," *J. Mol. Biology* 312(1):221-228.
Arndt et al. (1998) "Factors influencing the dimer to monomer transition of an antibody single-chain Fv fragment," Biochemistry, 15;37(37):12918-26.
Bachman. (1987). "Derivations and Genotypes of Some Mutant Derivatives of *Esherichia coli* K-12," Chapter 72 in *Escherichia coli and Samonella typimurium Cellular and Molecular Biology*, vol. 2, American Society for Microbiology, Washington D.C., pp. 1190-1219.
Baldwin et al. (1986). "Monoclonal Antibodies in Cancer Treatment," *Lancet* 60:603-606.
Barbin et al. (Mar.-Apr. 2006). "Influence of Variable N-Glycosylation on the Cytolytic Potential of Chimeric CD19 Antibodies," *J. Immunother.* 29(2):122-133.
Barnes et al. (Mar. 1, 1980). "Methods for Growth of Cultured Cells in Serum-free Medium," *Anal. Biochem.* 102:255-270.
Bass et al. (1990). "Hormone Phage: An Enrichment Method for Variant Proteins With Altered Binding Properties," *Proteins* 8:309-314.
Bird et al. (Oct. 21, 1988). "Single-Chain Antigen-Binding Proteins," *Science* 242(4877):423-6.
Bird et al. (Apr. 28, 1989). "Single-Chain Antigen-Binding Proteins," *Science* 244(4903):409, Erratum.

(56) References Cited

OTHER PUBLICATIONS

Booy et al. (Mar.-Apr. 2006, e-pub. Mar. 24, 2006). "Monoclonal and Bispecific Antibodies as Novel Therapeutics," *Arch. Immunol. Ther. Exp.* 54:85-101.

Bothmann et al. (Jun. 2, 2000). "The Periplasmic *Escherichia coli* Peptidylprolyl cis,trans-Isomerase FkpA. I. Increased Functional Expression of Antibody Fragments With and Without cis-Prolines," *J. Biol. Chem.* 275(22):17100-17105.

Brorson et al., "Mutational Analysis of Avidity and Fine Specificity of Anti-Levan Antibodies," *J. Immunol.* 163:6694-6701 (1994).

Brummell et al., "Probing the combining site of an anti-carbohydrate antibody by saturation-mutagenesis: role of the heavy-chain CDR3 residues," *Biochemistry* 32(4):1180-1187 (1993).

Budtschanow et al. "System of Humoral Immunity Antibodies (Theme 2)," Guidance Manual for General Immunology, Twer (2008) p. 3, English Translation, 3 pages, (5 pages both English Equivalent and Russian Reference.

Burks et al., "In vitro scanning saturation mutagenesis of an antibody binding pocket," *PNAS* 94(2):412-417 (1997).

Burton. (1985). "Immunoglobulin G: Functional Sites," *Molec. Immunol.* 22(3):161-206.

Cao et al. (2003). "Bispecific Antibody Conjugates in Therapeutics," *Advanced Drug Delivery Reviews* 55:171-197.

Capel et al. (1994). "Heterogenity of Human IgG Fc Receptors," *Immunomethods* 4:25-34.

Carlsson et al. (Sep. 1, 1978). "Protein Thiolation and Reversible Protein-Protein Conjugation. N-Succinimidyl 3-(2-pyridyldithio)Propionate, A New Heterobifunctional Reagent," *Biochem. J.* 173:723-737.

Chari et al. (Jan. 1, 1992). "Immunoconjugates Containing Novel Maytansinoids: Promising Anticancer Drugs," *Cancer Research* 52:127-131.

Chen et al. (Nov. 5, 1999). "Selection and Analysis of an Optimized Anti-VEGF Antibody: Crystal Structure of an Affinity-Matured Fab in Complex With Antigen," *J. Mol. Biol.* 293(4):865-681.

Chen et al. (Jul. 9, 1999). "Chaperone Activity of DsbC," *J. Biol. Chem* 274(28):19601-19605.

Chothia et al. (1987). "Canonical Structures for the Hypervariable Regions of Immunoglobulins," *J. Mol. Biol.* 196:901-917.

Chow et al. (Jun. 30, 2000). "Studies on the Subsite Specificity of Rat Nardilysin (N-Arginine Dibasic Convertase)," *J. Biol. Chem.* 275(26):19545-19551.

Clynes et al. (Jan. 1998)."Fe Receptors are Required in Passive and Active Immunity to Melanoma," *Proc. Natl. Acad. Sci. USA* 95:652-656.

Coleman., "Effects of amino acid sequence changes on antibody-antigen interactions," *Research in Immunol.* 145(1):33-38, (1994).

Daëron. (1997). "Fe Receptor Biology," *Annu. Rev. Immunol.* 15:203-234.

Dall'acqua, W. et al. (1998). "Contribution of Domain Interface Residues to the Stability of Antibody $C_H3$ Domain Homodimers", *Biochemistry*, 37:9266-9273.

Davis et al. "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering Design & Selection* 23(4):195-202, (2010, e-pub. Feb. 4, 2010).

Davies et al. (1994). "'Camelising' Human Antibody Fragments: NMR Studies on VH Domains," *FEBS Letter* 339:285-290.

De Haas et al. (Oct. 1995). "Fcγ Receptors of Phagocytes," *J. Lab. Clin. Med.* 126(4):330-341.

Deyev et al. (2009). "Modern Technologies for Creating synthetic Antibodies for Clinical Application," *Acta Naturae* 1:32-50.

Dimmock, N.J. et al. (2004). " Valency of antibody binding to virions and its determination by surface plasmon resonance", *Rev. Med. Virol.*, 14:123-135.

Dooley et al. (2006). "Antibody Repertoire Development in Cartilaginous Fish," *Dev. Comp. Immunol.* 30(1-2):43-56.

Doronina et al. (Jul. 2, 2003, e-pub. Jun. 1, 2003). "Development of Potent Monoclonal Antibody Auristatin Conjugates for Cancer Therapy," *Nat. Biotechnol.* 21(7):778-784.

Dufner et al., "Harnessing phage and ribosome display for antibody optimization," *Trends Biotechol.* 24(11):523-29 (2006).

Eaton et al. (Dec. 30, 1986). "Construction and Characterization of an Active Factor VIII Variant Lacking the Central One-Third of the Molecule," *Biochemistry* 25(26):8343-8347.

Els Conrath et al. (Mar. 9, 2001). "Camel Single-Domain Antibodies as Modular Building Units in Bispecific and Bivalent Antibody Constructs," *Journal of Biological Chemistry* 276(19):7346-7350.

Fraker et al. (Feb. 28, 1978). "Protein and Cell Membrane Iodinations With a Sparingly Soluble Chloroamide, 1,3,4,6-Tetrachloro-3a,6a-Diphenylglycoluril," *Biochem. Biophys. Res. Commun.* 80(4):49-57.

Gadgil et al. (2006). "Identification of cysteinylation of a free cysteine in the Fab region of a recombinant monoclonal IgG1 antibody using lys-C limited proteolysis coupled with LC/MS analysis," *Analytical biochem.* 2006: 355:185-174.

Gazzano-Santoro et al. (1996). "A Non-Radiative Complement-Dependent Cytotoxicity Assay for Anti-CD20 Monoclonal Antibody," *J. Immunol Methods* 202:163.

Geoghegan et al. (1992). "Site-Directed Conjugation of Nonpeptide Groups to Peptides and Proteins via Periodate Oxidation of a 2-Amino Alcohol. Application Modification at N Terminator Serine," *Bioconjugate Chem.* 3(2):138-146.

Graham et al. (1977). "Characteristics of a Human Cell Line Transformed by DNA From Human Adenovirus Type 5," *J. Gen Virol.* 36:59-72.

Greenwood et al. "Structural Motifs Involved in Human IgG Antibody Effector Functions,". *Eur. J. Immunology* 23(5):1098-1104, (May 1993).

Grönwall C. et al. (Jun. 2008). "Generation of Affibody ligands binding interleukin-2 receptor alpha/CD25," *Biotechnol. Appl. Biochem.* 50(Pt. 2):97-112.

Guss et al. (1986). "Structure of the IgG-Binding Regions of Streptococcal Protein G," *EMBO J.* 5(7):1567-1575.

Guyer et al. (Aug. 1976). "Immunoglobulin Binding by Mouse Intestinal Epithelial Cell Receptors," *J. Immunol.* 117(2):587-593.

Ham et al. (1979). "Media and Growth Requirements," *Meth. Enz.* 58:44-93.

Hamers-Casterman et al. (1993). "Naturally occurring antibodies devoid of light chains," *Nature* 363:446-448.

Hara et al. (1996). "Overproduction of Penicillin-Binding Protein 7 Suppresses Thermosensitive Growth Defect at Low Osmolarity Due to an spr Mutation of *Escherichia coli*," *Microbial Drug Resistance* 2:63-72.

Hinman et al. (Jul. 15, 1993). "Preparation and Characterization of Monoclonal Antibody Conjugates of the Calicheamicins: A Novel and Potent Family of Antitumor Antibiotics," *Cancer Res.* 53:3336-3342.

Holliger et al. (Jul. 1993). "Diabodies': Small Bivalent and Bispecific Antibody Fragments," *Proc. Natl. Acad. Sci. USA* 90-6444-6448.

Holt et al. (Nov. 2003). "Domain Antibodies: Proteins for Therapy," *Trends Biotechnol.* 21(11):484-490.

Huston, J.S. et al. (1993). "Medical Applications of Single-Chain Antibodies," *Intern. Rev. Immunol.* 10(2-3):195-217.

Janeway. (Oct. 12, 1989). "Immunotherapy by Peptdes?," *Nature* 341:482-483.

Jang et al., "The structural basis for DNA binding by an anti-DNA autoantibody," *Mol. Immunol.* 35(18):1207-1217 (1998).

Johnson et al. (1991). "Construction of Single-Chain Fv Derivatives Monoclonal Antibodies and Their Production in *Escherichia coli*," *Methods Enzymol.* 203:88-98.

Johnson et al. (2003). Methods in Molecular Biology 248:11-25. (Lo, ed., Human Press, Totowa, NJ).

Joly et al. (Mar. 1998). "Overexpression of *Escherichia coli* Oxidoreductases Increases Recombinant Insulin-like Growth Factor-I Accumulation," *Proc. Natl. Acad. Sci. USA* 95-2773-2777.

Jones et al. (May 29, 1986). "Replacing the Complementarity—Determining Regions in a Human Antibody With Those From a Mouse," *Nature* 321:522-525.

(56) References Cited

OTHER PUBLICATIONS

Kim et al. (1994). "Localization of the Site of the Murine IgG1 Molecule that is Involved in Binding to the Murine Intestinal Fc Receptor," *Eur J Immunol.* 24:2429-2434.

Kobayshi et al. "Tryptophan H33 plays an important role in pyrimidine (6-4) pyrimidone photoproduct binding by a high-affinity antibody," *Protein Engineering* 12(10):879-844 (1999).

Kumar et al. (Nov. 10, 2000). "Molecular Cloning and Expression of the Fabs of Human Autoantibodies in *Escherichia coli*," *J. Biol. Chem.* 275(45):35129-35136.

Krugmann et al. "Structural Requirements for Assembly of Dimeric IgA Probed by Site-Directed Mutagenesis of J Chain and a Cysteine Residue of the α-chain CH2 Domain," *The Journal of Immunology* 159:244-249, (1997).

Lee et al. (1999). "Generation and Characterization of a Novel Single-Gene-Encoded Single-Chain Immunoglobulin Molecule With Antigen Binding Activity and Effector Functions" *Mol Immunol.* 36(1):61-71.

Lindmark et al. (1983). "Binding of Immunoglobulins to Protein A and Immunoglobulin Levels in Mammalian Sera," *J. Immunol. Meth.* 62:1-13.

Liu et al. (Aug. 6, 1996) "Eradication of Large Colon Tumor Xenografts by Targeted Delivery of Maytansinoids," *Proc. Natl. Acad. Sci. USA* 93:8618-8623.

Lode et al. (Jul. 15, 1998). "Targeted Therapy With a Novel Enediyene Antibiotic Calicheamicin θ$^I$ Effectively Suppresses Growth and Dissemination of Liver Metastases in a Syngeneic Model of Murine Neuroblastoma," *Cancer Res.* 58:2925-2928.

Lu et al. (2002). "Fab-scFv Fusion Protein: an Efficient Approach to Production of Bispecific Antibody Fragments" *J. Immunol Methods* 267(2):213-26.

Lu et al. (Jan. 23, 2004). "Simultaneous Blockage of Both the Epidermal Growth Factor Receptor and the Insulin-Like Growth Factor Receptor Signaling Pathways in Cancer Cells With a Fully Human Recombinant Bispecific Antibody" *J. Biol. Chem.* 279(4):2856-2865.

Lu et al. (2004. E-pub. Apr. 22, 2004). "The Effect of Variable Domain Orientation and Arrangement on the Antigen-Binding Activity of a Recombinant Human Bispecific Diabody" *Biochem. Biophys. Res. Commun.* 318(2):507-513.

Maccallum et al. (1996)."Antibody-antigen Interactions: Contact Analysis and Binding Site Topography," *J. Mol. Biol.* 262:732-745.

Malmborg et al. (1995). "BlAcore as a Tool in Antibody Engineering," *J. Immunol Methods* 183:7-13.

Mandler et al (Oct. 4, 2000). "Immunoconjugates of Geldanamycin and Anti-HER2 Monoclonal Antibodies: Antiproliferative Activity on Human Breast Carcinoma Cell Lines," *J. of the Nat. Cancer Inst.* 92(19):1573-1581.

Mandler et al. (May 15, 2000). "Synthesis and Evaluation of Antiproliferative Activity of a Geldanamycin-Herceptin Immunoconjugate," *Biorganic & Med. Chem. Letters* 10:1025-1028.

Mandler et al. (Jul.-Aug. 2002, e-pub. Jun. 19, 2002). "Modifications in Synthesis Strategy Improve the Yield and Efficacy of Geldanamycin-herceptin Immunoconjugates," *Bioconjugate Chem.* 13(4):786-791.

Mason et al. (2004). "Coiled Coil Domains: Stability, Specificity, and Biological Implications," *ChemBioChem* 5:170-176.

Mather (1980). "Establishment and Characterization of Two Distinct Mouse Testicular Epithelial Cell Lines," *Biol. Reprod.* 23:243-251.

Mather et al. (1982). "Culture of Testicular Cells in Hormone-supplemented Serum-Free Medium," *Annals N.Y. Aca. Sci.* 383:44-68.

McLean, G.R. et al. (2005). "A point mutation in the CH3 domain of human IgG3 inhibits antibody secretion without affecting antigen specificity", *Molecular Immunology*, 42:1111-1119.

Mirny, L. et al. (2001). "Protein Folding Theory: From Lattice to All-Atom Models", *Annu. Rev. Biophys. Biomol. Struct.*, 30-361-96.

Muller et al (Dec. 15, 2000). "Processing and Sorting of the Prohormone Convertase 2 Propeptide," *J. Biol. Chem.* 275(50):39213-39222.

Murakami et al. (1995). "Cell Cycle Regulation, Oncogenes, and Antineoplastic Drugs" Chapter 1 *in The Molecular Basis of Cancer*, Mendelsohn and Israel, Philadelphia, W.B. Saunders, Philadelphia pp. 3-17.

Muyldermas et al. (Apr. 2001). "Recognition of Antigens by Single-domain Antibody Fragments: the Superfluous Luxury of Paired Domains," *Trend Biochem. Sci.* 26(4):230-235.

Natsume et al. (Sep. 1, 2006). "Fucose Removal From Complex-type Oligosaccharide Enhances the Antibody-dependent Cellular Cytotoxicity of Single-gene-encoded Bispecific Antibody Comprising of Two Single-Chain Antibodies Linked to the Antibody Constant Region," *Journal of Biochemistry* 140(3):359-368.

Nicolaou et al. (1994). Calicheamicin θ$l_1$:A Rationally Designed Molecule with Extremely Potent and Selective DNA Cleaving Properties and Apoptosis Inducing Activity, *Agnew Chem. Intl. Ed. Engl.* 33(2):183-186.

Niculescu-Duvaz et al. (1997). "Antibody-Directed Enzyme Prodrug Therapy (ADEPT): A Review," *Adv. Drg. Del. Rev.* 26:151-172.

Nieri et al. (Feb. 1, 2009). "Antibodies for Therapeutic Uses and the Evolution of Biotechniques," *Current Med. Chem.* 16(6):753-779.

Nilsson et al. (1987). "A synthetic IgG-binding domain based on staphylococcal protein A," *Prot. Eng.* 1:107-133.

Nord et al. (1995). "A combinatorial library of an α-helical bacterial receptor domain," *Prot. Eng.* 8:601-608.

Nord et al. (1997). "Binding proteins selected from combinatorial libraries of an α-helical bacterial receptor domain," *Nat. Biotech.* 15:772-777.

Novotný, J. et al. (1985). "Structural invariants of antigen binding: Comparison of immunoglobulin $V_L$-$V_H$ and $V_L V_L$ domain dimmers", *Proc. Natl. Acad. Sci. USA*, 82:4592-4596.

Offner et al. (Jan. 25, 1991). "T Cell Receptor Peptide Therapy Triggers Autoregulation of Experimental Encephalomyelitis," *Science* 251:430-432.

O'Shea et al. "Peptide 'Velcro': design of a heterodimeric coiled coil," *Current Biology* 3(10):658-667, (1993).

Pan, Q. et al. "Blocking Neuropilin-1 Function Has an Additive Effect with nti-VEGF to Ihibit Tumor Growth," *Cancer Cell* 11:53-67, (Jan. 2007).

Pettit et al. (Jul.-Aug. 1981). "Marine Animal Biosynthetic Constituents for Cancer Chemotherapy," *J. Nat. Prod.* 44:482-485.

Pettit et al. (1997). "The Dolastatins," *Fortschr. Chem. Org. Naturst.* 70:1-79.

Pettit et al. (1998). "Antineoplastic Agents 360. Synthesis and Cancer Cell Growth Inhibitory Studies of Dolastatin 15 Structural Modifications," *Anti-Cancer Drug Design* 13:47-66.

Pettit et. al. (Nov. 1998). "Specific Activities of Dolastatin 10 and Peptide Derivatives Against *Cryptococcus neoformans*," *Antimirob. Agents Chemother.* 42(11):2961-2965.

Pleass et al. "Identification of Residues in the CH2/CH3 Domain Interface of IgA Essential for Interaction With the Human fcα Receptor (Fcα R) CD89," *The Journal of Biology Chemistry* 274(33):23508-23514, (Aug. 13, 1999).

Pluckthun. (1994). "Antibodies from *Escherichia coli*" Chapter 11 *in The Pharmacology of Monoclonal Antibodies: Handbook of Phannacology*, Rosenberg and Moore, eds., Berlin:Springer-Verlag, vol. 113, pp. 269-315.

Poncet (1999). "The Dolastatins, A Family of Promising Antineoplastic Agents," *Curr. Pharm. Des.* 5:139-162.

Presta (1992). "Antibody Engineering," *Curr. Op. Struct. Biol.* 2:593-596.

Presta et al. (Sep. 1, 1993). "Humanization of an Antibody Directed Against IgE," *J. Immunol.* 151(5):2623-2632.

Proba et al. (Jul. 4, 1995). "Functional Antibody Single-Chain Fragments From the Cytoplasm of *Escherichia coli*: Influence of Thioredoxin Reductase (TrxB)," *Gene* 159:203-207.

Ramm et al. (Jun. 2, 2001). "The Peroplasmic *Escherichia coli* Peptidylproly cis,trans-Isomerase FkpA," *J. Biol. Chem.* 275(22):17106-17113.

(56) References Cited

OTHER PUBLICATIONS

Ravetch et al. (1991). "Fc Receptors," *Annu. Rev. Immunol.* 9:457-492.
Reiter et al. (1994). "Stabilization of the Fv Fragments in Recombinant Immunotoxins by Disulfide Bonds Engineered into Conserved Framework Regions," *Biochemistry* 33(18):5451-5449.
Reiter et al. (Jul. 15, 1994). "Improved Binding and Antitumor Activity of a Recombinant Anti-erbB2 Immunotoxin by Disulfide Stabilization of the Fv Fragment," *J. Biol. Chem.* 269(28):18327-18331.
Reiter et al. (May 1994). "Engineering Interchain Disulfide Bonds Into Conserved Framework Regions of Fv Fragments: Improved Biochemical Characteristics of Recombinant Immunotoxins Containing Disulfide-Stabilized Fv," *Protein Eng.* 7(5):697-704.
Roitt A. et al., (2000), "Multispecific Antibodies Comprising Full Length Antibodies and Single Chain Fab Fragments," *Immunology*, English Translation, Moscow:Mir, pp. 388-389.
Rowland et al (1986). "Drug Localisation and Growth Inhibition Studies of Vindesine-Monoclonal Anti-CEA Conjugates in a Human Tumour Xenograft," *Cancer Immunol. Immunother.* 21:183-187.
Ruppert et al. (Mar. 11, 1993). "Cloning and Expression of Human $TAF_{II}250$: a TBP-Associated Factor Implicated in Cell-Cycle Regulation," *Nature* 362:175-179.
Santos et al. (Oct. 1999) "Generation and Characterization of a Single Gene-Encoded Single-Chain-tetravalent Antitumor Antibody" *Clinical Cancer Research* 5(10 Suppl):3118s-3123s.
Schirrmann et al. (Jan./Feb. 2010). "Oligomeric Forms of Single Chain Immunoglobulin (sclgG)," *Landes Bioscience* 2(1):73-76.
Schoonjans et al. (2000). "Efficient Heterodimerization of Recombinant Bi- and Trispecific Antibodies" *Bioseparation* 9(3):179-183.
Schröder et al. (1965). "III. Formation of the Peptide Bond," *The Peptides*, vol. 1, Academic Press, New York, New York, pp. 76-136.
Shechter et al. (1976) "Selective Chemical Cleavage of Tryptophanyl Peptide Bonds by Oxidative Chlorination With N-Chlorosuccinimide," *Biochemistry* 15(23):5071-5075.
Sheriff et al. (1996). "Redefining the minimal antigen-binding fragment," *Nature Struct. Biol.* 3:733-736.
Siebenlist et al. (Jun. 1980). "*E. coli* RNA Polymerase Interacts Homologously with Two Different Promoters," *Cell* 20:269-281.
Sims et al. (Aug. 15, 1993). "A Humanized CD18 Antibody Can Block Function Without Cell Destruction," *J. Immunol.* 151(4):2296-2308.
Smith-Gill et al. (Dec. 15, 1987). "Contributions of Immunoglobulin Heavy and Light Chain to Antibody Specificity for Lysozyme and Two Haptens," *J. Immunol.* 139(12):4135-4144.
Song et al. (2000). "Light Chain of Natural Anibody Plays a Dominant Role in Protein Antigen Binding," *Biochem. Biophys. Res. Comm.* 268(2):390-394.
Steiner. (1991). "The Biosynthesis of Biologically Active Peptides: A Perspective," Chapter 1 in *Peptide Biosynthesis and Processing*, Fricker ed., CRC Press, Boca Raton, FL, pp. 1-16.
Stella et al. (1985). "Prodrugs: A Chemical Approach to Target Drug Delivery" *Directed Drug Delivery*, Borchardt et al (ed.), Human Press, pp. 247-267.
Stites et al. (1994). "Immunoglobulin Protiens," Chapter 6 in *Basic Clinical Immunology*, $8^{th}$ Edition, Appleton & Lange, Norwalk, CT, p. 71.
Stork et al. "A novel tri-functional antibody fusion protein with improved pharmacokinetic properties generated by fusing a bispecific single-chain diabody with an albumin-binding domain from streptococcal protein G," *Protein Eng. Des. Sel.* 20(11):569-576, (Nov. 2007, e-pub. Nov. 3, 2007).
Syrigos et al. (1999). "Antibody Directed Enzyme Prodrug Therapy (ADEPT): A Review of the Experimental and Clinical Considerations," *Anticancer Research* 19:605-614.
Tao et al. "The Differential Ability of Human IgG1 and IgG4 to Activate Complement is Determined by the COOH-terminal Sequence of the $C_H2$ Domain," *J. Exp. Med* 173:1025-1028, (Apr. 1991).

Thie et al. (Jul. 22, 2009). "Multimerization Domains for Antibody Phage Display and Antibody Production," *New Biotech*. 26(6):314-321.
Thorpe. (1985) "Antibody Carriers of Cyotoxic Agents in Cancer Therapy: A Review," in *A Monoclonal Antibodies 84: Biological and Clinical Applications*, A. Pinchera et al (eds) pp. 475-506.
Torres, M. et al. (2005). "Variable-Region-Identical Antibodies Differing in Isotype Demonstrate Differences in Fine Specificity and Idiotype", *The Journal of Immunology*, 174:2132.
Urlaub et al. (Jul. 1980). "Isolation of Chinese Hamster Cell Mutants Deficient in Dihydrofolate Reductase Activity," *Proc. Natl. Acad Sci USA* 77(7):4216-4220.
Verhoeyen et al. (Mar. 25, 1988). "Reshaping Human Antibodies: Grafting an Antilysozyme Activity," *Science* 239:1534-1536.
Vitetta et al. (Novmeber 20, 1987). "Redesigning Nature's Poisons to Create Anti-tumor Reagents," *Science* 238:1098-1104.
Walker et al. (Jun. 5, 2009, e-pub. Apr. 16, 2009). "Efficient Recovery of High-Affinity Antibodies From a Single-Chain Fab Yeast Display Library," *J. Mol. Biol.* 389(2):365-375.
Ward et al. (Oct. 12, 1989). "Binding Activities of a Repertoire of Single Immunoglobulin Variable Domains Secreted From *Escherichia coli*," *Nature* 341:544-546.
Wilman. (1986). "Prodrugs in Cancer Chemotherapy," *Biochemical Society Transactions* 14:37-382, $615^{th}$ Meeting Belfast, 8 pages.
Woyke et al. (Dec. 2001). "In Vitro Activities and Postantifungal Effects of the Potent Dolastatin10 Derivative Auristatin PHE," *Antimicrob. Agents and Chemother.* 45(12):3580-3584.
Wrank et al. (Dec. 21, 2012). "Luz-Y: A Novel Platform for the Mammalian Cell Production of Full-length IgG Bispeciic Antibodies," *Journal of Biological Chemistry* 287(52):43331-43339.
Xu et al. (2000). "Diversity in the CDR3 region of V(H) is sufficient for most antibody specificities," *Immunity* 13:37-45.
Yaniv. (May 6, 1982). "Enhancing Elements for Activation of Eukaryotic Promoters," *Nature* 297:17-18.
Zapata et al. (1995). "Engineering Linear F(ab')$_2$ Fragments for Efficient Production in *Escherichia coli* and Enhanced Antiproliferative Activity," *Protein Eng.* 8(10):1057-1062.
Zhu et al. (1997). "Remodeling Domain Interfaces to Enhance Heterodimer Formation," *Protein Science* 6:781-788.
International Search Report mailed on Aug. 6, 2013, for PCT Application No. PCT/US2013/025365, filed Feb. 8, 2013, 6 pages.
Written Opinion mailed on Aug. 6, 2013, for PCT Application No. PCT/US2013/025365, filed Feb. 8, 2013, 9 pages.
Extended European Search Report mailed on Aug. 5, 2013, for European Patent Application No. 10817575.3, eleven pages.
International Preliminary Report on Patentability for PCT/EP2011/054505, mailed on Oct. 2, 2012, filed on Mar. 24, 2011, 8 pages.
International Preliminary Report on Patentability mailed on Aug. 21, 2014, for PCT Patent Application No. PCT/US2013/025365, filed on Feb. 8, 2013, 11 pages.
International Search Report mailed on Jun. 15, 2011 for PCT Patent Application No. PCT/US2010/002546 filed on Sep. 16, 2010, five pages.
International Search Report for PCT/EP2011/054505 mailed on Jun. 28, 2011, filed on Mar. 24, 2011, 7 pages.
Written Opinion of the International Searching Authority mailed on Jun. 15, 2011 for PCT Patent Application No. PCT/US2010/002546 filed on Sep. 16, 2010, seven pages.
Russian Office Action dated Apr. 18, 2013, for Russian Patent Application No. 2010 129 539, 3 pages.
Russian Office Action dated Oct. 8, 2014, for Russian Patent Application No. 2012 100 865, 3 pages.
U.S. Appl. No. 14/735,024, filed Jun. 9, 2015 for Christensen et al.
U.S. Appl. No. 14/551,957, filed Nov. 24, 1014 for Castoldi et al.
Anthony et al. "A recombinant IgG Fc that recapitulates the antiinflammatory activity of IVIG," *Science* 320(5874):373-376, (2008).
Armour et al. "Recombinant human IgG molecules lacking Fcγ receptor I binding and monocyte triggering activities," *Eur. J. Immunol.* 29:2613-2624, (1999).
Bendig. "Humanization of Rodent Monoclonal Antibodies by CDR Grafting," *Methods: A companion to Methods in Enzymology* 8:83-93 (1995).

(56) References Cited

OTHER PUBLICATIONS

Carter. "Potent antibody therapeutics by design," *Nature Reviews Immunology* 6:343-357, (2006).
Chames et al. "Bispecific antibodies for cancer therapy," *Current Opinion in Drug Discovery & Development*, 12(2):276-283, (2009).
Chan et al. "Therapeutic antibodies for autoimmunity and inflammation," *Nat. Rev. Immunol.* 10(5):301-316, (2010).
Charlton., In: Methods in Molecular Biology, vol. 248, Lo, B.K.C. (ed.), Humana Press, Totowa, NJ, pp. 245-254, (2003).
Chin et al. "Addition of p-azido-L-phenylalanine to the genetic code of *Escherichia coli*," *J. Am. Chem. Soc.*, 124(31):9026-9027, (2002).
Chin et al. "In vivo photocrosslinking with unnatural amino Acid mutagenesis," *ChemBioChem*. 3(11):1135-1137, (2002).
Chin et al. "Addition of a photocrosslinking amino acid to the genetic code of *Escherichia coli*," *Proc. Natl. Acad. Sci. U.S.A.*, 99(17):11020-11024, (2002).
Clancy et al. "Sortase transpeptidases: insights into mechanism, substrate specificity, and inhibition," *Biopolymers*, 94(4):385-396, (2010).
Cruse, J.M., et al., 2nd ed., CRC Press, p. 37, 316-317, (2003).
Friend et al. (1999). "Phase I study of an engineered aglycosylated humanized CD3 antibody in renal transplant rejection," *Transplantation*, 68(11):1632-1637, (1999).
Gerngross. "Advances in the production of human therapeutic proteins in yeasts and filamentous fungi," *Nat. Biotech.* 22:1409-1414, (2004).
Hatfield et al. "Antiangiogenic therapy in acute myelogenous leukemia: targeting of vascular endothelial growth factor and interleukin 8 as possible antileukemic strategies," *Curr. Cancer Drug Targets* 5(4):229-248, (2005).
Herberman, "Immunodiagnosis of Cancer", in Fleisher (ed.), "The Clinical Biochemistry of Cancer," p. 347, American Association of Clinical Chemists (1979).
Huber et al. "Crystallographic structure studies of an IgG molecule and an Fc fragment", *Nature*, 264:415-420, (1976).
Hudson et al. "Engineered antibodies," *Nat. Med.* 9:129-134, (2003).
Ilangovan et al. "Structure of sortase, the transpeptidase that anchors proteins to the cell wall of *Staphylococcus aureus*," *Proc. Natl. Acad. Sci. U.S.A.* 98(11):6056-6061, (2001).
Jefferis et al. "Interaction sites on human IgG-Fc for FcγR: current models," *Immunol. Lett.*, 82:57-65, (2002).
Jiang et al. "Advances in the assessment and control of the effector functions of therapeutic antibodies," *Nat. Rev. Drug Discov.*, 10(2):101-111, (2011).
Labrijn et al. "Species-Specific Determinants in the IgG CH3 Domain Enable Fab-Arm Exhange by Affecting the Noncovalent CH3-CH3 Interaction Strength," *The Journal of lmmmunology* 187:3238-3246, (2011, e-pub. Aug. 12, 2011).
Levary et al. "Protein-Protein fusion catalyzed by sortase A," *PLOS One* 6:e18342.1-e18342.6, (2011).
Li et al. "Optimization of humanized IgGs in glycoengineered Pichia pastoris," *Nat. Biotech.* 24:210-215, (2006).
Madej et al. "Engineering of an anti-epidermal growth factor receptor antibody to single chain format and labeling by sortase A-mediated protein ligation," *Biotechnology and Bioengineering* 109(6):1461-1470, (2012).
Mallender et al "Comparative Properties of the Single Chain Antibody and Fv Derivateives of mAb 4-4-20. Relationship Between Interdomain Interactions and the High Affinity for Fluorescein Ligand," *Journal of Biological Chemistry* 271(10):5338-5346, (Mar. 8, 1996).
Mizukami et al. "Induction of interleukin-8 preserves the angiogenic response in HIF-1alpha-deficient colon cancer cells," *Nat. Med.*, 11(9):992-997, (2005).
Möhlmann et al. "In vitro sortagging of an antibody fab fragment: overcoming unproductive reactions of sortase with water and lysine side chains," *Chembiochem: A European Journal of Chemical Biology* 12(11):1774-1780, (2011).

Noren et al. "A General Method for Site-Specific Incorporation of Unnatural Amino Acids into Proteins," *Science*, 244:182-188, (1989).
Novellino et al. "A listing of human tumor antigens recognized by T cells: Mar. 2004 update," *Cancer Immunol. Immunother*, 54(3):187-207, (2005).
Parmiani et al. "Unique human tumor antigens: immunobiology and use in clinical trials," *J. Immunol.* 178(4):1975-1979, (2007).
Paul. "Structure and Function of Immunoglobulins," Chapter 9 in *Fundamental Immunology*, Third Edition, Raven Press, New York, New York, pp. 292-295, (1993).
Popp et al. "Making and breaking peptide bonds: protein engineering using sortase," *Angewandte Chemie*, 50(22):5024-5032, (2011).
Presta. "Molecular engineering and design of therapeutic antibodies," *Current Opinion in Immunology* 20:460-470, (2008).
Ren et al. "Macrophage migration inhibitory factor stimulates angiogenic factor expression and correlates with differentiation and lymph node status in patients with esophageal squamous cell carcinoma," *Ann. Surg.* 242:55-63, (2005).
Routledge et al. "The effect of aglycosylation on the immunogenicity of a humanized therapeutic CD3 monoclonal antibody," *Transplantation*, 60(8):847-853, (1995).
Roux et al. "Comparisons of the ability of human IgG3 hinge mutants, IgM, IgE, and IgA2, to form small immune complexes: a role for flexibility and geometry," *J. Immunol.*, 161(8):4083-4090, (1998).
Sakamoto et al. "Enzyme-Mediated Site-Specific Antibody-Protein Modification Using a ZZ Domain as a Linker,"*BioConjugate Chem.* . . 21 :2227-2293 (2010, e-pub. Nov. 11, 2010).
Salfeld. "Isotype Selection in Antibody Engineering," *Nat. Biotechnol.* 25(12):1369-1372, (Dec. 2007).
Sensi et al. "Unique tumor antigens: evidence for immune control of genome integrity and immunogenic targets for T cell-mediated patient-specific immunotherapy," *Clin. Cancer Res.* 12(17):5023-5032, (2006).
Sondermann et al. "The 3.2-A crystal structure of the human IgG1 Fc fragment-FcγRIII complex," *Nature*, 406:267-273, (2000).
Strop et al. "Generating Bispecific Human IgG1 and IgG2 Antibodies from Any Antibody Pair," *Journal of Molecular Biology*, 420(3):204-219, (2012).
Ta, et al. "Enzymatic Single-Chain Antibody Tagging a Universal Approach to Targeted Molecular Imaging and Cell Homing in Cardiovascular Disease," *Circulation Research*, 109(4):365-373, (2011).
Thies et al. "Folding and association of the antibody domain CH3: prolyl isomerization preceeds dimerization," *J. Mol. Biol.*, 293:67-79, (1999).
Ton-That et al. "Purification and characterization of sortase, the transpeptidase that cleaves surface proteins of *Staphylococcus aureus* at the LPXTG motif," *Proc. Natl. Acad. Sci. U.S.A.*, 96(22):12424-12429, (1999).
Tsukiji S. et al. "Sortase-Mediated Ligation: A Gift from Gram-Positive Bacteria to Protein Engineering," *Chembiochem*, 10(5):787-798, (2009).
Vallböhmer et al. "Molecular determinants of cetuximab efficacy," *J Clin. Oncol.*, 23(15):3536-3544, (2005).
Wagner et al. "Bispecific antibody generated with sortase and click chemistry has broad antiinfluenza virus activity," *Proc. Natl. Acad. Sci. USA* 111:16820-16825, (Nov. 25, 2014).
Wang et al. "Expanding the genetic code," *Chem. Commun* (*Camb.*), 7:1-11, (2002).
Ward et al. "The effector functions of immunoglobulins: implications for therapy," *Ther. Immunol.*, 2:77-94, (1995).
Witte et al. "Preparation of unnatural N-to-N and C-to-C protein fusions," *Proceedings of the National Academy of Sciences of the United States of America*, 109(30):11993-11998, (2012).
Yazaki et al. Methods in Molecular Biology, vol. 248, Lo, B.K.C. (ed.), Humana Press, Totowa, NJ (2004), pp. 255-268, (2004).
International Search Report mailed on Aug. 5, 2014, for PCT Patent Application No. PCT/EP2013/063258, filed on Jun. 25, 2013, seven pages.

(56) References Cited

OTHER PUBLICATIONS

Written Opinion of the International Searching Authority mailed on Aug. 5, 2014, for PCT Patent Application No. PCT/EP2013/063258, filed on Jun. 25, 2013, seven pages.
U.S. Appl. No. 14/579,165, filed Dec. 22, 2014, by Dieter et al.
U.S. Appl. No. 14/579,192, filed Dec. 22, 2014, by Sebastian et al.
ALT et al. "Novel Tetravalent and Bispecific IgG-Like Antibody Molecules Combining Single-chain Diabodies With the Immunoglobulin y1 Fc or CH3 Region," *FEBS Lett.* 454(1-2):90-94, (Jul. 2, 1999).
Chen et al. "Improved Variants of SrtA for Site-Specific Conjugation on Antibodies and Proteins With High Efficiency," *Scientific Reports* 6(31899):1-12, (Aug. 18, 2016).
Rose et al. "Quantitative Analysis of the Interaction Strength and Dynamics of Human IgG4 Half Molecules by Native Mass Spectrometry," Structure 19:1274-1282, (Sep. 7, 2011).

\* cited by examiner

Co-expression of separate dsFv modules

FIG. 4C

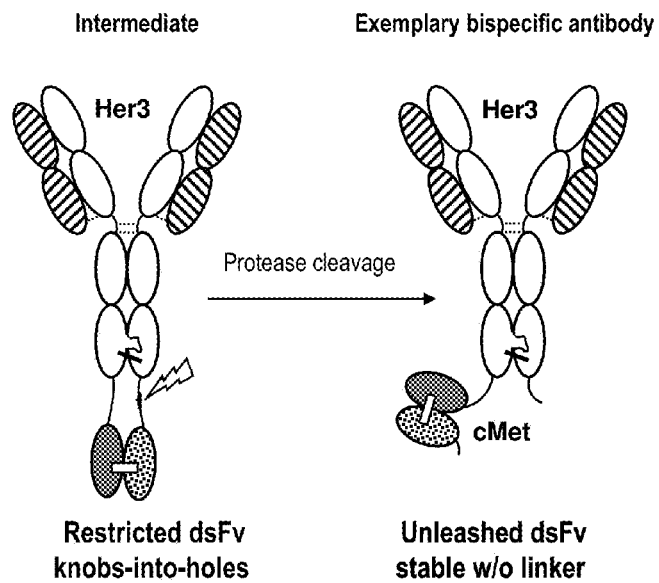

Intermediate
Her3
Protease cleavage
Restricted dsFv
knobs-into-holes

Exemplary bispecific antibody
Her3
cMet
Unleashed dsFv
stable w/o linker

FIG. 4D

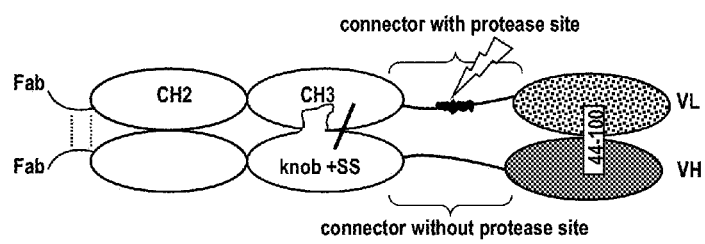

connector with protease site
Fab — CH2 — CH3 — VL
Fab — knob +SS — VH
connector without protease site

| | |
|---|---|
| Connector w/o protease site | CH3 (knob) (GGGGS)2-GGGGSGGGGS(GGGGS)2 VHcys44 |
| Prescission recognition site | CH3 (hole) (GGGGS)2-GLEVLFQ↯GPS(GGGGS)2 VLcys100 |
| Furin recognition site | CH3 (hole) (GGGGS)2-GQSSRHRR↯AL(GGGGS)2 VLcys100 |

US 9,879,095 B2

SEQUENCE LISTING

<160> NUMBER OF SEQ ID NOS: 24

<210> SEQ ID NO 1
<211> LENGTH: 597
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: Her3/MetSS_KHSS_FS1 - HC1 (SS_KnobsHC1_VHcMet)

<400> SEQUENCE: 1
```

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Ser Asn Ser Tyr Ala Pro Ser Leu
    50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
            435                 440                 445

Gly Gly Gly Gly Ser Gly Gly Gly Gly Ser Gly Gly Gly Gly Ser Gly
450                 455                 460

Gly Gly Gly Ser Gly Gly Gly Gly Ser Gly Gly Gly Gly Ser Glu Val
465                 470                 475                 480

Gln Leu Val Glu Ser Gly Gly Gly Leu Val Gln Pro Gly Gly Ser Leu
            485                 490                 495

Arg Leu Ser Cys Ala Ala Ser Gly Tyr Thr Phe Thr Ser Tyr Trp Leu
            500                 505                 510

His Trp Val Arg Gln Ala Pro Gly Lys Cys Leu Glu Trp Val Gly Met
            515                 520                 525

Ile Asp Pro Ser Asn Ser Asp Thr Arg Phe Asn Pro Asn Phe Lys Asp
530                 535                 540

Arg Phe Thr Ile Ser Ala Asp Thr Ser Lys Asn Thr Ala Tyr Leu Gln
545                 550                 555                 560

Met Asn Ser Leu Arg Ala Glu Asp Thr Ala Val Tyr Tyr Cys Ala Thr
            565                 570                 575

Tyr Arg Ser Tyr Val Thr Pro Leu Asp Tyr Trp Gly Gln Gly Thr Leu
            580                 585                 590

Val Thr Val Ser Ser
            595

<210> SEQ ID NO 2
<211> LENGTH: 592
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Her3/MetSS_KHSS_FS1 - HC2 (SS_HolesHC2 _
      VLcMet_FS1)

<400> SEQUENCE: 2

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Ser Asn Ser Tyr Ala Pro Ser Leu
    50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
```

```
            115                 120                 125
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gly Gly Gly Ser Gln Ser Ser Arg His
    450                 455                 460

Arg Arg Ala Leu Gly Gly Gly Ser Gly Gly Gly Gly Ser Asp Ile
465                 470                 475                 480

Gln Met Thr Gln Ser Pro Ser Ser Leu Ser Ala Ser Val Gly Asp Arg
                485                 490                 495

Val Thr Ile Thr Cys Lys Ser Ser Gln Ser Leu Leu Tyr Thr Ser Ser
            500                 505                 510

Gln Lys Asn Tyr Leu Ala Trp Tyr Gln Gln Lys Pro Gly Lys Ala Pro
        515                 520                 525

Lys Leu Leu Ile Tyr Trp Ala Ser Thr Arg Glu Ser Gly Val Pro Ser
    530                 535                 540
```

```
Arg Phe Ser Gly Ser Gly Ser Gly Thr Asp Phe Thr Leu Thr Ile Ser
545                 550                 555                 560

Ser Leu Gln Pro Glu Asp Phe Ala Thr Tyr Tyr Cys Gln Gln Tyr Tyr
                565                 570                 575

Ala Tyr Pro Trp Thr Phe Gly Cys Gly Thr Lys Val Glu Ile Lys Arg
            580                 585                 590
```

<210> SEQ ID NO 3
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Her3/MetSS_KHSS_FS1 - LC (Her3clone29_KO1_LC)

<400> SEQUENCE: 3

```
Asp Ile Gln Met Thr Gln Thr Thr Ser Ser Leu Ser Ala Ser Leu Gly
1               5                   10                  15

Asp Arg Val Thr Ile Ser Cys Arg Ala Arg Gln Asp Ile Ser Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 4
<211> LENGTH: 597
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Her3/MetSS_KHSS_FS2 - HC1 (SS_KnobsHC1_VHcMet)

<400> SEQUENCE: 4

```
Asp Val Gln Leu Gln Glu Ser Gly Pro Gly Leu Val Lys Pro Ser Gln
```

-continued

```
1               5                   10                  15
Ser Leu Ser Leu Thr Cys Ser Val Thr Gly Tyr Ser Ile Thr Ser Ala
                20                  25                  30
Tyr Tyr Trp Asn Trp Ile Arg Gln Phe Pro Gly Asn Lys Leu Glu Trp
                35                  40                  45
Met Gly Tyr Ile Ser Tyr Gly Ser Asn Ser Tyr Ala Pro Ser Leu
                50                  55                  60
Lys Asn Arg Phe Ser Ile Thr Arg Asp Thr Ser Lys Asn Gln Phe Phe
65                      70                  75                  80
Leu Lys Leu Asn Ser Val Thr Thr Glu Asp Thr Ala Thr Tyr Tyr Cys
                85                  90                  95
Ala Arg Glu Ser Asp Tyr Ala Tyr Phe Asp Tyr Trp Gly Gln Gly Thr
                100                 105                 110
Thr Leu Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
                130                 135                 140
Cys Leu Val Lys Asp Tyr Phe Pro Glu Pro Val Thr Val Ser Trp Asn
145                     150                 155                 160
Ser Gly Ala Leu Thr Ser Gly Val His Thr Phe Pro Ala Val Leu Gln
                165                 170                 175
Ser Ser Gly Leu Tyr Ser Leu Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
                210                 215                 220
His Thr Cys Pro Pro Cys Pro Ala Pro Glu Leu Leu Gly Gly Pro Ser
225                     230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
                290                 295                 300
Ser Val Leu Thr Val Leu His Gln Asp Trp Leu Asn Gly Lys Glu Tyr
305                     310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Cys Arg Asp Glu Leu Thr Lys Asn Gln Val Ser Leu Trp Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                     390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
```

```
Leu His Asn His Tyr Thr Gln Lys Ser Leu Ser Leu Ser Pro Gly Lys
            435                 440                 445

Gly Gly Gly Gly Ser Gly Gly Gly Gly Ser Gly Gly Gly Gly Ser Gly
        450                 455                 460

Gly Gly Gly Ser Gly Gly Gly Ser Gly Gly Gly Gly Ser Gly Glu Val
465                 470                 475                 480

Gln Leu Val Glu Ser Gly Gly Gly Leu Val Gln Pro Gly Gly Ser Leu
                485                 490                 495

Arg Leu Ser Cys Ala Ala Ser Gly Tyr Thr Phe Thr Ser Tyr Trp Leu
            500                 505                 510

His Trp Val Arg Gln Ala Pro Gly Lys Cys Leu Glu Trp Val Gly Met
        515                 520                 525

Ile Asp Pro Ser Asn Ser Asp Thr Arg Phe Asn Pro Asn Phe Lys Asp
    530                 535                 540

Arg Phe Thr Ile Ser Ala Asp Thr Ser Lys Asn Thr Ala Tyr Leu Gln
545                 550                 555                 560

Met Asn Ser Leu Arg Ala Glu Asp Thr Ala Val Tyr Tyr Cys Ala Thr
                565                 570                 575

Tyr Arg Ser Tyr Val Thr Pro Leu Asp Tyr Trp Gly Gln Gly Thr Leu
            580                 585                 590

Val Thr Val Ser Ser
            595

<210> SEQ ID NO 5
<211> LENGTH: 592
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Her3/MetSS_KHSS_FS2 - HC2 (SS_HolesHC2_
      VLcMet_FS2)

<400> SEQUENCE: 5

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Ser Asn Ser Tyr Ala Pro Ser Leu
    50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

```
              165                 170                 175
Ser Ser Gly Leu Tyr Ser Leu Ser Ser Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
            355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

Gly Gly Gly Gly Ser Gly Gly Gly Gly Ser Leu Ser His Arg Ser
450                 455                 460

Lys Arg Ser Leu Gly Gly Gly Ser Gly Gly Gly Gly Ser Asp Ile
465                 470                 475                 480

Gln Met Thr Gln Ser Pro Ser Ser Leu Ser Ala Ser Val Gly Asp Arg
                485                 490                 495

Val Thr Ile Thr Cys Lys Ser Ser Gln Ser Leu Leu Tyr Thr Ser Ser
            500                 505                 510

Gln Lys Asn Tyr Leu Ala Trp Tyr Gln Gln Lys Pro Gly Lys Ala Pro
            515                 520                 525

Lys Leu Leu Ile Tyr Trp Ala Ser Thr Arg Glu Ser Gly Val Pro Ser
            530                 535                 540

Arg Phe Ser Gly Ser Gly Ser Gly Thr Asp Phe Thr Leu Thr Ile Ser
545                 550                 555                 560

Ser Leu Gln Pro Glu Asp Phe Ala Thr Tyr Tyr Cys Gln Gln Tyr Tyr
                565                 570                 575

Ala Tyr Pro Trp Thr Phe Gly Cys Gly Thr Lys Val Glu Ile Lys Arg
            580                 585                 590
```

<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Her3/MetSS_KHSS_FS2 - LC (Her3clone29_KO1_LC)

<400> SEQUENCE: 6

```
Asp Ile Gln Met Thr Gln Thr Thr Ser Ser Leu Ser Ala Ser Leu Gly
1               5                   10                  15

Asp Arg Val Thr Ile Ser Cys Arg Ala Arg Gln Asp Ile Ser Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 7
<211> LENGTH: 597
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Her3/MetSS_KHSS_PreSci - HC1 (SS_KnobsHC1_VHcMet)

<400> SEQUENCE: 7

```
Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45
```

```
Met Gly Tyr Ile Ser Tyr Gly Gly Ser Asn Ser Tyr Ala Pro Ser Leu
    50                  55                  60
Lys Asn Arg Phe Ser Ile Thr Arg Asp Thr Ser Lys Asn Gln Phe Phe
 65                  70                  75                  80
Leu Lys Leu Asn Ser Val Thr Thr Glu Asp Thr Ala Thr Tyr Tyr Cys
                 85                  90                  95
Ala Arg Glu Ser Asp Tyr Ala Tyr Phe Asp Tyr Trp Gly Gln Gly Thr
            100                 105                 110
Thr Leu Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Cys Arg Asp Glu Leu Thr Lys Asn Gln Val Ser Leu Trp Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
Gly Gly Gly Gly Ser Gly Gly Gly Ser Gly Gly Gly Gly Ser Gly
    450                 455                 460
Gly Gly Gly Ser Gly Gly Gly Gly Ser Gly Gly Gly Gly Ser Glu Val
```

```
                465                 470                 475                 480
        Gln Leu Val Glu Ser Gly Gly Leu Val Gln Pro Gly Gly Ser Leu
                            485                 490                 495

Arg Leu Ser Cys Ala Ala Ser Gly Tyr Thr Phe Thr Ser Tyr Trp Leu
                        500                 505                 510

His Trp Val Arg Gln Ala Pro Gly Lys Cys Leu Glu Trp Val Gly Met
                    515                 520                 525

Ile Asp Pro Ser Asn Ser Asp Thr Arg Phe Asn Pro Asn Phe Lys Asp
        530                 535                 540

Arg Phe Thr Ile Ser Ala Asp Thr Ser Lys Asn Thr Ala Tyr Leu Gln
        545                 550                 555                 560

Met Asn Ser Leu Arg Ala Glu Asp Thr Ala Val Tyr Tyr Cys Ala Thr
                        565                 570                 575

Tyr Arg Ser Tyr Val Thr Pro Leu Asp Tyr Trp Gly Gln Gly Thr Leu
                    580                 585                 590

Val Thr Val Ser Ser
                    595

<210> SEQ ID NO 8
<211> LENGTH: 592
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Her3/MetSS_KHSS_PreSci - HC2 (SS_HolesHC2 _
      VLcMet_PreSci)

<400> SEQUENCE: 8

Asp Val Gln Leu Gln Glu Ser Gly Pro Gly Leu Val Lys Pro Ser Gln
        1               5                   10                  15

Ser Leu Ser Leu Thr Cys Ser Val Thr Gly Tyr Ser Ile Thr Ser Ala
                    20                  25                  30

Tyr Tyr Trp Asn Trp Ile Arg Gln Phe Pro Gly Asn Lys Leu Glu Trp
                    35                  40                  45

Met Gly Tyr Ile Ser Tyr Gly Gly Ser Asn Ser Tyr Ala Pro Ser Leu
            50                  55                  60

Lys Asn Arg Phe Ser Ile Thr Arg Asp Thr Ser Lys Asn Gln Phe Phe
        65                  70                  75                  80

Leu Lys Leu Asn Ser Val Thr Thr Glu Asp Thr Ala Thr Tyr Tyr Cys
                        85                  90                  95

Ala Arg Glu Ser Asp Tyr Ala Tyr Phe Asp Tyr Trp Gly Gln Gly Thr
                    100                 105                 110

Thr Leu Thr Val Ser Ser Ala Ser Thr Lys Gly Pro Ser Val Phe Pro
                    115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
        145                 150                 155                 160

Ser Gly Ala Leu Thr Ser Gly Val His Thr Phe Pro Ala Val Leu Gln
                        165                 170                 175

Ser Ser Gly Leu Tyr Ser Leu Ser Ser Val Val Thr Val Pro Ser Ser
                    180                 185                 190

Ser Leu Gly Thr Gln Thr Tyr Ile Cys Asn Val Asn His Lys Pro Ser
                    195                 200                 205
```

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Cys Thr Leu
        340                 345                 350

Pro Pro Ser Arg Asp Glu Leu Thr Lys Asn Gln Val Ser Leu Ser Cys
    355                 360                 365

Ala Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

Gly Gly Gly Gly Ser Gly Gly Gly Ser Leu Glu Val Leu Phe
450                 455                 460

Gln Gly Pro Ser Gly Gly Gly Ser Gly Gly Gly Ser Asp Ile
465                 470                 475                 480

Gln Met Thr Gln Ser Pro Ser Ser Leu Ser Ala Ser Val Gly Asp Arg
            485                 490                 495

Val Thr Ile Thr Cys Lys Ser Ser Gln Ser Leu Leu Tyr Thr Ser Ser
        500                 505                 510

Gln Lys Asn Tyr Leu Ala Trp Tyr Gln Gln Lys Pro Gly Lys Ala Pro
    515                 520                 525

Lys Leu Leu Ile Tyr Trp Ala Ser Thr Arg Glu Ser Gly Val Pro Ser
530                 535                 540

Arg Phe Ser Gly Ser Gly Ser Gly Thr Asp Phe Thr Leu Thr Ile Ser
545                 550                 555                 560

Ser Leu Gln Pro Glu Asp Phe Ala Thr Tyr Tyr Cys Gln Gln Tyr Tyr
            565                 570                 575

Ala Tyr Pro Trp Thr Phe Gly Cys Gly Thr Lys Val Glu Ile Lys Arg
        580                 585                 590

<210> SEQ ID NO 9
<211> LENGTH: 214
<212> TYPE: PRT
<213> ORGANISM: Artificial Sequence
<220> FEATURE:
<223> OTHER INFORMATION: Description of Artificial Sequence: Synthetic -continued

```
                             polypeptide
<220> FEATURE:
<223> OTHER INFORMATION: Her3/MetSS_KHSS_PreSci - LC (Her3clone29_KO1_
      LC)

<400> SEQUENCE: 9

Asp Ile Gln Met Thr Gln Thr Thr Ser Ser Leu Ser Ala Ser Leu Gly
1               5                   10                  15

Asp Arg Val Thr Ile Ser Cys Arg Ala Arg Gln Asp Ile Ser Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Phe Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Her3/MetSS-3C-FS1 - HC1 (SS_KnobsHC1_VHcMet)

<400> SEQUENCE: 10

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Ser Asn Ser Tyr Ala Pro Ser Leu
    50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95
```

-continued

```
Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

Gly Gly Gly Gly Ser Gly Gly Gly Gly Ser Gly Gly Gly Gly Ser Glu
            450                 455                 460

Val Gln Leu Val Glu Ser Gly Gly Gly Leu Val Gln Pro Gly Gly Ser
465                 470                 475                 480

Leu Arg Leu Ser Cys Ala Ala Ser Gly Tyr Thr Phe Thr Ser Tyr Trp
            485                 490                 495

Leu His Trp Val Arg Gln Ala Pro Gly Lys Cys Leu Glu Trp Val Gly
            500                 505                 510
```

```
Met Ile Asp Pro Ser Asn Ser Asp Thr Arg Phe Asn Pro Asn Phe Lys
            515                 520                 525

Asp Arg Phe Thr Ile Ser Ala Asp Thr Ser Lys Asn Thr Ala Tyr Leu
    530                 535                 540

Gln Met Asn Ser Leu Arg Ala Glu Asp Thr Ala Val Tyr Tyr Cys Ala
545                 550                 555                 560

Thr Tyr Arg Ser Tyr Val Thr Pro Leu Asp Tyr Trp Gly Gln Gly Thr
                565                 570                 575

Leu Val Thr Val Ser Ser
            580

<210> SEQ ID NO 11
<211> LENGTH: 577
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Her3/MetSS-3C-FS1 - HC2 (SS_HolesHC2 _VLcMet_
      FS1)

<400> SEQUENCE: 11

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Ser Asn Ser Tyr Ala Pro Ser Leu
    50                  55                  60

Lys Asn Arg Phe Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ser Asp Tyr Ala Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

Glu Val Lys Phe Asn Trp Tyr Val Asp Gly Val Glu His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Gly Gly Gly Ser Gly Gln Ser Ser Arg His Arg Arg Ala Leu Asp
    450                 455                 460

Ile Gln Met Thr Gln Ser Pro Ser Ser Leu Ser Ala Ser Val Gly Asp
465                 470                 475                 480

Arg Val Thr Ile Thr Cys Lys Ser Ser Gln Ser Leu Leu Tyr Thr Ser
                485                 490                 495

Ser Gln Lys Asn Tyr Leu Ala Trp Tyr Gln Gln Lys Pro Gly Lys Ala
            500                 505                 510

Pro Lys Leu Leu Ile Tyr Trp Ala Ser Thr Arg Glu Ser Gly Val Pro
        515                 520                 525

Ser Arg Phe Ser Gly Ser Gly Ser Gly Thr Asp Phe Thr Leu Thr Ile
    530                 535                 540

Ser Ser Leu Gln Pro Glu Asp Phe Ala Thr Tyr Tyr Cys Gln Gln Tyr
545                 550                 555                 560

Tyr Ala Tyr Pro Trp Thr Phe Gly Cys Gly Thr Lys Val Glu Ile Lys
                565                 570                 575

Arg

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Her3/MetSS-3C-FS1 - LC (Her3clone29_KO1_LC)

<400> SEQUENCE: 12

Asp Ile Gln Met Thr Gln Thr Thr Ser Ser Leu Ser Ala Ser Leu Gly
1               5                   10                  15

Asp Arg Val Thr Ile Ser Cys Arg Ala Arg Gln Asp Ile Ser Asn Tyr
            20                  25                  30

```
Leu Asn Trp Tyr Gln Arg Lys Pro Asp Gly Thr Val Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Phe Pro Trp
                 85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Furin specific protease cleavage site variant
      1 - FS1

<400> SEQUENCE: 13

Gln Ser Ser Arg His Arg Arg Ala Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Furin specific protease cleavage site variant
      2 - FS2

<400> SEQUENCE: 14

Leu Ser His Arg Ser Lys Arg Ser Leu
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: PreScission specific protease cleavage site

<400> SEQUENCE: 15

Leu Glu Val Leu Phe Gln Gly Pro
1               5

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(24)
<223> OTHER INFORMATION: This sequence may encompass 3, 4, 5, or 6 'Gly
      Gly Gly Ser' repeating units
<220> FEATURE:
<223> OTHER INFORMATION: see specification as filed for detailed
      description of substitutions and preferred embodiments

<400> SEQUENCE: 16

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(24)
<223> OTHER INFORMATION: This region may encompass 3, 4, 5, or 6 'Gly
      Gly Gly Ser' repeating units
<220> FEATURE:
<221> NAME/KEY: misc_feature
<222> LOCATION: (25)..(27)
<223> OTHER INFORMATION: This region may encompass 0, 1, 2, or 3
      residues
<220> FEATURE:
<223> OTHER INFORMATION: see specification as filed for detailed
      description of substitutions and preferred embodiments

<400> SEQUENCE: 17

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly
            20                  25

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This region may encompass 2, 3, 4, 5, or 6
      'Gly Gly Gly Gly Ser' repeating units
<220> FEATURE:
<223> OTHER INFORMATION: see specification as filed for detailed
      description of substitutions and preferred embodiments

```
<400> SEQUENCE: 18

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Ser
            20                  25                  30

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This region may encompass 2, 3, 4, 5, or 6
      'Gly Gly Gly Gly Ser' repeating units
<220> FEATURE:
<221> NAME/KEY: misc_feature
<222> LOCATION: (31)..(33)
<223> OTHER INFORMATION: This region may encompass 0, 1, 2, or 3
      residues
<220> FEATURE:
<223> OTHER INFORMATION: see specification as filed for detailed
      description of substitutions and preferred embodiments

<400> SEQUENCE: 19

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Ser Gly Gly
            20                  25                  30

Gly

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Asn Arg Arg
1

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Ser
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 22

Gly Gly Gly Gly Ser Gly Gly Gly Gly Ser Gly Leu Glu Val Leu Phe
1               5                   10                  15

Gln Gly Pro Ser Gly Gly Gly Ser Gly Gly Gly Gly Ser
            20              25              30

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Gly Gly Gly Ser Gly Gly Gly Gly Ser Gly Gln Ser Ser Arg His
1               5                   10                  15

Arg Arg Ala Leu Gly Gly Gly Gly Ser Gly Gly Gly Gly Ser
            20              25              30

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Gly Gly Ser Gly Gly Gly Gly Ser Gly Gly Gly Gly Ser
1               5                   10                  15
```

BISPECIFIC ANTIBODIES COMPRISING A DISULFIDE STABILIZED-FV FRAGMENT

CROSS REFERENCE TO RELATED APPLICATIONS

This application is a continuation of International Application No. PCT/EP2011/064476 having an international filing date of Aug. 23, 2011, the entire contents of which are incorporated herein by reference, and which claims benefit under 35 U.S.C. §119 to European Patent Application No. 10173914.2, filed Aug. 24, 2010.

SEQUENCE LISTING

The instant application contains a Sequence Listing submitted via EFS-Web and hereby incorporated by reference in its entirety. Said ASCII copy, created on Feb. 18, 2013, is named P4503CIUSSeqList.txt, and is 55,765 bytes in size.

FIELD OF THE INVENTION

The present invention relates to trivalent, bispecific antibodies, methods for their production, pharmaceutical compositions containing said antibodies, and uses thereof.

BACKGROUND OF THE INVENTION

A wide variety of multispecific recombinant antibody formats has been developed in the recent past, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al, Nature Biotech 23 (2005) 1126-1136; Fischer, N., and Léger, O., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N., and Léger, O., Pathobiology 74 (2007) 3-14). It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

A process for the preparation of biologically active antibody dimers is reported in U.S. Pat. No. 6,897,044. Multivalent $F_v$ antibody construct having at least four variable domains which are linked with each over via peptide linkers are reported in U.S. Pat. No. 7,129,330. Dimeric and multimeric antigen binding structures are reported in US 2005/0079170. Tri- or tetra-valent mono specific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342. In WO 2007/109254 stabilized binding molecules that consist of or comprise a stabilized scFv are reported.

In WO 2007/024715 are reported dual variable domain immunoglobulins as engineered multivalent and multispecific binding proteins.

WO 2011/034605 relates to engineered protein complexes constructed using a coiled coil and/or a tether and methods for making, using, and purifying such complexes, such as multispecific antibodies or other multispecific Fc containing complexes.

SUMMARY OF THE INVENTION

The current invention relates to a bispecific antibody comprising
a) a full length antibody specifically binding to a first antigen and consisting of two antibody heavy chains and two antibody light chains;
b) a Fv fragment specifically binding to a second antigen comprising a $VH^2$ domain and a $VL^2$ domain, wherein both domains are connected via a disulfide bridge, and wherein only either the $VH^2$ domain or the $VL^2$ domain is fused via a peptide linker to the heavy or light chain of the full length antibody specifically binding to a first antigen.

In one embodiment the bispecific antibody according to claim 1 characterized in that
the bispecific antibody is trivalent and
either the $VH^2$ domain or the $VL^2$ domain is fused via a peptide linker to the heavy chain of the full length antibody specifically binding to a first antigen.

In one embodiment the bispecific antibody according to claim 2 characterized in that
the $VH^2$ domain or $VL^2$ domain is N-terminally fused via a peptide linker to the C-terminus of the full length antibody specifically binding to a first antigen.

In one embodiment the bispecific antibody according to claim 2, characterized in that
the bispecific antibody is trivalent and the $VH^2$ domain or $VL^2$ domain is C-terminally fused via a peptide linker to the N-terminus of the full length antibody specifically binding to a first antigen.

In one embodiment the bispecific antibody according to the invention is characterized in that the bispecific antibody is trivalent and the $VH^2$ domain or $VL^2$ domain is N-terminally fused via a peptide linker to the C-terminus of the heavy or light chain of the full length antibody specifically binding to a first antigen.

In one embodiment the bispecific antibody according to the invention is characterized in that
the $VH^2$ domain or $VL^2$ domain is C-terminally fused via a peptide linker to the N-terminus of the heavy or light chain of the full length antibody specifically binding to a first antigen.

In one embodiment the bispecific antibody according to the invention is characterized in that the VH² domain or VL² domain is N-terminally fused via a peptide linker to the C-terminus of the heavy or light chain of the full length antibody specifically binding to a first antigen, or the VH² domain or VL² domain is C-terminally fused via a peptide linker to the N-terminus of the heavy or light chain of the full length antibody specifically binding to a first antigen.

In one embodiment the bispecific antibody according to the invention is characterized in that
the bispecific antibody is trivalent and either the VH2 domain or the VL2 domain is fused via a peptide linker to the heavy chain of the full length antibody specifically binding to a first antigen.

In one embodiment the trivalent, bispecific antibody according to the invention is characterized in that the VH2 domain or VL2 domain is N-terminally fused via a peptide linker to the C-terminus of the heavy chain of the full length antibody specifically binding to a first antigen.

In one embodiment the trivalent bispecific antibody according to the invention is characterized in that the VH2 domain or VL2 domain is C-terminally fused via a peptide linker to the N-terminus of the heavy chain of the full length antibody specifically binding to a first antigen.

In one embodiment the bispecific antibody according to the invention is characterized in that
the VH² domain and the VL² domain are connected via a disulfide bridge which is introduced between the following positions:
i) VH² domain position 44 and VL² domain position 100,
ii) VH² domain position 105 and VL² domain position 43, or
iii) VH² domain position 101 and VL² domain position 100.
(according to the Kabat numbering)

In one embodiment the bispecific antibody according to the invention is characterized in that
the VH² domain and the VL² domain are connected via a disulfide bridge which is introduced between VH² domain position 44 and VL² domain position 100.

In one embodiment the bispecific antibody according to the invention is characterized in that
the first CH3 domain of the heavy chain of the whole antibody and the second CH3 domain of the whole antibody each meet at an interface which comprises an alteration in the original interface between the antibody CH3 domains;
wherein i) in the CH3 domain of one heavy chain,
an amino acid residue is replaced with an amino acid residue having a larger side chain volume, thereby generating a protuberance within the interface of the CH3 domain of one heavy chain which is positionable in a cavity within the interface of the CH3 domain of the other heavy chain
and
ii) in the CH3 domain of the other heavy chain,
an amino acid residue is replaced with an amino acid residue having a smaller side chain volume, thereby generating a cavity within the interface of the second CH3 domain within which a protuberance within the interface of the first CH3 domain is positionable.

One aspect of the invention is a method for the preparation of the bispecific antibody according to the invention comprising the steps of
A) expressing in a mammalian cell nucleic acid encoding a bispecific antibody comprising a) a full length antibody specifically binding to a first antigen and consisting of two antibody heavy chains and two antibody light chains;
b) a Fv fragment specifically binding to a second antigen comprising a VH² domain and a VL² domain, wherein both domains are connected via a disulfide bridge, and wherein the Fv fragment is fused
via the N-termini of the VH² domain and the VL² domain to the both C-termini of the heavy chain of the full length antibody specifically binding to a first antigen via a first and second peptide linker to, or
via the C-termini of the VH² domain and the VL² domain to the both N-termini of one heavy and one light chain of the full length antibody specifically binding to a first antigen via a first and second peptide linker,
characterized in that
one of the linkers comprises a protease cleavage site cleavable by furin, and the other linker does not comprise a protease cleavage site;
B) recovering said antibody from said cell or the cell culture supernatant.

Another aspect of the invention is a method for the preparation of the trivalent, bispecific antibody according to the invention comprising the steps of
A) expressing in a mammalian cell nucleic acid encoding a bispecific antibody comprising
a) a full length antibody specifically binding to a first antigen and consisting of two antibody heavy chains and two antibody light chains;
b) a Fv fragment specifically binding to a second antigen comprising a VH² domain and a VL² domain, wherein both domains are connected via a disulfide bridge, and wherein the Fv fragment is fused
via the N-termini of the VH² domain and the VL² domain to the both C-termini of the heavy chains of the full length antibody specifically binding to a first antigen via a first and second peptide linker to, or
via the C-termini of the VH² domain and the VL² domain to the both N-termini of the heavy chains of the full length antibody specifically binding to a first antigen via a first and second peptide linker,
characterized in that
one of the linkers comprises a protease cleavage site cleavable by Prescission protease, and the other linker does not comprise a protease cleavage site;
B) recovering said antibody from said cell or the cell culture supernatant.

In one embodiment the method is characterized in that
the protease cleavage site cleavable by furin is SEQ ID NO:13 or SEQ ID NO:14.

In one embodiment the method is characterized in that
the protease cleavage site cleavable by Prescission protease is SEQ ID NO:15.

In one embodiment the method is characterized in that
a mammalian cell, in one embodiment a CHO cell, NS0 cell, SP2/0 cell, HEK293 cell, COS cell, PER.C6 cell, in another embodiment a HEK293 cell or CHO cell.

One aspect of the invention is an antibody obtained by such recombinant methods.

One aspect of the invention is an pharmaceutical composition comprising the bispecific antibody according to the invention.

One aspect of the invention is the bispecific antibody according the invention for the treatment of cancer.

One aspect of the invention is the use of the bispecific antibody according the invention for the manufacture of a medicament for the treatment of cancer.

The invention further provides a method for treating a patient suffering from a disease like e.g. cancer or inflammation, comprising administering to a patient diagnosed as having such a disease (and therefore being in need of such a therapy) an effective amount of an antibody according to the invention. The antibody is administered preferably in a pharmaceutical composition.

The bispecific antibodies according to the invention one the one hand show valuable properties like biological activity due to their binding to different antigens. The disulfide stabilized Fv fragment binding to the second antigen shows excellent binding properties due the high flexibility (as it is only fused to the full length antibody via one peptided linker) and is quite independent of the linker length.

On the other hand are suitable for production and pharmaceutical formulation due to their stability, low aggregation and pharmacokinetic and biological properties. Due to their Ig core they still retain the properties of natural antibodies like ADCC and CDC.

DESCRIPTION OF THE FIGURES

FIG. 4A-D: Composition of trivalent bispecific antibody derivatives according to the invention
- 4A: Modular composition of trivalent bispecific antibody derivatives according to the invention
- 4B: direct assembly of Fv fragment
- 4C: improved assembly via intermediate with second linker with protease cleavage site, which will be cleaved either during/or after expression to yield the bispecific antibody according to the invention
- 4D: connector-peptides (SEQ ID NOs: 21-23, respectively, in order of appearance) with recognition sequences for proteolytic processing in target cells (by furin) or in vitro (by Prescission protease) for the intermediate approach under 4C.

FIG. 14A: For Biacore analyses, bispecific antibodies according to the invention and control antibodies were captured to the chip by anti-Fc antibodies and exposed to soluble forms of the target antigens on cell surfaces (=target 1). On and off rates were calculated from the binding curves by standard techniques. FIG. 14B: Binding analyses by Surface Plasmon resonance of the LeY-Dig bispecific antibody demonstrates simultaneous binding of target 1 and target 2 specificities. The bispecific antibodies according to the invention were captured to the chip by anti-Fc antibodies, exposed to soluble forms of the target 1 antigen (first binding curve) and thereafter exposed to target 2 antigen. The appearance of the $2^{nd}$ antigen derived curve 'on top' of the first binding curve proves that both antigens are bound simultaneously to the bispecific antibody (FIG. 14C).

FIG. 15A: For Biacore analyses, bispecific antibodies according to the invention and control antibodies were captured to the chip by immobilized target 1 antigen CD22 and thereafter exposed to Dig-siRNA as target 2 antigen. On and off rates were calculated from the binding curves by standard techniques. FIG. 15B: Binding analyses by Surface Plasmon resonance of the CD22-Dig bispecific antibody demonstrates simultaneous binding of target 1 and target 2 specificities. The bispecific antibodies according to the invention were captured to the chip by CD22 binding. The appearance of the $2^{nd}$ antigen derived curve 'on top' of the first binding curve proves that both antigens are bound simultaneously to the bispecific antibody.

DETAILED DESCRIPTION OF THE INVENTION

The current invention relates to a bispecific antibody comprising
a) a full length antibody specifically binding to a first antigen and consisting of two antibody heavy chains and two antibody light chains;
b) a Fv fragment specifically binding to a second antigen comprising a $VH^2$ domain and a $VL^2$ domain, wherein both domains are connected via a disulfide bridge, and wherein only either the $VH^2$ domain or the $VL^2$ domain is fused via a peptide linker to the heavy or light chain of the full length antibody specifically binding to a first antigen.

(and the other of the $VH^2$ domain or the $VL^2$ domain is not fused via a peptide linker to the heavy or light chain of the full length antibody specifically binding to a first antigen).

In one embodiment the bispecific antibody according to the invention is characterized in that
the $VH^2$ domain or $VL^2$ domain is N-terminally fused via a peptide linker to the C-terminus of the heavy or light chain of the full length antibody specifically binding to a first antigen.

In one embodiment the bispecific antibody according to the invention is characterized in that
the $VH^2$ domain is N-terminally fused via a peptide linker to the C-terminus of the heavy or light chain of the full length antibody specifically binding to a first antigen.

In one embodiment the bispecific antibody according to the invention is characterized in that
the $VH^2$ domain is N-terminally fused via a peptide linker to the C-terminus of the heavy chain of the full length antibody specifically binding to a first antigen.

In one embodiment the bispecific antibody according to the invention is characterized in that
the $VH^2$ domain is N-terminally fused via a peptide linker to the C-terminus of the light chain of the full length antibody specifically binding to a first antigen.

In one embodiment the bispecific antibody according to the invention is characterized in that
the $VL^2$ domain is N-terminally fused via a peptide linker to the C-terminus of the heavy or light chain of the full length antibody specifically binding to a first antigen.

In one embodiment the bispecific antibody according to the invention is characterized in that
the $VL^2$ domain is N-terminally fused via a peptide linker to the C-terminus of the heavy chain of the full length antibody specifically binding to a first antigen.

In one embodiment the bispecific antibody according to the invention is characterized in that
the $VL^2$ domain is N-terminally fused via a peptide linker to the C-terminus of the light chain of the full length antibody specifically binding to a first antigen.

Figure 2A:
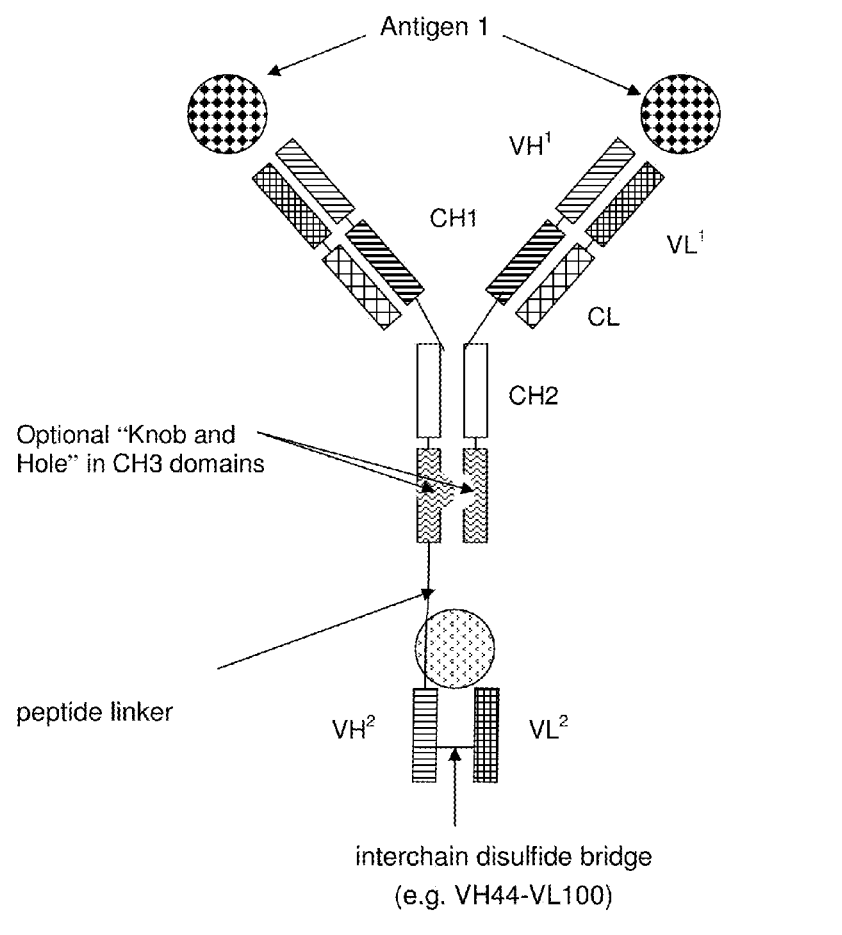
FIG. 2A-C Schematic representation of a trivalent, bispecific antibody according to the invention, comprising a full length antibody (with optional knobs into holes modifications in the CH3 domains) which specifically binds to a first antigen 1 and to whose C-terminus a disulfide-stabilized Fv fragment specifically binding to a second antigen 2, is fused via the N-terminus of either the VH$^2$ (FIG. 2A) or the VL$^2$ (FIG. 2B) of the disulfide-stabilized Fv fragment, or via the VH$^2$ of the disulfide-stabilized Fab fragment (FIG. 2C).
Figure 2B:
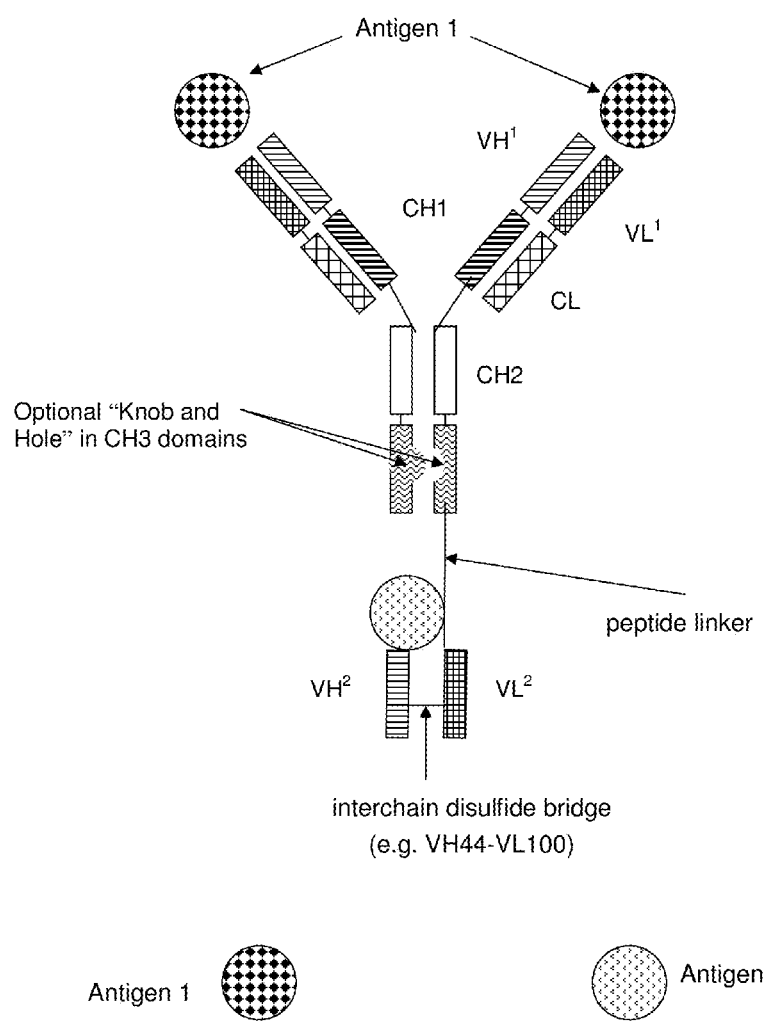
Figure 2C:
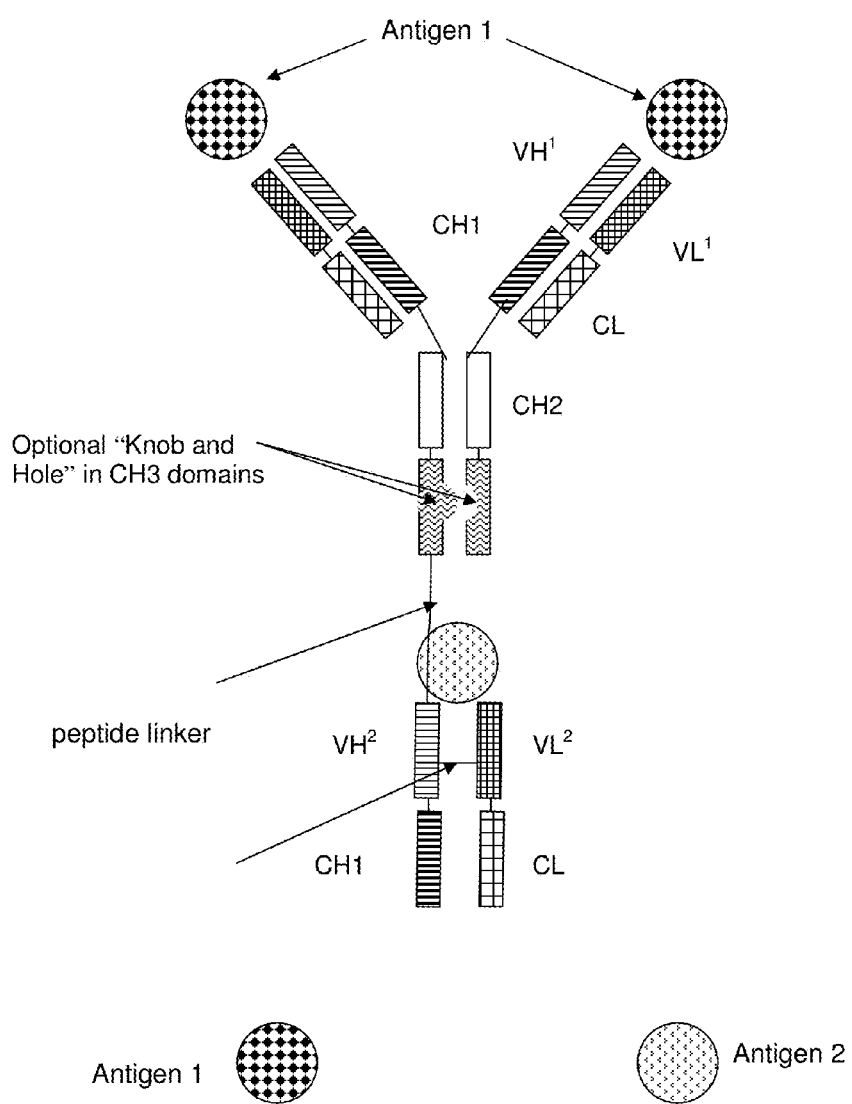

In one embodiment the bispecific antibody according to the invention is characterized in that
the $VH^2$ domain or $VL^2$ domain is N-terminally fused via a peptide linker to the C-terminus of the heavy or light chain of the full length antibody specifically binding to a first antigen; and
a CH1 domain is N-terminally fused to the C-terminus $VH^2$ domain and a CL domain is N-terminally fused to the C-terminus $VL^2$ domain (see e.g. FIG. 2c).

In one embodiment the bispecific antibody according to the invention is characterized in that
the $VH^2$ domain or $VL^2$ domain is C-terminally fused via a peptide linker to the N-terminus of the heavy or light chain of the full length antibody specifically binding to a first antigen.

In one embodiment the bispecific antibody according to the invention is characterized in that
the $VH^2$ domain is C-terminally fused via a peptide linker to the N-terminus of the heavy or light chain of the full length antibody specifically binding to a first antigen, In one embodiment the bispecific antibody according to the invention is characterized in that
the $VH^2$ domain is C-terminally fused via a peptide linker to the N-terminus of the heavy chain of the full length antibody specifically binding to a first antigen.

In one embodiment the bispecific antibody according to the invention is characterized in that the VH² domain is C-terminally fused via a peptide linker to the N-terminus of the light chain of the full length antibody specifically binding to a first antigen.

In one embodiment the bispecific antibody according to the invention is characterized in that
the VL² domain is C-terminally fused via a peptide linker to the N-terminus of the heavy or light chain of the full length antibody specifically binding to a first antigen.

In one embodiment the bispecific antibody according to the invention is characterized in that
the VL² domain is C-terminally fused via a peptide linker to the N-terminus of the heavy chain of the full length antibody specifically binding to a first antigen.

In one embodiment the bispecific antibody according to the invention is characterized in that
the VL² domain is C-terminally fused via a peptide linker to the N-terminus of the light chain of the full length antibody specifically binding to a first antigen.

In one embodiment the bispecific antibody according to the invention is characterized in that
a) the bispecific antibody is trivalent and
b) either the VH2 domain or the VL2 domain is fused via a peptide linker to the heavy chain of the full length antibody specifically binding to a first antigen.

In one embodiment such trivalent, bispecific antibody is characterized in that the VH² domain or VL² domain is N-terminally fused via a peptide linker to the C-terminus of the heavy chain of the full length antibody specifically binding to a first antigen.

In one embodiment such trivalent bispecific antibody is characterized in that the VH² domain or VL² domain is C-terminally fused via a peptide linker to the N-terminus of the heavy chain of the full length antibody specifically binding to a first antigen.

In one embodiment the bispecific antibody according to the invention is characterized in that
the VH² domain and the VL² domain are connected via a disulfide bridge which is introduced between the following positions:
i) VH² domain position 44 and VL² domain position 100,
ii) VH² domain position 105 and VL² domain position 43, or
iii) VH² domain position 101 and VL² domain position 100 (numbering always according to EU index of Kabat).

In one embodiment the bispecific antibody according to the invention is characterized in that
the VH² domain and the VL² domain are connected via a disulfide bridge which is introduced between
VH² domain position 44 and VL² domain position 100 (numbering always according to EU index of Kabat).

Techniques to introduce unnatural disulfide bridges for stabilization are described e.g. in WO 94/029350, U.S. Pat. No. 5,747,654, Rajagopal, V., et al., Prot. Engin. 10 (1997) 1453-1459; Reiter, Y., et al., Nature Biotechnology 14 (1996) 1239-1245; Reiter; Y., et al., Protein Engineering; 8 (1995) 1323-1331; Webber, K. O., et al., Molecular Immunology 32 (1995) 249-258; Reiter, Y., et al., Immunity 2 (1995) 281-287; Reiter, Y., et al., JBC 269 (1994) 18327-18331; Reiter, Y., et al., Inter. J. of Cancer 58 (1994) 142-149, or Reiter, Y., Cancer Res. 54 (1994) 2714-2718. In one embodiment the optional disulfide bond between the variable domains of the polypeptides under b) and c) is between heavy chain variable domain position 44 and light chain variable domain position 100. In one embodiment the optional disulfide bond between the variable domains of the polypeptides under b) and c) is between heavy chain variable domain position 105 and light chain variable domain position 43 (numbering always according to EU index of Kabat). In one embodiment a trivalent, bispecific antibody without said optional disulfide stabilization between the variable domains VH and VL of the single chain Fab fragments is preferred.

Figure 1:
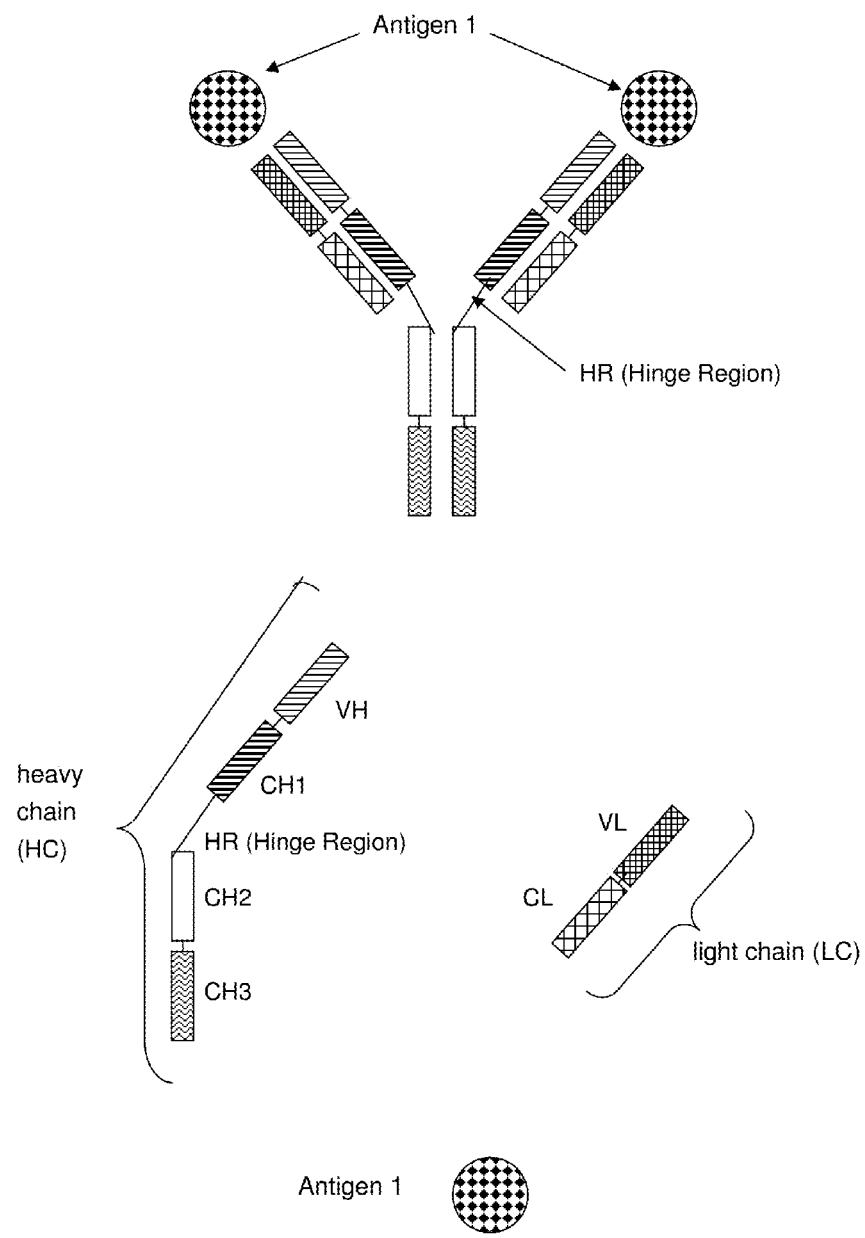
FIG. 1 Schematic structure of a full length antibody without CH4 domain specifically binding to a first antigen 1 with two pairs of heavy and light chain which comprise variable and constant domains in a typical order.

The term "full length antibody" denotes an antibody consisting of two "full length antibody heavy chains" and two "full length antibody light chains" (see FIG. 1). A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g. IgG 1 and IgG2), IgM, IgA, IgD, and IgE.) The full length antibodies according to the invention can be from a single species e.g. human, or they can be chimerized or humanized antibodies. The full length antibodies according to the invention comprise two antigen binding sites each formed by a pair of VH and VL, which both specifically bind to the same antigen. The C-terminus of the heavy or light chain of said full length antibody denotes the last amino acid at the C-terminus of said heavy or light chain.

The N-terminus of the antibody heavy chain variable domain (VH) of the polypeptide under b) and the antibody light chain variable domain (VL) of the polypeptide under c) denotes the last amino acid at the N-terminus of VH or VL domain.

The term "Fv fragment" as used herein refers to a VH² domain and a VL² domain of an antibody specifically binding to an antigen, both domains forming together a Fv fragment. The Fv fragment binding to the second antigen within the bispecific antibody according to the invention comprises a (interchain) disulfide bridge between both domains VH² and VL², i.e. the domains VH² domain and a VL² both are connected via a unnatural disulfide bridge for stabilization, which is introduced by techniques described e.g. in WO 94/029350, U.S. Pat. No. 5,747,654, Rajagopal, V., et al., Prot. Engin. 10 (1997) 1453-1459; Reiter, Y., et al., Nature Biotechnology 14 (1996) 1239-1245; Reiter; Y., et al., Protein Engineering; 8 (1995) 1323-1331; Webber, K. O., et al., Molecular Immunology 32 (1995) 249-258; Reiter, Y., et al., Immunity 2 (1995) 281-287; Reiter, Y., et al., JBC 269 (1994) 18327-18331; Reiter, Y., et al., Inter. J. of Cancer 58 (1994) 142-149, or Reiter, Y., Cancer Res. 54 (1994) 2714-2718.

The VH² and VL² domains of the Fv fragment binding to the second antigen within the bispecific antibody according to the invention are not connected via a peptide linker with each other (i.e. VH² and VL² do not form a single chain Fv fragments). Therefore the term "a Fv fragment specifically binding to a second antigen comprising a VH² domain and a VL² domain, wherein both domains are connected via a disulfide bridge" refers a Fv fragment to a wherein both domains are connected via a disulfide bridge as only covalent linkage between both domains" and not to via a further covalent linkage (as for example in a single chain Fv fragments via a peptide linker).

The domains VH² and VL² of the Fv fragment can either be derived from a full length antibody or other techniques like e.g. phage display.

In one embodiment the bispecific antibody according to the invention is a trivalent, bispecific antibody and the Fv fragment (binding to a second antigen) is fused to the heavy chain of the full length antibody binding to the first antigen. The term "valent" as used within the current application denotes the presence of a specified number of binding sites in an antibody molecule. A natural antibody for example or a full length antibody according to the invention has two binding sites and is bivalent. As such, the term "trivalent", denote the presence of three binding sites in an antibody molecule. The term "trivalent, trispecific" antibody as used herein denotes an antibody that has three antigen-binding sites of which each binds to another antigen (or another epitope of the antigen). Antibodies of the present invention have three to four binding sites, i.e. are tri- or tetravalent (preferably tri valent) and are bispecific.

Antibody specificity refers to selective recognition of the antibody for a particular epitope of an antigen. Natural antibodies, for example, are monospecific. Bispecific antibodies are antibodies which have two different antigen-binding specificities. Where an antibody has more than one specificity, the recognized epitopes may be associated with a single antigen or with more than one antigen.

The term "monospecific" antibody as used herein denotes an antibody that has one or more binding sites each of which bind to the same epitope of the same antigen.

Typical trivalent, bispecific antibodies according to the invention are shown e.g. in FIGS. 2a and 2b, 3d and 3c.

For a trivalent, bispecific antibodies according to the invention modifications in the CH3 domain enhancing the heterodimerization of the two different heavy chains (see Figures FIGS. 2a and 2b, 3d and 3c) are especially useful.

Therefore for such trivalent, bispecific antibodies the CH3 domains of said full length antibody according to the invention can be altered by the "knob-into-holes" technology which is described in detail with several examples in e.g. WO 96/027011, Ridgway, J. B., et al., Protein Eng 9 (1996) 617-621; and Merchant, A. M., et al., Nat Biotechnol 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech 16 (1998) 677-681; Atwell, S., et al., J. Mol. Biol. 270 (1997) 26-35) and increases the yield.

Thus in one aspect of the invention said trivalent, bispecific antibody is further is characterized in that the CH3 domain of one heavy chain of the full length antibody and the CH3 domain of the other heavy chain of the full length antibody each meet at an interface which comprises an original interface between the antibody CH3 domains;
wherein said interface is altered to promote the formation of the bivalent, bispecific antibody, wherein the alteration is characterized in that:

a) the CH3 domain of one heavy chain is altered,
so that within the original interface the CH3 domain of one heavy chain that meets the original interface of the CH3 domain of the other heavy chain within the bivalent, bispecific antibody,
an amino acid residue is replaced with an amino acid residue having a larger side chain volume, thereby generating a protuberance within the interface of the CH3 domain of one heavy chain which is positionable in a cavity within the interface of the CH3 domain of the other heavy chain
and
b) the CH3 domain of the other heavy chain is altered,
so that within the original interface of the second CH3 domain that meets the original interface of the first CH3 domain within the trivalent, bispecific antibody an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W). Preferably said amino acid residue having a smaller side chain volume is selected from the group consisting of alanine (A), serine (S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In a preferred embodiment, said trivalent, bispecific comprises a T366W mutation in the CH3 domain of the "knobs chain" and T366S, L368A, Y407V mutations in the CH3 domain of the "hole chain". An additional interchain disulfide bridge between the CH3 domains can also be used (Merchant, A. M., et al., Nature Biotech 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, said trivalent, bispecific antibody comprises Y349C, T366W mutations in one of the two CH3 domains and E356C, T366S, L368A, Y407V mutations in the other of the two CH3 domains or said trivalent, bispecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering always according to EU index of Kabat). But also other knobs-in-holes technologies as described by EP 1 870 459A1, can be used alternatively or additionally. A preferred example for said trivalent, bispecific antibody are R409D; K370E mutations in the CH3 domain of the "knobs chain" and D399K; E357K mutations in the CH3 domain of the "hole chain" (numbering always according to EU index of Kabat).

In another preferred embodiment said trivalent, bispecific antibody comprises a T366W mutation in the CH3 domain of the "knobs chain" and T366S, L368A, Y407V mutations in the CH3 domain of the "hole chain" and additionally R409D; K370E mutations in the CH3 domain of the "knobs chain" and D399K; E357K mutations in the CH3 domain of the "hole chain".

In another preferred embodiment said trivalent, bispecific antibody comprises Y349C, T366W mutations in one of the two CH3 domains and S354C, T366S, L368A, Y407V mutations in the other of the two CH3 domains or said trivalent, bispecific antibody comprises Y349C, T366W mutations in one of the two CH3 domains and S354C, T366S, L368A, Y407V mutations in the other of the two CH3 domains and additionally R409D; K370E mutations in the CH3 domain of the "knobs chain" and D399K; E357K mutations in the CH3 domain of the "hole chain".

The bispecific antibody to the invention comprises different antigen-binding sites The full length antibody according comprises two identical antigen-binding sites specifically binding to a first antigen, and the antibody heavy chain variable domain $VH^2$ the antibody light chain variable domain $VL^2$ of the disulfide stabilized Fv fragment form together one antigen binding site specifically binding to a second antigen.

The terms "binding site" or "antigen-binding site" as used herein denotes the region(s) of said bispecific antibody according to the invention to which the respective antigen actually specifically binds. The antigen binding sites either in the full length antibody or in the Fv fragment are formed each by a pair consisting of an antibody light chain variable domain (VL) and an antibody heavy chain variable domain (VH).

The antigen-binding sites that specifically bind to the desired antigen can be derived a) from known antibodies to the antigen or b) from new antibodies or antibody fragments obtained by de novo immunization methods using inter alia either the antigen protein or nucleic acid or fragments thereof or by phage display.

An antigen-binding site of an antibody of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

Antibody specificity refers to selective recognition of the antibody for a particular epitope of an antigen. Natural antibodies, for example, are monospecific. "Bispecific antibodies" according to the invention are antibodies which have two different antigen-binding specificities. Where an antibody has more than one specificity, the recognized epitopes may be associated with a single antigen or with more than one antigen. The term "monospecific" antibody as used herein denotes an antibody that has one or more binding sites each of which bind to the same epitope of the same antigen.

The term "valent" as used within the current application denotes the presence of a specified number of binding sites in an antibody molecule. A natural antibody for example or a full length antibody according to the invention has two binding sites and is bivalent. As such, the terms "trivalent", denote the presence of three binding sites in an antibody molecule. As such, the terms "tetravalent", denote the presence of three binding sites in an antibody molecule. In one embodiment the bispecific antibodies according to the invention are trivalent or tetravalent. In one embodiment the bispecific antibodies according to the invention are trivalent.

The full length antibodies of the invention comprise immunoglobulin constant regions of one or more immunoglobulin classes. Immunoglobulin classes include IgG, IgM, IgA, IgD, and IgE isotypes and, in the case of IgG and IgA, their subtypes. In a preferred embodiment, an full length antibody of the invention has a constant domain structure of an IgG type antibody.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. No. 5,202, 238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody". See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brüggemann, M., et al., Year Immunol. 7 (1993) 33-40). Human antibodies can also be produced in phage display libraries (Hoogenboom, H. R., and Winter, G. J., Mol. Biol. 227 (1992) 381-388; Marks, J. D., et al., J. Mol. Biol. 222 (1991) 581-597). The techniques of Cole, S. P. C., et al., and Boerner, P., et al., are also available for the preparation of human monoclonal antibodies (Cole, S. P. C., et al., Monoclonal Antibodies and Cancer Therapy, Alan R. Liss, (1985) 77-96); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a HEK293 cells, and CHO or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, E. A., et al., Sequences of Proteins of Immunological Interest, 5th ed., Public Health Service, National Institutes of Health, Bethesda, Md. (1991).

As used herein, the term "binding" or "specifically binding" refers to the binding of the antibody to an epitope of the antigen in an in vitro assay, preferably in an plasmon resonance assay (BIAcore, GE-Healthcare Uppsala, Sweden) with purified wild-type antigen. The affinity of the binding is defined by the terms ka (rate constant for the association of the antibody from the antibody/antigen complex), $k_D$ (dissociation constant), and $K_D$ ($k_D$/ka). Binding or specifically binding means a binding affinity ($K_D$) of $10^{-8}$ M or less, e.g. $10^{-8}$ M to $10^{-13}$ M, preferably $10^{-9}$ M to $10^{-13}$ M. Thus, an bispecific antibody according to the invention is specifically binding to each antigen for which it is specific with a binding affinity ($K_D$) of $10^{-8}$ M or less, e.g. $10^{-8}$ M to $10^{-13}$ M, preferably $10^{-9}$ M to $10^{-13}$ M.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

In certain embodiments, an antibody is said to specifically bind an antigen when it preferentially recognizes its target antigen in a complex mixture of proteins and/or macromolecules.

The term "peptide linker" as used herein for final the antibody according to the invention denotes a peptide with amino acid sequences, which is preferably of synthetic origin. These peptide connectors according to invention are used to fuse the disulfide stabilized Fv fragment binding to the second antigen to the to the heavy chain C- or N-termini of the full length antibody to form the bispecific antibody according to the invention. Preferably said peptide linkers are peptides with an amino acid sequence with a length of at least 5 amino acids, preferably with a length of 10 to 100 amino acids, more preferably with a length of 25 to 50 amino acids. In one embodiment said peptide linker is e.g. (G×S)n or (G×S) nGm with G=glycine, S=serine, and (x=3, n=3, 4, 5 or 6, and m=0, 1, 2 or 3) (SEQ ID NOs:16 and 17, respectively) or (x=4, n=2, 3, 4, 5 or 6, and m=0, 1, 2 or 3) (SEQ ID NOs:18 and 19, respectively), preferably x=4 and n=2, 3, 4, 5 or 6, and m=0. In one embodiment "peptide linker" as used within the antibody according to the invention does not comprise a protease cleavage site. Each terminus of the peptide linker is conjugated to one polypeptide chain (e.g. a VH domain, a VL domain, an antibody heavy chain, an antibody light chain, a CH1-VH chain, etc.).

The term "peptide linker" as used for the intermediate antibody as described below (which is processed to the antibody according to the invention either during expression or after expression) denotes a peptide with amino acid sequences, which is e.g. of synthetic origin. Preferably said peptide linkers under are peptides with an amino acid sequence with a length of at least 5 amino acids, preferably with a length of 5 to 100, more preferably of 10 to 50 amino acids. Each terminus of the peptide linker is conjugated to one polypeptide chain (e.g. a VH domain, a VL domain, an antibody heavy chain, an antibody light chain, a CH1-VH chain, etc.).

One of the peptide linkers within the intermediate bispecific antibody a does not comprise a protease cleavage site and is identical to the peptide linker of the final bispecific antibody according to the invention as described above. In one embodiment said peptide linker without a protease cleavage site is e.g. (G×S)n or (G×S) nGm with G=glycine, S=serine, and (x=3, n=3, 4, 5 or 6, and m=0, 1, 2 or 3) (SEQ ID NOs:16 and 17, respectively) or (x=4, n=2, 3, 4, 5 or 6, and m=0, 1, 2 or 3) (SEQ ID NOs:18 and 19, respectively), preferably x=4 and n=2, 3, 4, 5 or 6, and m=0.

The other peptide linker of the intermediate antibody as described below comprises a protease cleavage site, which is cleavable either during expression (e.g. by furin) or after expression (/and purification) e.g. In general a protease cleavage site within a peptide linker is an amino acid sequence or motif which is cleaved by a protease. Natural or artificial protease cleavage sites for different proteases are described e.g. in Database, Vol. 2009, Article ID bap015, doi:10.1093/database/bap015 and the referred MEROPS peptide database (see worldwide web at merops.sanger.ac.uk/). Furin specific protease cleavage sites are e.g. QSSRHRRAL (Furin specific protease cleavage site variant 1—FS1 of SEQ ID NO. 13), OR LSHRSKRSL (Furin specific protease cleavage site variant 2—FS2 of SEQ ID NO. 14). PreScission specific protease cleavage sites are e.g. QSSRHRRAL (PreScission specific protease cleavage site of SEQ ID NO. 15) LEVLFQGP.

Furin is a protein that in humans is encoded by the FURIN gene and belongs to the endo peptidases (Endopeptidases: serine proteases/serine endopeptidases (EC 3.4.21)). It was named furin because it was in the upstream region of an oncogene known as FES. The gene was known as FUR (FES Upstream Region) and therefore the protein was named furin. Furin is also known as PACE (Paired basic Amino acid Cleaving Enzyme). The protein encoded by this gene is an enzyme which belongs to the subtilisin-like proprotein convertase family. The members of this family are proprotein convertases that process latent precursor proteins into their biologically active products. This encoded protein is a calcium-dependent serine endoprotease that can efficiently cleave precursor proteins at their paired basic amino acid processing sites. Some of its substrates are: proparathyroid hormone, transforming growth factor beta 1 precursor, proalbumin, pro-beta-secretase, membrane type-1 matrix metalloproteinase, beta subunit of pro-nerve growth factor and von Willebrand factor. A furin-like proprotein convertase has been implicated in the processing of RGMc (also called hemojuvelin Hemojuvelin), a gene involved in a severe iron-overload disorder called juvenile hemochromatosis. Both the Ganz and Rotwein groups demonstrated that furin-like proprotein convertases (PPC) are responsible for conversion of 50 kDa HJV to a 40 kDa protein with a truncated COOH-terminus, at a conserved polybasic RNRR (SEQ ID NO: 20) site. This suggests a potential mechanism to generate the soluble forms of HJV/hemojuvelin (s-hemojuvelin) found in the blood of rodents and humans. Furin is present in endocytic and secretory vesicles, in the trans-Golgi network and in some cases on cell surfaces of many mammalian cells (e.g. HEK293, CHO). Its recognition sites frequently contain the motif RXK/RR which are present in a variety of secreted precursor proteins such as pro-TGFβ1 or pro-van Willebrand factor. Therefore, we selected these recognition sequences for generating two furin site containing connector sequences (Furin specific protease cleavage site variant 1—FS1 of SEQ ID NO:13 and Furin specific protease cleavage site variant 2—FS2 of SEQ ID NO:14.

PreScission Protease (GE Healthcare Catalogue No. 27-0843-01) is a genetically engineered fusion protein consisting of human rhinovirus 3C protease and GST. This protease was specifically designed to facilitate removal of the protease by allowing simultaneous protease immobilization and cleavage of GST fusion proteins produced from the pGEX-6P vectors pGEX-6P-1, pGEX-6P-2, and pGEX-6P-3; see pGEX Vectors (GST Gene Fusion System). PreScission Protease specifically cleaves between the Gln and Gly residues of the recognition sequence of LeuGluValLeuPheGln/GlyPro (SEQ ID NO: 15) (Walker, P. A., et al., BIO/TECHNOLOGY 12, (1994) 601-605; Cordingley, M. G., et al., J. Biol. Chem. 265 (1990) 9062-9065).

The bispecific antibodies according to the invention have valuable characteristics such as biological or pharmacological activity, pharmacokinetic properties. They can be used e.g. for the treatment of diseases such as cancer.

In a further embodiment the bispecific antibody according to the invention is characterized in specifically binding to ErbB3 and c-Met.

The term "constant region" as used within the current applications denotes the sum of the domains of an antibody other than the variable region. The constant region is not involved directly in binding of an antigen, but exhibit various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions (CL) which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see e.g. Johnson, G., and Wu, T. T., Nucleic Acids Res. 28 (2000) 214-218; Kabat, E. A., et al., Proc. Natl. Acad. Sci. USA 72 (1975) 2785-2788).

While antibodies of the IgG4 subclass show reduced Fc receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antibody according to the invention has a reduced FcR binding compared to an IgG1 antibody and the full length parent antibody is in regard to FcR binding of IgG4 subclass or of IgG1 or IgG2 subclass with a mutation in S228, L234, L235 and/or D265, and/or contains the PVA236 mutation. In one embodiment the mutations in the full length parent antibody are S228P, L234A, L235A, L235E and/or PVA236. In another embodiment the mutations in the full length parent antibody are in IgG4 S228P and in IgG1 L234A and L235A.

The constant region of an antibody is directly involved in ADCC (antibody-dependent cell-mediated cytotoxicity) and CDC (complement-dependent cytotoxicity). Complement activation (CDC) is initiated by binding of complement factor C1q to the constant region of most IgG antibody subclasses. Binding of C1q to an antibody is caused by defined protein-protein interactions at the so called binding site. Such constant region binding sites are known in the state of the art and described e.g. by Lukas, T. J., et al., J. Immunol. 127 (1981) 2555-2560; Brunhouse, R. and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat).

The term "antibody-dependent cellular cytotoxicity (ADCC)" refers to lysis of human target cells by an antibody according to the invention in the presence of effector cells. ADCC is measured preferably by the treatment of a preparation of antigen expressing cells with an antibody according to the invention in the presence of effector cells such as freshly isolated PBMC or purified effector cells from buffy coats, like monocytes or natural killer (NK) cells or a permanently growing NK cell line.

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

Cell-mediated effector functions of monoclonal antibodies can be enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol. Rev. 163 (1998) 59-76; Wright, A., and Morrison, S. L., Trends Biotechnol. 15 (1997) 26-32). Umana, P., et al. Nature Biotechnol. 17 (1999) 176-180 and WO 99/154342 showed that overexpression in Chinese hamster ovary (CHO) cells of β(1,4)-N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R. L., et al., J. Biol. Chem. 276 (2001) 6591-6604; Shields, R. L., et al., J. Biol. Chem. 277 (2002) 26733-26740; Simmons, L. C., et al., J. Immunol. Methods 263 (2002) 133-147).

Methods to enhance cell-mediated effector functions of monoclonal antibodies are reported e.g. in WO 2005/044859, WO 2004/065540, WO2007/031875, Umana, P., et al., Nature Biotechnol. 17 (1999) 176-180, WO 99/154342, WO 2005/018572, WO 2006/116260, WO 2006/114700, WO 2004/065540, WO 2005/011735, WO 2005/027966, WO 1997/028267, US 2006/0134709, US 2005/0054048, US 2005/0152894, WO 2003/035835 and WO 2000/061739 or e.g. in Niwa, R., et al., J. Immunol. Methods 306 (2005) 151-160; Shinkawa, T., et al., J. Biol. Chem. 278 (2003) 3466-3473; WO 03/055993 and US 2005/0249722.

In one embodiment of the invention, the bispecific antibody is glycosylated (if it comprises an Fc part of IgG1, IgG2, IgG3 or IgG4 subclass, preferably of IgG1 or IgG3 subclass) with a sugar chain at Asn297 whereby the amount of fucose within said sugar chain is 65% or lower (Numbering according to Kabat). In another embodiment is the amount of fucose within said sugar chain is between 5% and 65%, preferably between 20% and 40%. In an alternative embodiment, the amount of fucose is 0% of the oligosaccharides of the Fc region at Asn297. "Asn297" according to the invention means amino acid asparagine located at about position 297 in the Fc region. Based on minor sequence variations of antibodies, Asn297 can also be located some amino acids (usually not more than ±3 amino acids) upstream or downstream of position 297, i.e. between position 294 and 300. In one embodiment the glycosylated antibody according to the invention the IgG subclass is of human IgG1 subclass, of human IgG1 subclass with the mutations L234A and L235A or of IgG3 subclass. In a further embodiment the amount of N-glycolylneuraminic acid (NGNA) is 1% or less and/or the amount of N-terminal alpha-1,3-galactose is 1% or less within said sugar chain.

The sugar chain show preferably the characteristics of N-linked glycans attached to Asn297 of an antibody recombinantly expressed in a CHO cell.

The term "the sugar chains show characteristics of N-linked glycans attached to Asn297 of an antibody recombinantly expressed in a CHO cell" denotes that the sugar chain at Asn297 of the full length parent antibody according to the invention has the same structure and sugar residue sequence except for the fucose residue as those of the same antibody expressed in unmodified CHO cells, e.g. as those reported in WO 2006/103100.

The term "NGNA" as used within this application denotes the sugar residue N-glycolylneuraminic acid.

Glycosylation of human IgG1 or IgG3 occurs at Asn297 as core fucosylated biantennary complex oligosaccharide glycosylation terminated with up to two Gal residues. Human constant heavy chain regions of the IgG1 or IgG3 subclass are reported in detail by Kabat, E. A., et al., Sequences of Proteins of Immunological Interest, 5th Ed. Public Health Service, National Institutes of Health, Bethesda, Md. (1991), and by Brüggemann, M., et al., J. Exp. Med. 166 (1987) 1351-1361; Love, T. W., et al., Methods Enzymol. 178 (1989) 515-527. These structures are designated as G0, G1 (α-1,6- or α-1,3-), or G2 glycan residues, depending from the amount of terminal Gal residues (Raju, T. S., Bioprocess Int. 1 (2003) 44-53). CHO type glycosylation of antibody Fc parts is e.g. described by Routier, F. H., Glycoconjugate J. 14 (1997) 201-207. Antibodies which are recombinantly expressed in non-glycomodified CHO host cells usually are fucosylated at Asn297 in an amount of at least 85%. The modified oligosaccharides of the full length parent antibody may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of said sugar within the sugar chain at Asn297, related to the sum of all glycostructures attached to Asn297 (e.g. complex, hybrid and high mannose structures) measured by MALDI-TOF mass spectrometry and calculated as average value (see e.g. WO 2008/077546). The relative amount of fucose is the percentage of fucose-containing structures related to all glycostructures identified in an N-Glycosidase F treated sample (e.g. complex, hybrid and oligo- and high-mannose structures, resp.) by MALDI-TOF.

The antibody according to the invention is produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (supernatant or cells after lysis). In one embodiment the host cells are mammalian cells selected from e.g. CHO cells, NS0 cells, SP2/0 cells, HEK293 cells, COS cells, PER.C6 cells, preferably HEK293 cells or CHO cells. General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

The bispecific antibodies according to the invention are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the bispecific antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

One embodiment of the invention is the trivalent, bispecific antibody according to the invention for the treatment of cancer.

Another aspect of the invention is said pharmaceutical composition for the treatment of cancer.

Another aspect of the invention is the use of an antibody according to the invention for the manufacture of a medicament for the treatment of cancer.

Another aspect of the invention is method of treatment of patient suffering from cancer by administering an antibody according to the invention to a patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

As used herein, the terms "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F. L., and van der Eb, A. J., Virology 52 (1973) 456-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S. N, et al., PNAS 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The following examples, sequence listing and figures are provided to aid the understanding of the present invention, the true scope of which is set forth in the appended claims. It is understood that modifications can be made in the procedures set forth without departing from the spirit of the invention.

Description of the Amino Acid Sequences

SEQ ID NO:1 Her3/MetSS_KHSS_FS1-HC1 (SS_KnobsHC1_VHcMet)
SEQ ID NO:2 Her3/MetSS_KHSS_FS1-HC2 (SS_HolesHC2_VLcMet_FS1)
SEQ ID NO:3 Her3/MetSS_KHSS_FS1-LC (Her3clone29_KO1-LC)
SEQ ID NO:4 Her3/MetSS_KHSS_FS2-HC1 (SS_KnobsHC1_VHcMet)
SEQ ID NO:5 Her3/MetSS_KHSS_FS2-HC2 (SS_HolesHC2_VLcMet_FS2)
SEQ ID NO:6 Her3/MetSS_KHSS_FS2-LC (Her3clone29_KO1-LC)
SEQ ID NO:7 Her3/MetSS_KHSS_PreSci-HC1 (SS_KnobsHC1_VHcMet)
SEQ ID NO:8 Her3/MetSS_KHSS_PreSci-HC2 (SS_HolesHC2_VLcMet_PreSci)
SEQ ID NO:9 Her3/MetSS_KHSS_PreSci-LC (Her3clone29_KO1-LC)
SEQ ID NO:10 Her3/MetSS-3C-FS1-HC1 (SS_KnobsHC1_VHcMet)
SEQ ID NO:11 Her3/MetSS-3C-FS1-HC2 (SS_HolesHC2_VLcMet_FS1)
SEQ ID NO:12 Her3/MetSS-3C-FS1-LC (Her3clone29_KO1-LC)
SEQ ID NO:13 Furin specific protease cleavage site variant 1—FS1
SEQ ID NO:14 Furin specific protease cleavage site variant 2—FS2
SEQ ID NO:15 PreScission specific protease cleavage site Experimental Procedure

EXAMPLES

Recombinant DNA Techniques

Standard methods were used to manipulate DNA as described in Sambrook, J., et al., Molecular cloning: A laboratory manual; Cold Spring Harbor Laboratory Press, Cold Spring Harbor, N.Y., 1989. The molecular biological reagents were used according to the manufacturer's instructions.

DNA and Protein Sequence Analysis and Sequence Data Management

General information regarding the nucleotide sequences of human immunoglobulins light and heavy chains is given in: Kabat, E. A. et al., (1991) Sequences of Proteins of Immunological Interest, Fifth Ed., NIH Publication No 91-3242. Amino acids of antibody chains are numbered according to EU numbering (Edelman, G. M., et al., PNAS 63 (1969) 78-85; Kabat, E. A., et al., (1991) Sequences of Proteins of Immunological Interest, Fifth Ed., NIH Publication No 91-3242). The GCG's (Genetics Computer Group, Madison, Wis.) software package version 10.2 and Infomax's Vector NTI Advance suite version 8.0 was used for sequence creation, mapping, analysis, annotation and illustration.

DNA Sequencing

DNA sequences were determined by double strand sequencing performed at SequiServe (Vaterstetten, Germany) and Geneart AG (Regensburg, Germany).

Gene Synthesis

Desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of the subcloned gene fragments was confirmed by DNA sequencing. Where appropriate and or necessary, 5'-BamHI and 3'-XbaI restriction sites where used. All constructs were designed with a 5'-end DNA sequence coding for a leader peptide, which targets proteins for secretion in eukaryotic cells.

Construction of the Expression Plasmids

A Roche expression vector was used for the construction of all heavy VH/or VL fusion protein and light chain protein encoding expression plasmids. The vector is composed of the following elements:

a hygromycin resistance gene as a selection marker,
an origin of replication, oriP, of Epstein-Barr virus (EBV),
an origin of replication from the vector pUC18 which allows replication of this plasmid in E. coli
a beta-lactamase gene which confers ampicillin resistance in E. coli,
the immediate early enhancer and promoter from the human cytomegalovirus (HCMV),
the human 1-immunoglobulin polyadenylation ("poly A") signal sequence, and
unique BamHI and XbaI restriction sites.

The immunoglobulin fusion genes were prepared by gene synthesis and cloned into pGA18 (ampR) plasmids as described. The pG18 (ampR) plasmids carrying the synthesized DNA segments and the Roche expression vector were digested with BamHI and XbaI restriction enzymes (Roche Molecular Biochemicals) and subjected to agarose gel electrophoresis. Purified heavy and light chain coding DNA segments were then ligated to the isolated Roche expression vector BamHI/XbaI fragment resulting in the final expression vectors. The final expression vectors were transformed into E. coli cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and sequence integrity confirmed by DNA sequencing.

Transient Expression of Immunoglobulin Variants in HEK293 Cells

Recombinant immunoglobulin variants were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1-2 \times 10^6$ viable cells/ml on the day of transfection. DNA-293Fectin™ complexes were prepared in Opti-MEM® I medium (Invitrogen, USA) using 325 µl of 293Fectin™ (Invitrogen, Germany) and 250 µg of heavy and light chain plasmid DNA in a 1:1 molar ratio for a 250 ml final transfection volume. "Knobs-into-hole" DNA-293fectin complexes were prepared in Opti-MEM® I medium (Invitrogen, USA) using 325 µl of 293Fectin™ (Invitrogen, Germany) and 250 µg of "Knobs-into-hole" heavy chain 1 and 2 and light chain plasmid DNA in a 1:1:2 molar ratio for a 250 ml final transfection volume. Antibody containing cell culture supernatants were harvested 7 days after transfection by centrifugation at 14000 g for 30 minutes and filtered through a sterile filter (0.22 µm). Supernatants were stored at −20° C. until purification.

Purification of Bispecific and Control Antibodies

Bispecific and control antibodies were purified from cell culture supernatants by affinity chromatography using Protein A-Sepharose™ (GE Healthcare, Sweden) and Superdex200 size exclusion chromatography. Briefly, sterile filtered cell culture supernatants were applied on a HiTrap ProteinA HP (5 ml) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. Antibody and antibody variants were eluted with 0.1 M citrate buffer, pH 2.8, and the protein containing fractions were neutralized with 0.1 ml 1 M Tris, pH 8.5. Then, the eluted protein fractions were pooled, concentrated with an Amicon Ultra centrifugal filter device (MWCO: 30 K, Millipore) to a volume of 3 ml and loaded on a Superdex200 HiLoad 120 ml 16/60 gel filtration column (GE Healthcare, Sweden) equilibrated with 20 mM Histidin, 140 mM NaCl, pH 6.0. Fractions containing purified bispecific and control antibodies with less than 5% high molecular weight aggregates were pooled and stored as 1.0 mg/ml aliquots at −80° C.

Analysis of Purified Proteins

The protein concentration of purified protein samples was determined by measuring the optical density (OD) at 280 nm, using the molar extinction coefficient calculated on the basis of the amino acid sequence. Purity and molecular mass of bispecific and control antibodies were analyzed by SDS-PAGE in the presence and absence of a reducing agent (5 mM 1,4-dithiotreitol) and staining with Coomassie brilliant blue). The NuPAGE® Pre-Cast gel system (Invitrogen, USA) was used according to the manufacturer's instruction (4-20% Tris-Glycine gels). The aggregate content of bispecific and control antibody samples was analyzed by high-performance SEC using a Superdex 200 analytical size-exclusion column (GE Healthcare, Sweden) in 200 mM $KH_2PO_4$, 250 mM KCl, pH 7.0 running buffer at 25° C. 25 µg protein were injected on the column at a flow rate of 0.5 ml/min and eluted isocratically over 50 minutes. For stability analysis, concentrations of 1 mg/ml of purified proteins were incubated at 4° C. and 40° C. for 7 days and then evaluated by high-performance SEC. The integrity of the amino acid backbone of reduced bispecific antibody light and heavy chains was verified by NanoElectro spray Q-TOF mass spectrometry after removal of N-glycans by enzymatic treatment with Peptide-N-Glycosidase F (Roche Molecular Biochemicals).

Example 1

Design of Bispecific Antibodies According to the Invention

We generated in a first attempt derivatives based on a full length antibody binding to a first antigen that carries one additional Fv as $2^{nd}$ binding moiety specific for the second antigen (see FIG. 2a). We introduced interchain disulfides between VHCys44 and VLCys100 ref. see p17-18 A-M. The VHCys44 of the dsFv was fused to the CH3 domain of the first heavy chain of the full length antibody, the corresponding VLCys100 module was fused to CH3 domain of the of the second heavy chain of the full length antibody.

It was previously shown that dsFvs can assemble from separately expressed modules with reasonable yields by bacterial inclusion body refolding or periplasmic secretion (WO 94/029350, U.S. Pat. No. 5,747,654, Rajagopal, V., et al., Prot. Engin. 10 (1997) 1453-1459; Reiter, Y., et al., Nature Biotechnology 14 (1996) 1239-1245; Reiter, Y., et al., Protein Engineering; 8 (1995) 1323-1331; Webber, K. O., et al., Molecular Immunology 32 (1995) 249-258; Reiter, Y., et al., Immunity 2 (1995) 281-287; Reiter, Y., et al., JBC 269 (1994) 18327-18331; Reiter, Y., et al., Inter. J. of Cancer 58 (1994) 142-149; Reiter, Y., Cancer Res. 54 (1994) 2714-2718).

Figure 2D:
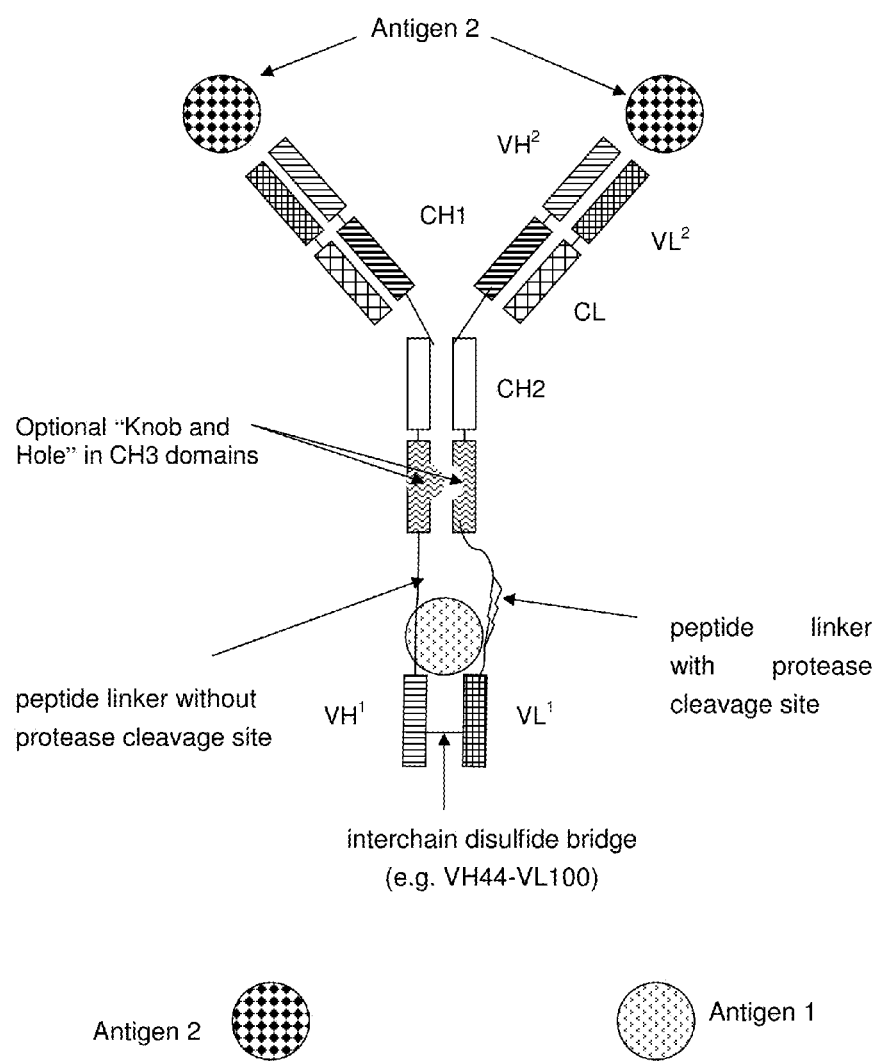
FIG. 2D Exemplary schematic representation of an intermediate for a bispecific antibody according to the invention as shown in FIG. 2A.
Figure 3A:
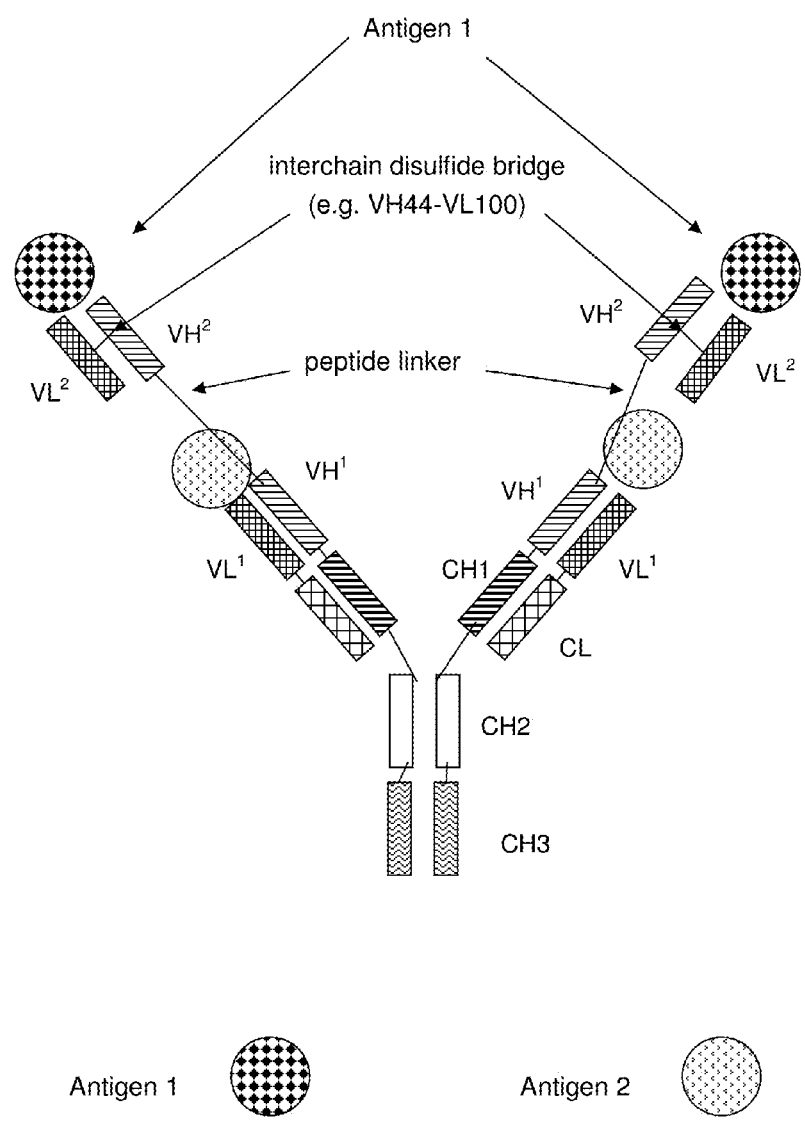
FIG. 3A-B Schematic representation of a tetravalent bispecific antibody according to the invention, comprising a full length antibody (with optional knobs into holes modifications in the CH3 domains) which specifically binds to a first antigen 1 and to whose N-terminus a disulfide-stabilized Fv fragment specifically binding to a second antigen 2, is fused via the C-terminus of either the VH$^2$ (FIG. 3A) or the VL$^2$ (FIG. 3B) of the disulfide-stabilized Fv fragment.
Figure 3B:
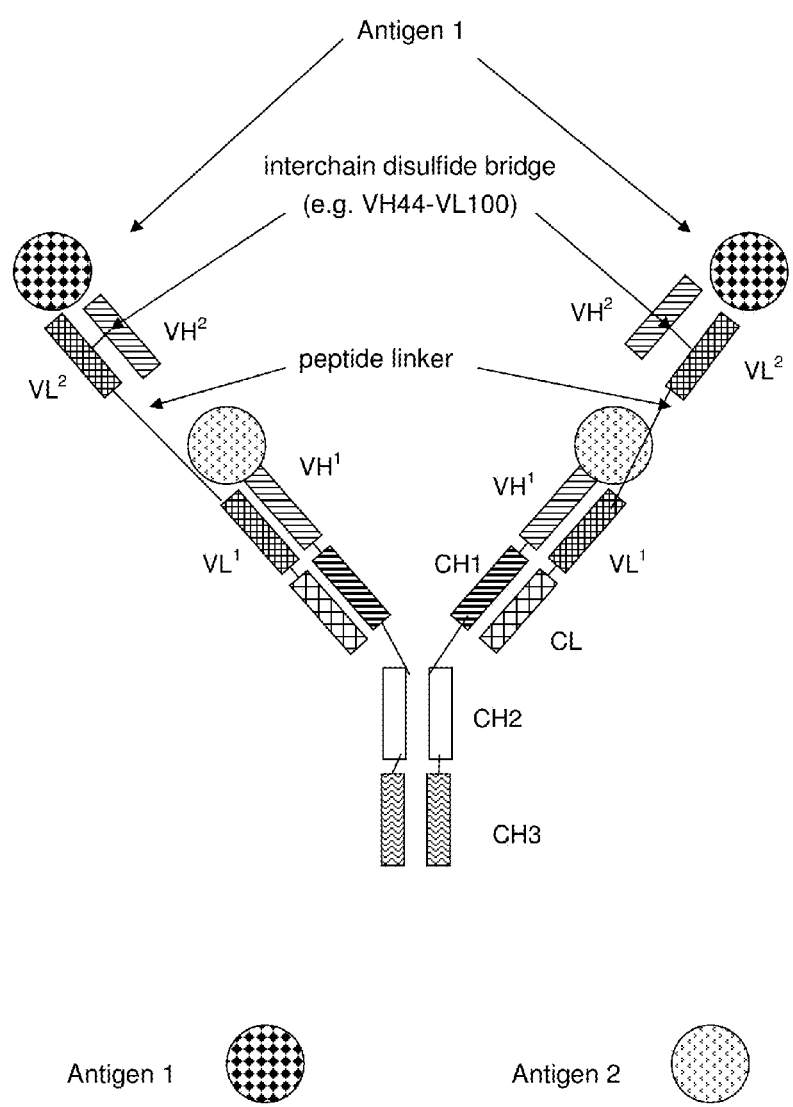
Figure 3C:
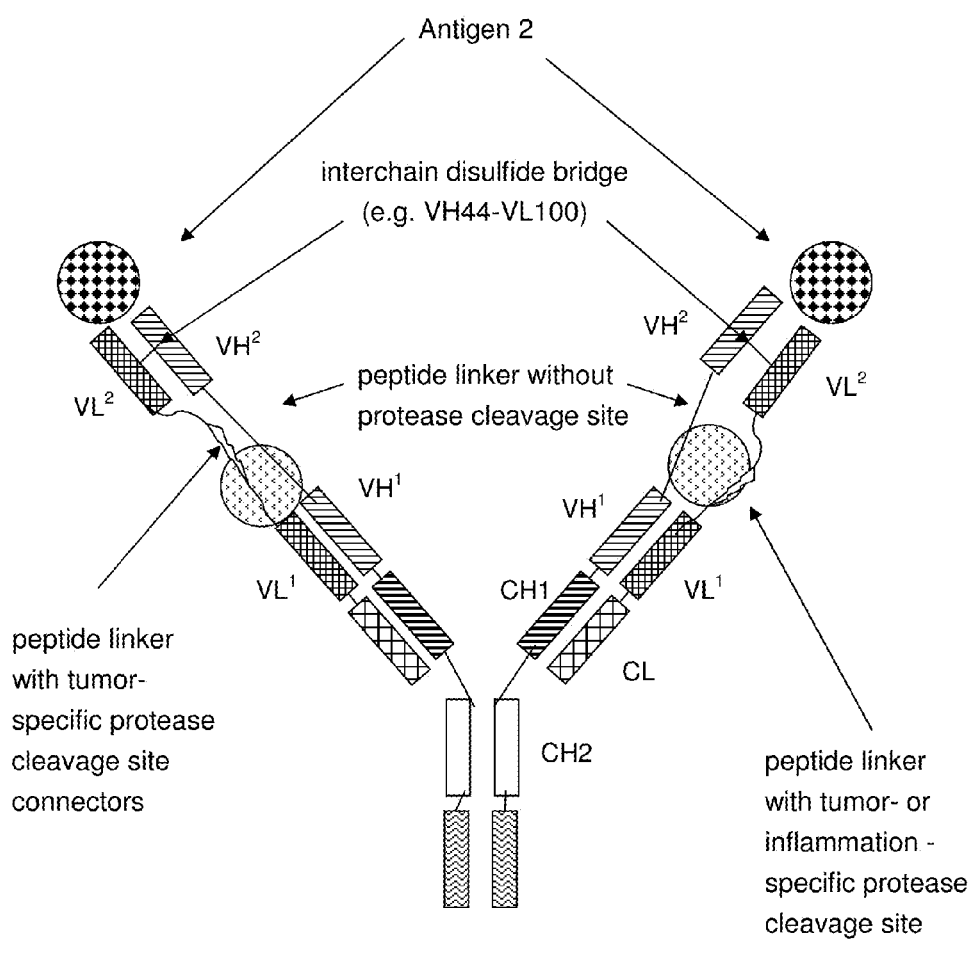
FIG. 3C Exemplary schematic representation of an intermediate for a bispecific antibody according to the invention as shown in FIG. 3A.
Figure 3D:
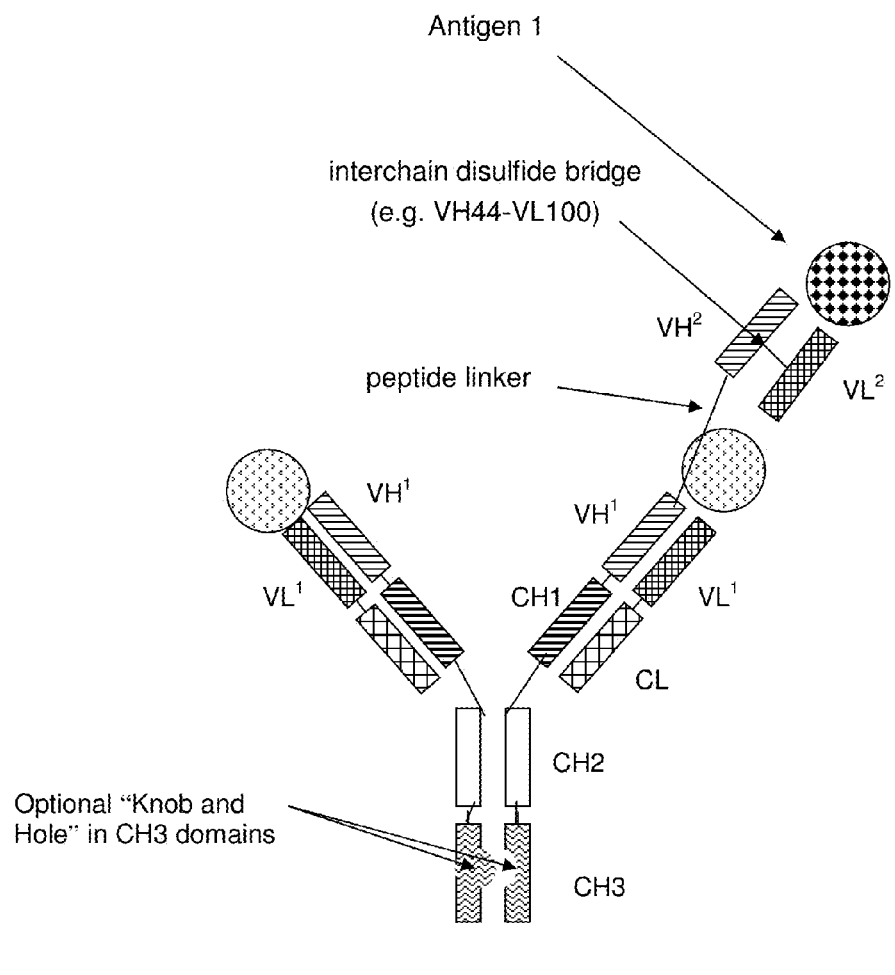
FIG. 3D-E Schematic representation of a trivalent, bispecific antibody according to the invention, comprising a full length antibody (with optional knobs into holes modifications in the CH3 domains) which specifically binds to a first antigen 1 and to whose N-terminus a disulfide-stabilized Fv fragment specifically binding to a second antigen 2, is fused via the C-terminus of either the VH2 (FIG. 3D) or the VL2 (FIG. 3E) of the disulfide-stabilized Fv fragment.
Figure 3E:
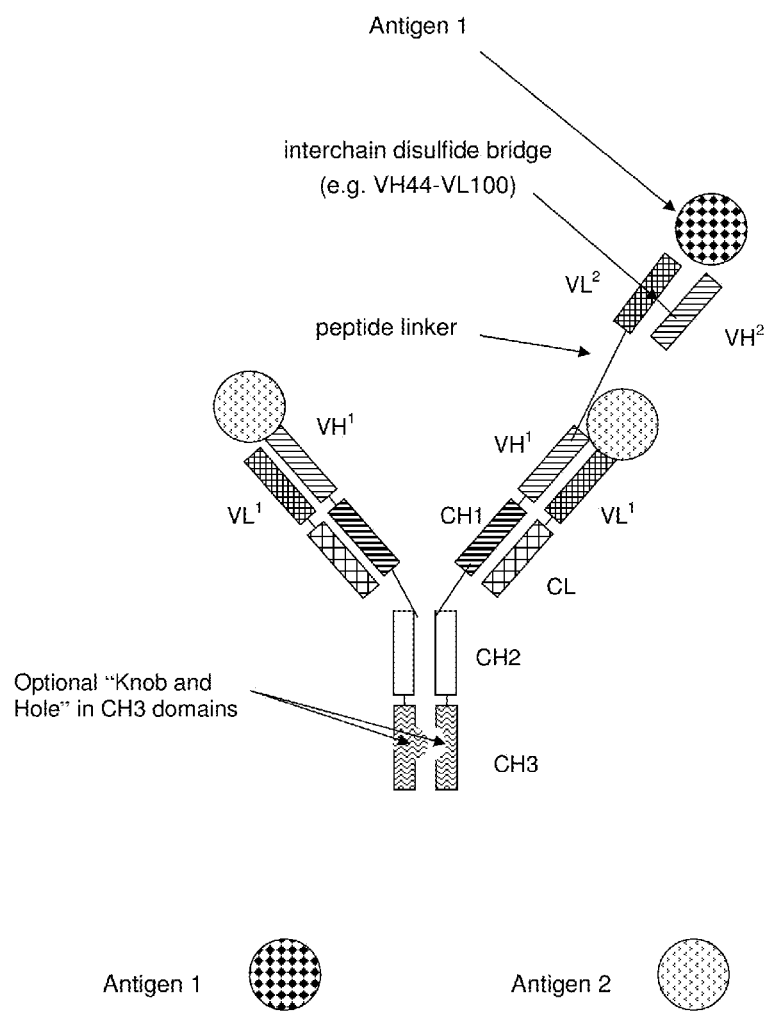
Figure 4A:
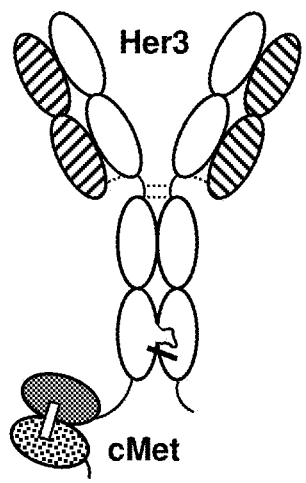
Figure 4B:
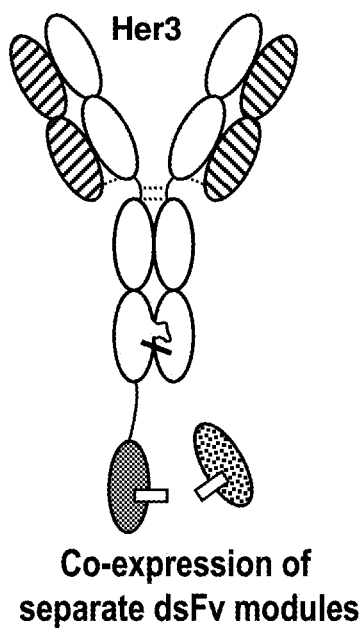

One bottleneck for production of linkerless dsFvs in mammalian secretion systems may be ineffective assembly of VH and VL domains without the help of chaperons: dsFv components do not contain constant regions that are recognized by BIP. (see FIG. 4b) To overcome this limitation, we approached the assembly of VH and VL domains via an intermediate (FIG. 4c). Therefore we connected one component (VH or VL) of the dsFv via a connector peptide to the C-terminus of one H-chain, and the corresponding other component to the C-terminus of the second H-chain by another connector peptide, which however contains on or more protease cleavage site which can be either cleaved during expression in cells (e.g. by furin) or which can be cleaved after purification in vitro. Examples of intermediate bispecific antibodies are shown in FIG. 2d (for antibodies as shown in FIG. 2a).

The rationale for this approach was that the effective dimerization of H-chains brings together and facilitates heterodimerization of dsFv components. To reduce nonproductive assembly of molecules containing 2 VH or 2 VL modules, complementary knobs-into-holes mutations were set into the H-chains of the IgG. These mutations were devised by Merchant, A. M., et al., Nat Biotechnol 16 (1998) 677-681 and Ridgway, J. B., et al., Protein Eng 9 (1996) 617-621 to force heterodimerization of different H-chains and consist of a T366W mutation in one H-chain chain and T366S, L368A and Y407V mutations in the corresponding other chain. Our design for generation of dsFv-containing bispecifics had the 'knobs' on the CH3 domain that was fused to VHCys44 and the complementary 'holes' were introduced into the H-chain that carried VLCys100.

Both components of the heterodimeric dsFv are tethered to CH3. This simultaneous attachment of VH and VL at their N-termini to bulky CH3 domains does not affect the structure of the Fv. However, it can restrict the accessibility towards the antigen depending (e.g. depending on the linker length or the respective antigenstructure) because the CDR region points into the direction where CH3 is located. In addition, tethering at two connection points leaves only very limited freedom for the Fv to rotate or move next to the CH3. Because of that antigens need to squeeze between CH3 and Fv. This may affect accessibility to antigen and reduce affinity, which we indeed observed for the double-connected dsFv moiety of the bispecific antibody (see SPR data in Table 2. Consistant with antigen accessibility issues due to steric hindrance, affinity determination revealed significantly reduced on-rate for the double-tethered dsFv. Nevertheless, structural integrity of the Fv appears to be intact because once the antigen has bound, the off-rate is the same as that of the unmodified antibody. The affinity values for binding of the IgG-like accessible arms of the bispecific antibody (which expectedly have full affinity), as well as for the additional double-tethered dsFv are listed in Table 2. We use the term 'restricted or reduced binding mode' for dsFv modules with reduced on-rate due to the steric hindrance after double-tethering.

Exemplarily, based on the following intermediate antibody sequences, we could express recombinantly by cleaving one linker processed after expression and purification expression antibodies according to the invention which are connected only via one domain of the disulfide-stabilized Fv fragment to the full length antibody (see also FIG. 2 and the experimental description below):

| Bispecific intermediatedantibody | Heavy chain construct without protease cleavage site | Heavy chain construct with protease cleavage site | Light chain (2x) |
|---|---|---|---|
| Her3/MetSS_KHSS_PreSci (protease site cleavage = prescission cleavage site) | SEQ ID NO: 7 | SEQ ID NO: 8 | SEQ ID NO: 9 |

Exemplarily, based on the following intermediate antibody sequences, we could express recombinantly by cleaving one linker processed during expression antibodies according to the invention which are connected only via one domain of the disulfide-stabilized Fv fragment to the full length antibody (see also FIG. 2 and the experimental description below):

| Bispecific intermediatedantibody | Heavy chain construct without protease cleavage site | Heavy chain construct with protease cleavage site | Light chain (2x) |
|---|---|---|---|
| Her3/MetSS_KHSS_FS1 (protease cleavage = furin cleavage site-variant1) | SEQ ID NO: 1 | SEQ ID NO: 2 | SEQ ID NO: 3 |
| Her3/MetSS_KHSS_FS2 (protease cleavage site = furin cleavage site-variant 2) | SEQ ID NO: 4 | SEQ ID NO: 5 | SEQ ID NO: 6 |

Figure 5:
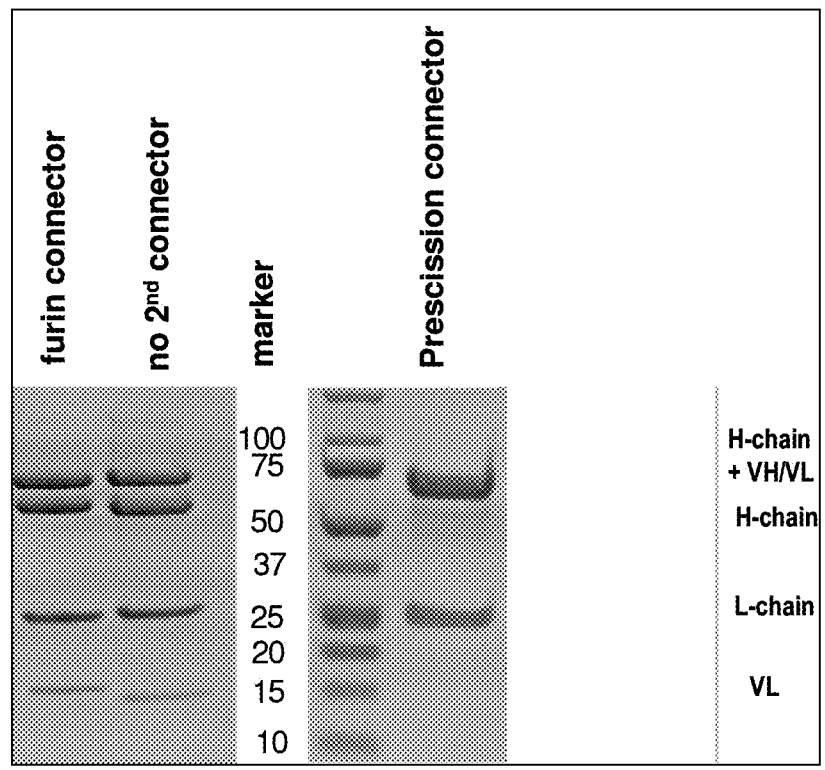
FIG. 5: Expression and purification of bispecific dsFv-containing antibody derivatives
- Reducing SDS Page of protein preparations after Protein-A and SEC purification.
Figure 6A:
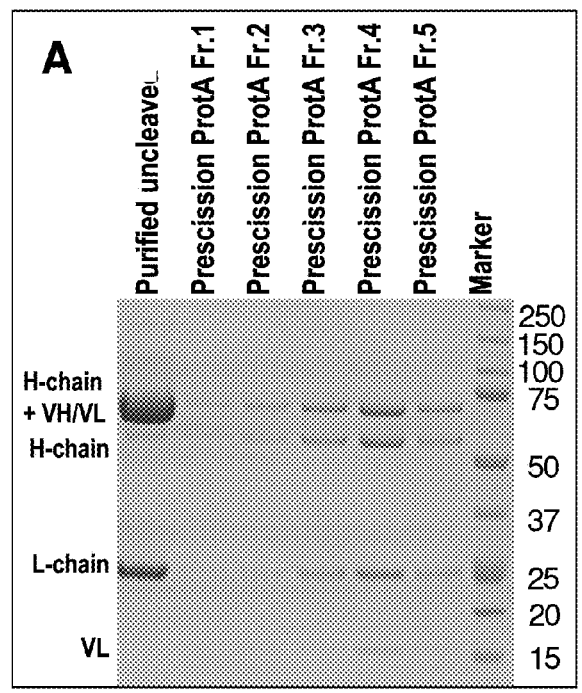
FIG. 6A-B: Reduced binding affinity before protease cleavage:
- Reducing SDS-Page of bispecific antibody derivatives before and after protease cleavage.
- 6A: The bispecific antibodies according to the invention containing a Prescission cleavage site are generated with reduced binding affinity and become activated upon exposure to Prescission protease.
- 6B: The bispecific antibodies according to the invention containing a furin cleavage site are generated with reduced binding affinity and become subsequently activated upon exposure to furin.

Example 2 a) Expression and Purification of Bispecific Antibodies According to the Invention in a Two-Step or One-Step Process Two-Step Process:
1. Step: Transient Expression Transient expression was applied for production of secreted bispecific antibody derivatives. Plasmids encoding L-chains and modified H-chains were co-transfected into HEK 293 suspension cells. Culture supernatants containing secreted antibody derivatives were harvested one week later. These supernatants could be frozen and stored at −20 C before purification without affecting yields. The bispecific antibodies were purified from supernatants by Protein A and SEC in the same manner as conventional IgGs which proves that they were fully competent to bind Protein A. Expression yields within cell culture supernatants were lower than transiently expressed unmodified antibodies but still within a reasonable range. After completion of all purification steps, yields between 4 and 10 mg/L of homogenous protein were obtained. Despite having no peptide linker between VH and VL of the additional dsFv moiety, stability analyses revealed no indication for unusual concentration- or temperature dependent disintegration or aggregation. The proteins were stable and freeze-thaw was well tolerated. Size, homogeneity, and composition of trivalent bispecific antibody derivatives and their components under reducing and non-reducing conditions are shown in FIGS. 5 and 6. The identity and composition of each protein was confirmed by mass spectrometry (Table 1).

Double-tethering of dsFv components to CH3-domains reduces antigen access and thereby inactivates the functionality of the dsFv. Free rotation of Fvs around one connector peptide would most likely dramatically increase access to antigen, but the fusion of dsFv at two connection points does not permit a large degree of flexibility or rotation. To re-activate the inactivated binding functionality of such restricted dsFvs moieties, we introduced specific protease recognition sites into one of the connector peptides (schematically shown in FIG. 4d). Our rationale for that approach was to utilize proteolytic cleavage for the release of just one of the 2 connections. Upon proteolytic processing, the dsFv would still be covalently linked to the IgG backbone of the bispecific antibody by its other connector. But in contrast to double-connection, attachment at just one flexible connection point can improve flexibility allow free rotation to facilitate access to antigen. FIG. 1b shows different connector sequences that we applied to enable processing by proteases. The standard non-cleavable connector is composed of six Gly4Ser-repeats (SEQ ID NO: 21), a motif that has been frequently used for generation fusion proteins composed of different domains. For proteolytic processing, we introduced specific recognition sequences into the central region of this connector:

One connector contains a site that is cleaved by the Prescission protease. This protease can unleash functionality of Fv modules that are expressed in restricted form. PreScission Protease (GE Healthcare Catalogue No. 27-0843-01) is a genetically engineered fusion protein consisting of human rhinovirus 3C protease and GST. This protease was specifically designed to facilitate removal of the protease by allowing simultaneous protease immobilization and cleavage of GST fusion proteins produced from the pGEX-6P vectors pGEX-6P-1, pGEX-6P-2, and pGEX-6P-3; see *pGEX Vectors* (*GST Gene Fusion System*). PreScission Protease specifically cleaves between the Gln and Gly residues of the recognition sequence of LeuGluValLeuPheGln/GlyPro (SEQ ID NO: 15) (Walker, P. A., et al. BIO/TECHNOLOGY 12, (1994) 601-605; Cordingley, M. G. et al. J. Biol. Chem. 265, (1990) 9062-9065.)

restricted form and activate them afterwards as one step in downstream processing. This application has advantages in cases where high activity of binding modules poses a problem for expression, e.g. because full functionality would interfere with cell growth, with secretion processes, or is toxic to producer cells.

As an example for this setting, we expressed and purified a Her3-cMet bispecific antibody carrying a restricted cMet dsFv module, and subsequently unleashed the dsFv activity by processing with Prescission. FIG. 5 shows that after expression and purification from cell culture supernatants, bispecific Her3-cMet entities are obtained which have the components of the dsFv tightly connected to H-chains. Reduced SDS-PAGE show (in addition to the standard L-chain of the Her3-entity), the presence of a protein (double-)band at the height of 65 kD. This band represents the H-chains (50 kd) that carry additional connector peptides (2 kd) and VH or VL domains (13 kD) at their C-termini.

The affinity (prior to Prescission processing) of these bispecific molecules towards their fully accessible binding entities to Her 3 is the same as that of the wildtype antibody (Table 1). In contrast, the affinity of the restricted dsFv moiety towards cMet is compromised due to steric hindrance. Biacore analyses show a >20 fold reduced affinity than that of the Wildtype Fab (Table 1).

TABLE 1

Exemplary expression and purification of bispecific antibody derivatives

| Molecule | Connector | Processing | Yield (mg/L) | SDS-PAGE & Mass Spec |
|---|---|---|---|---|
| Her3/MetSS_KHSS_PreSci | Prescission site | none | 4-20 mg/L | L + extended H |
| Her3/MetSS_KHSS_PreSci | Prescission site | PreScission |  | L + extended H + cleaved H + VL |
| Her3/MetSS_KHSS_F1 | Furin site-variant 1 | During expresseion | 4 mg/L | L + H + extended H + VL |

2. Step: Proteolytic Processing (Cleavage)

Processing with Prescission can be applied after or during purification.

One-Step Process:

To realize the proteolytic cleavage during the expression step we used linker sequences can be recognized and cleaved by Furin. Furin is a protease that is present in endosomal and secretory compartments and the trans-Glogi network of mammalian cells, incl. HEK293. We chose such protease sites to enable dsFv processing within the expression process. Bispecific entities carrying the restricted dsFv will encounter furin during secretion. Thereby, already cleaved fully functional proteins can made by the cells.

Bispecific Antibodies Containing a Prescission Site are Expressed in Restricted Form and can be Activated in Downstream Processing One application of bispecific antibody formats that contain restricted binding modules is to express them in Cleavage of the prescission site within the connector between CH3 and VL resolves the restriction of the dsFv and gives rise to molecules that have the dsFv attached to the IgG by only by one connector. Reducing SDS PAGE proves that after cleavage, one of the extended H-chains is converted to normal size (52 kd) and an additional VL domain of 13 k (see FIG. 6a). While cleaved, the molecule is still held together by a stable disulfide bond as shown by size exclusion chromatography and mass spectroscopy.

A comparison of affinities of restricted and processed forms of the bispecific antibody is listed in Table 2: as expected, processing at the dsFv moiety did not change the binding to the previously already fully accessible antigen Her3. On the other hand, resolution of steric hindrance by cleaving one connector greatly improved the on-rate of the linkerless dsFv module: the affinities of the unleashed dsFv were improved >30 fold and were fully restored to affinity levels of the parent antibody (Table 2).

TABLE 2

Binding affinity of bispecific antibody derivatives according to the invention
(and comparison with parent antibodies as well as, where possible (e.g. for
prescission sites), comparison with corresponding intermediates before protease cleavage)

|  | HER3 binding affinity (KD) | | | cMet binding affinity (KD) | | |
|---|---|---|---|---|---|---|
|  | ka (1/Ms) | kd (1/s) | KD (M) | ka (1/Ms) | kd (1/s) | KD (M) |
| Bispecific Antibody according to the invention | | | | | | |
| Her3_MetSS_KHSS_FS1 (protease cleavage during expression) | 1.65E+05 | 3.38E−04 | 2.05E−09 | 3.12E+04 | 1.88E−04 | 6.05E−09 |
| Her3_MetSS_KHSS_FS2 (protease cleavage during expression) | n.d. | n.d. | n.d. | 2.74E+04 | 1.93E−04 | 7.05E−09 |
| Her3-cMet-3C-FS1 (protease cleavage during expression) | 1.,63E+05 | 3.41E−04 | 2.09E−09 | 1.74E+04 | 3.,31E−04 | 1.,90E−08 |
| Her3_MetSS_KHSS_PreSci_digested (after purification and protease cleavage) | 1.76E+05 | 3.56E−04 | 2.02E−09 | 2.43E+04 | 2.03E−04 | 8.35E−09 |
| Intermediate for Bispecific Antibody according to the invention | | | | | | |
| Her3_MetSS_KHSS_PreSci (purified intermediate) | 1.72E+05 | 4.14E−04 | 2.40E−09 | 5.33E+02 | 1.97E−04 | 3.69E−07 |
| Parent monospecific Antibody | | | | | | |
| Parent cMet-Fab | — | — | — | 6.92E+04 | 1.59E−04 | 2.29E−09 |
| Parent Mab_Her3_001 clone 29 | 1.52E+05 | 3.60E−40 | 2.36E−09 | — | — | — |

Bispecific Antibodies Containing Furin Sites Become Effectively Processed During Expression and Display Full Functionality of the Linkerless dsFv Furin sites within connectors can be used for direct expression of bispecific antibodies containing linkerless dsFvs with unrestricted functionality. Furin is present in endocytic and secretory vesicles, in the trans-Golgi network and in some cases on cell surfaces of many mammalian cells (e.g. HEK293 as used within theses experiments). Its recognition sites frequently contain the motif RXK/RR which are present in a variety of secreted precursor proteins such as pro-TGFβ1 or pro-van Willebrand factor. Therefore, we selected these recognition sequences for generating two furin site containing connector sequences (Furin specific protease cleavage site variant 1—FS1 of SEQ ID NO:13 and Furin specific protease cleavage site variant 2—FS2 of SEQ ID NO:14.

Figure 6B:
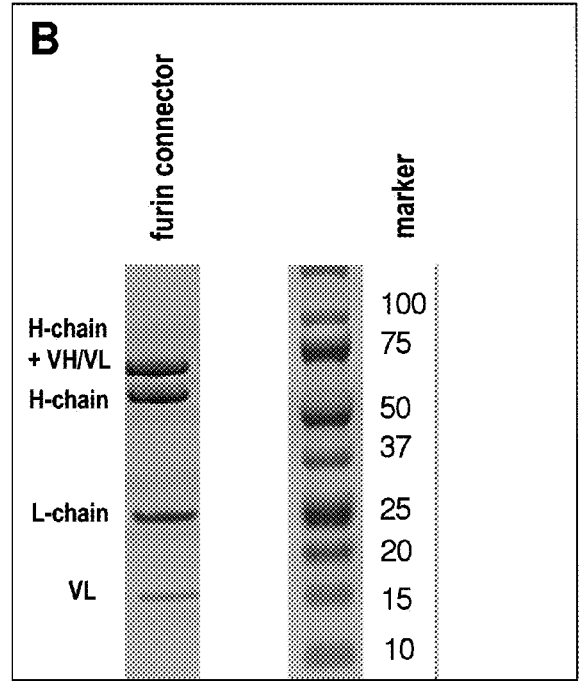

Because furin is present in the trans-Golgi network and in secretory vesicles, cleavage can occur within cells during the production. The expression yields of furin processed unrestricted and fully functional molecules that we obtained was similar to that observed for restricted molecules (Table 1), because the dsFvs become fully folded and assembled prior to encountering compartments with Furin activity. FIGS. 5 and 6b proves that after expression and purification molecules are obtained which are already quantitatively processed. Reducing PAGE shows (in addition to the standard <Her3> L-chain) one extended H-chain of 65 kD that carries the VH of the dsFv, and another H-chain that has been converted to normal size (52 kd) by furin. The additional VL domain of 13 kD is also detectable. Since the purification procedure involved ProteinA and SEC (both of which would not recover unlinked VL domains), detection of these domains indicate the generation of fully processed functional bispecifics. Size exclusion chromatography and mass spectroscopy further confirmed the fact that all domains are held together by stable disulfides (schematically shown in FIGS. 2 and 3).

Because the processing via Furin occurs during the expression process, the preparations obtained after purification should be composed of bispecific entities with fully active linkerless dsFvs in unleashed form. This could be confirmed by SPR analyses (Table 2). All binding entities of the bispecific antibody, those recognizing Her3 as well as the dsFv that binds cMet, have unrestricted binding capability. Their affinity to Her3 and cMet is comparable to that of unmodified antibodies or Fab (Table 2).

Application of Mass Spectrometry to Analyze Furin-Mediated Processing of Bispecific Antibody Derivatives During Expression in Mammalian Cells The bispecific antibody derivatives that we describe in this application are translated to protein as precursor forms. These need cleavage by furine within the secretory pathway of producer cells for conversion into an unrestricted format. To determine the degree of furin-mediated conversion of restricted precursor forms of the bispecific antibodies to unrestricted molecules, we applied mass spectrometry. This technology can be used to determine the exact molecular mass of proteins and protein fragments.

Prior to the mass spectrometric analysis, the antibodies were deglycosylated applying standard protocols using N-Glycosidase F in order to decrease spectral complexity and facilitate data interpretation. As a further measure to facilitate data interpretation, molecules to be analyzed were cleaved by IdeS protease into disulfide-bridged Fc and F(ab)$_2$ fragments. The fragments were subsequently reduced with TCEP to separate their different components to facilitate identification and characterization. Thereby, relevant furin cleavage events are detectable as defined masses of the deglycosylated and reduced IdeS-derived Fc fragments.

The samples were desalted and subsequently subjected to electrospray ionization (ESI) mass spectrometry on a Quadrupole Time-of-Flight instrument (Q-Star, (ABI, Darmstadt) or Maxis (Waters, Manchester). A NanoMate system (Triversa NanoMate System, Advion, Ithaka, USA) was used to introduce the samples into the ESI nanospray source. The samples were analyzed using standard MS protocols for deglycosylated and reduced antibodies providing a stable spray, proper desolvation and no fragmentation of the analytes. The mass spectra were acquired with scan durations of 5 seconds.

The results of these analyses indicate that the bispecific antibody derivatives that are translated as precursor forms are thereafter processed by furine within the secretory pathway of producer cells. The protein preparations Her3_MetSS_KHSS_FS1 and Her3_MetSS_KHSS_FS2 have two different furin recognition sequences inserted within their connectors (in heavy chain fusion proteins of SEQ ID NO:2 for FS1 and of SEQ ID NO:4 for FS2). In both preparations, complete processing by furin was observed and unprocessed precursor fragments (extended IdeS-Fc fragments) were not detectable. In addition, our mass analyses indicated further carboxyterminal processing of the furin-cleaved protein modules. The arginine and/or lysine residues that preceded the cleavage site and formed part of the furine recognition sequence were quantitatively removed from the furin-processed products.

Another protein preparation of a bispecific antibody derivative that we analyzed harbored a connector sequence of reduced length (Her3-cMet-3C-FS1).

| Bispecific intermediate antibody | Heavy chain construct without protease cleavage site | Heavy chain construct with protease cleavage site | Light chain (2x) |
|---|---|---|---|
| Her3/MetSS-3C-FS1 (protease cleavage = furin cleavage site-variant1) | SEQ ID NO: 10 | SEQ ID NO: 11 | SEQ ID NO: 12 |

In this preparation, again products of furin processing were unambiguously detected. Furthermore, and in the same manner as described above, arginine and/or lysine residues that preceded and formed part of the furine recognition sequence were also quantitatively removed from the furin-processing products. This preparation contained in addition to furin-processing products additional extended Fc fragments. This indicates that this protein batch contained still some unprocessed precursor molecules.

Figure 9:
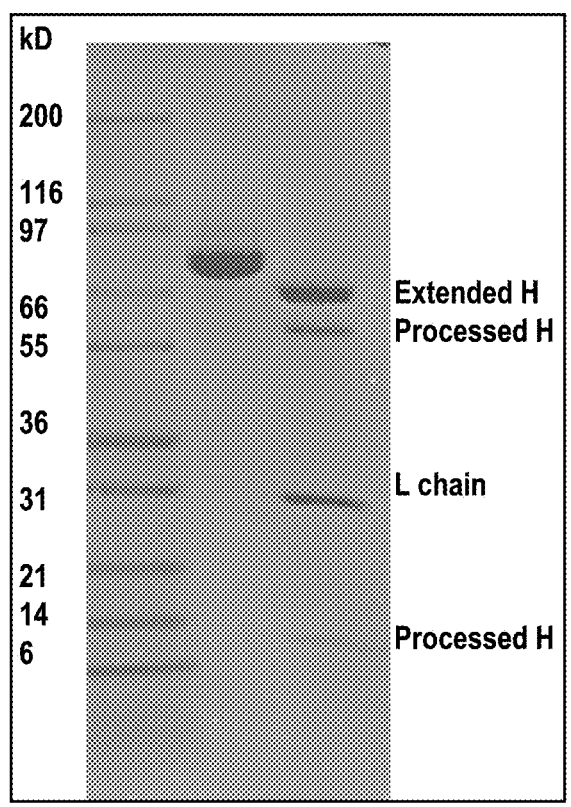
FIG. 9: reducing SDS PAGE analysis of Her3-cMet-3C-FS1 displays the presence of the products (52 kD, 12 kD) that were generated by furin processing.

To further analyze the degree of processing vs presence of unprocessed precursor molecules in this Her3-cMet-3C-FS1 preparation, SDS-PAGE analyses were performed under reducing conditions. The results of these analyses (FIG. 9) indicate a significant degree of furin processing also for this preparation: Furin cleavage converts only one of the extended H chain (63 kD) to a H-chain of normal size (50 kD) and releases a protein fragment of 12 kD. Both products of this processing process are clearly detectable.

The ratio between fully processed products and any remaining unprocessed precursor-material cannot be determined in an exact manner by this method because the complementary (uncleavable) extended H-chain locates at the same position in the gel as the precursor. However, the detectable amounts of processing products, especially the clear visualization of the 12 kD fragment (which due to its small size is much more difficult to visualize than larger protein fragments), indicate that quite effective processing has taken place even in this preparation.

Functionality of the Obtained Bispecific Antibodies According to the Invention

Figure 7:
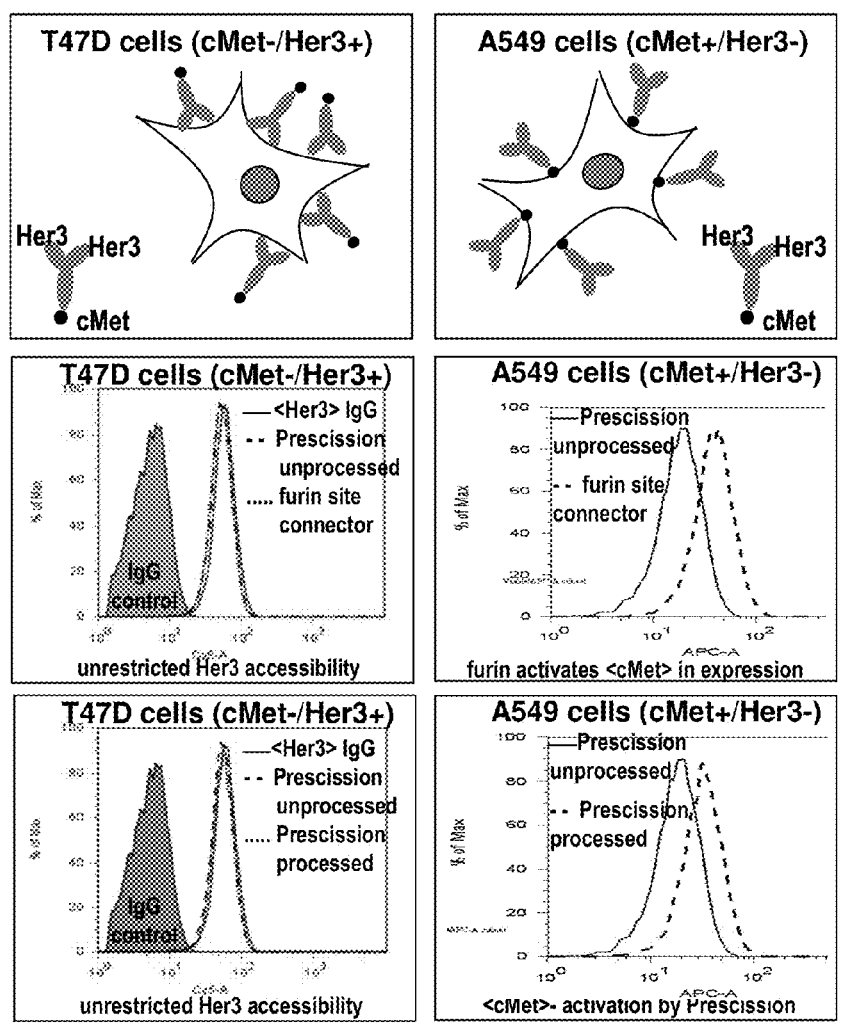
FIG. 7: Binding of restricted and unrestricted trivalent Her3-cMet bispecific antibodies to live cells.
- Binding of the bivalent unrestricted Her3-modules to Her3-expressing, cMet negative T47D cells is shown in the left panels.
- Binding of the different restricted cMet-modules to Her3-negative, cMet expressing A549 cells is shown in the right panels. Poor binding is observed for the restricted modules while unleashing by specific proteases leads to full binding and accumulation on cells.
Figure 8A:
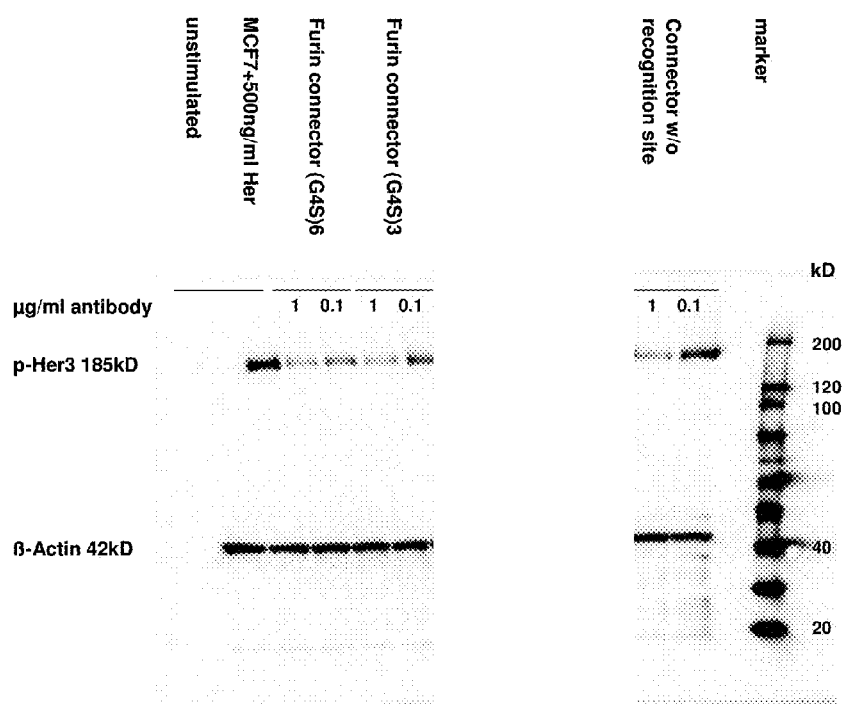
FIG. 8A-B: Inhibitory functionality of trivalent Her3-cMet entities in cellular signaling assays
- 8A: Western Blot that detects phosphorylated-Her3 demonstrates interference with signaling by the unrestricted Her3-entity. (G4S)3, SEQ ID NO:24; (G4S)6, SEQ ID NO:21.
- 8B: ELISA that detects phosphorylated-ACT demonstrates effective interference with HGF/c-Met signaling by the unrestricted cMet-entity while the same molecule in restricted form has lower activity. (G4S)3, SEQ ID NO:24; (G4S)6, SEQ ID NO:21.
Figure 8B:
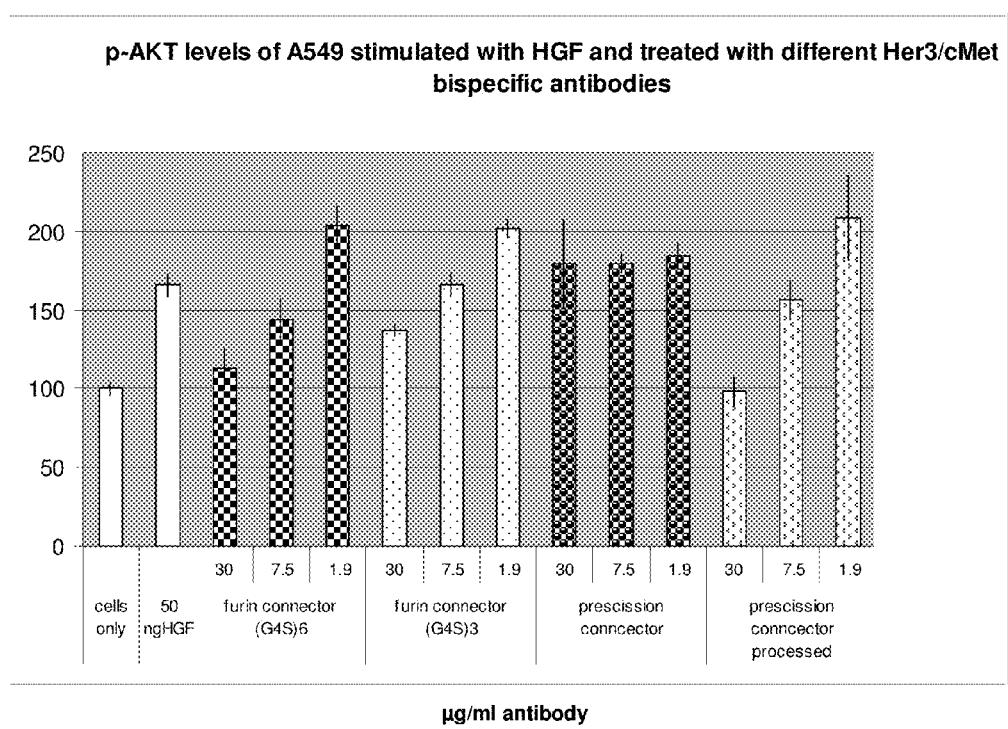

The functionality of the obtained bispecific antibodies according to the invention (which are connected only via one domain of the disulfide-stabilized Fv fragment to the full length antibody) was further investigated in cellular assays: FACS experiments (FIG. 7) showed that unrestricted arms of bispecific antibodies specifically bound to Her3-expressing cancer cells and caused accumulation on such cells. The binding of restricted versus unleashed dsFv cMet modules was analysed by FACS on cMet expressing A549 cells in a similar manner. FIG. 7 shows that cleavage with furin during expression or with Prescission after expression significantly improves the c-Met dependent accumulation on A549 cells compared to restricted dsFv modules. Furthermore, for the cMet module functionality regarding interference with signaling pathways could be demonstrated for the unleashed dsFv module that recognizes cMet: Unrestricted cMet dsFv (via Furin cleavage or Prescission cleavage) interfered with HGF-mediated ACT signaling as efficiently as the monovalent Fab derived from the parent antibody (FIG. 8). In contrast, restricted dsFv modules had dramatically reduced activity which correlated with their reduced affinity.

Example 3

Figure 10:
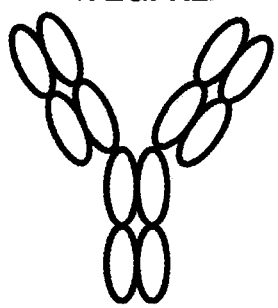
FIG. 10: Schematic representation of additional mono- and bispecific antibodies. The lower panel shows a bispecific antibodies according to the invention which bind different target antigens before processing by Furin (left) and after in-process processing by furin (right).
Figure 10:
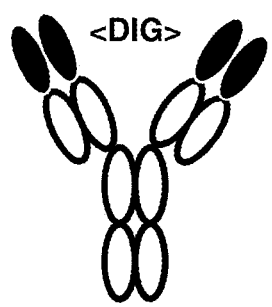
Figure 10:
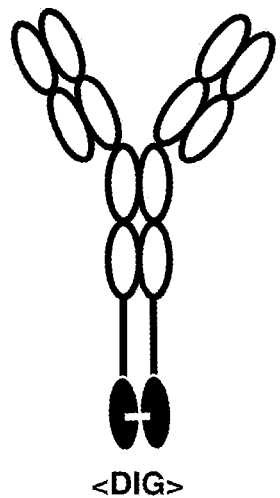
Figure 10:
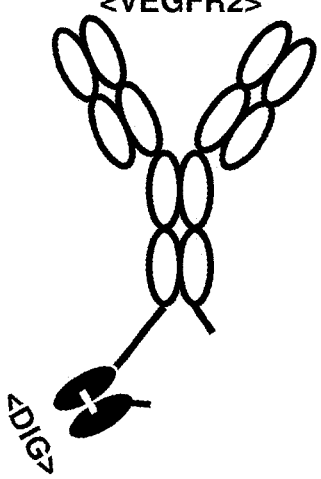

Generation and Biochemical Characterization of Additional Bispecific Antibodies that are Processed During Expression To demonstrate that the design and process of production of bispecific antibodies according to the invention is generalizable, we designed, produced and characterized various additional bispecific antibodies. All of these were generated as precursor molecules containing disulfide-stabilized Fv entities (as described above) connected via one furin cleavable and one noncleavable peptide sequence to IgG derivatives. These bispecific antibody derivatives were composed of binding modules that address cell surface antigens on tumors (as target 1) as well as anti-digoxigenin binding entities (as target 2). The cell surface targeting specificities addressed either the cancer associated LeY carbohydrate antigen (LeY), CD22, CD33, Her2 or IGF1R antigens which are also expressed on cancer cells, or the VEGFR2 which is expressed in many tumors. The sequences of antibodies with these binding specificities, as well as the corresponding Dig.-binding antibody derivative have been previously described (see WO 2011/003557), and can be derived therefrom. The composition of the combined molecules with dual functionalities according to our invention is exemplarily shown in FIG. 10.

Figure 11A:
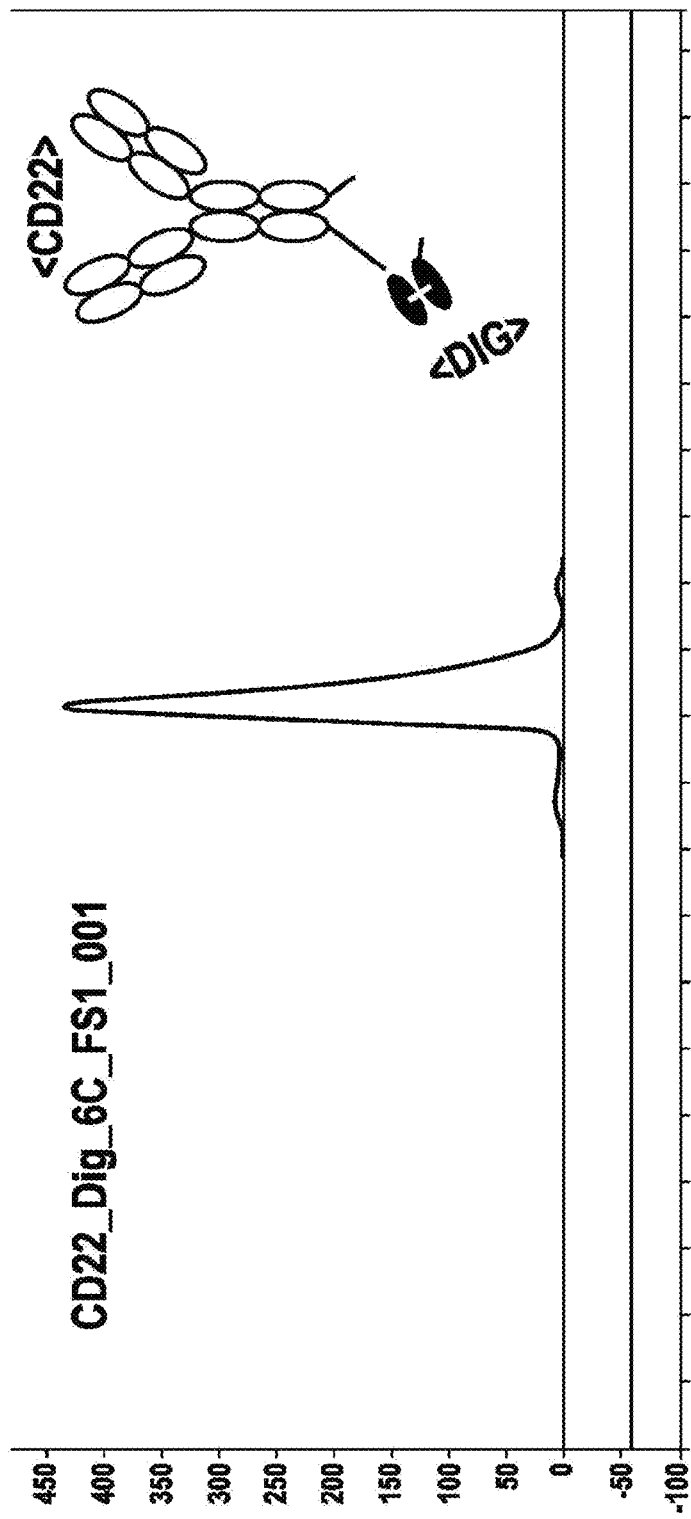
FIG. 11A-B: Expression and purification of bispecific furin-processed dsFv-containing antibody derivatives VEGFR_Dig_6C_FS1 (FIG. 11B) and CD22_Dig_6C_FS1 (FIG. 11A). Shown are size exclusion profiles which demonstrate homogeneity and almost complete absence of aggregates in purified protein preparations.
Figure 11B:
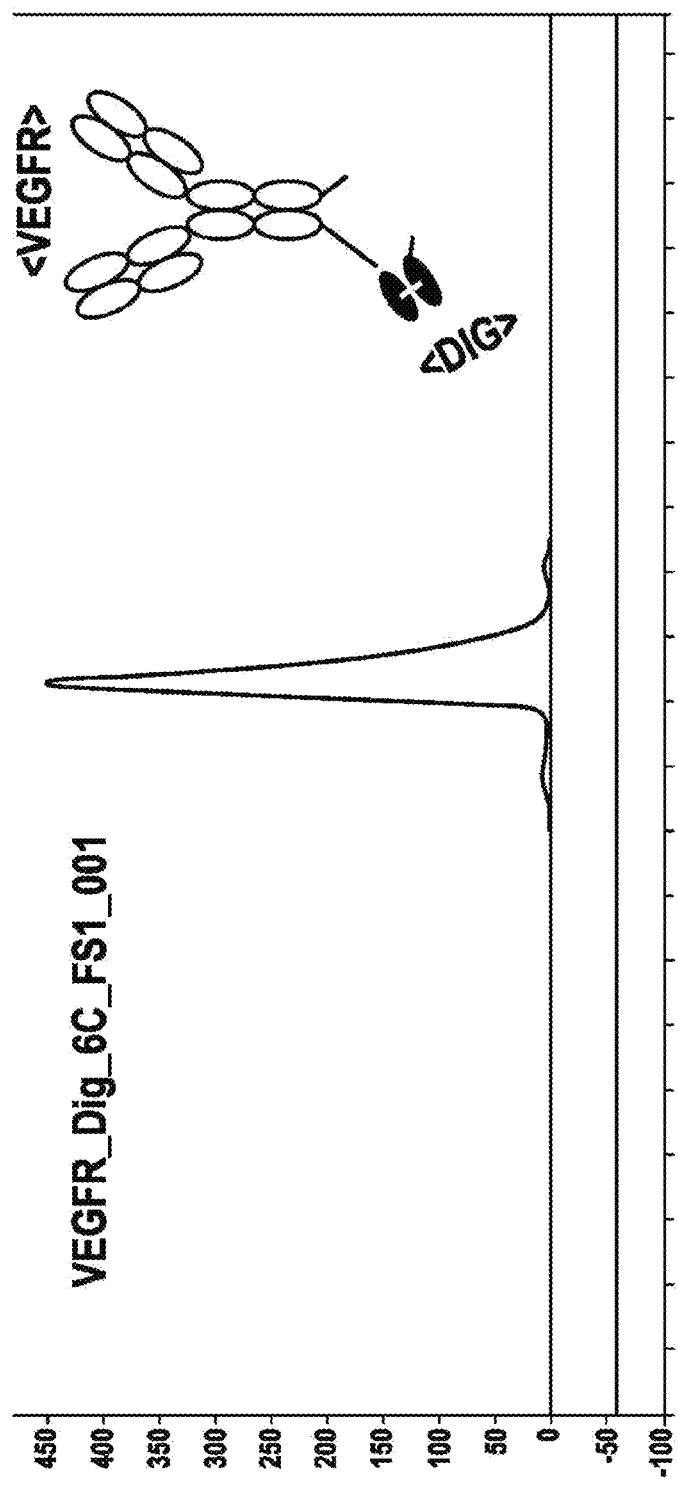

Expression and purification of these furin-processed bispecific antibody derivatives was performed as described in Example 2. Expression yield per liter cell culture supernatant were in the same range (7-40 mg/L) as those observed for many unmodified antibodies. All bispecific antibody derivatives could be purified to homogeneity and all protein preparations contained no or only minute amounts of aggregates. In many preparations no aggregates were detectable at all, as shown by SEC analyses of these preparations in FIG. 11. The expression yields of purified homogenous antibody per liter culture supernatant were 15 mg/L for LeY-Dig, 19.5 mg/L for CD22-Dig, 40 mg/L for CD33-Dig, 40.2 mg/L for VEGFR2-Dig, 25 mg/L for Her2-Dig and 7 mg/L for IGF1R-Dig.

Figure 12:
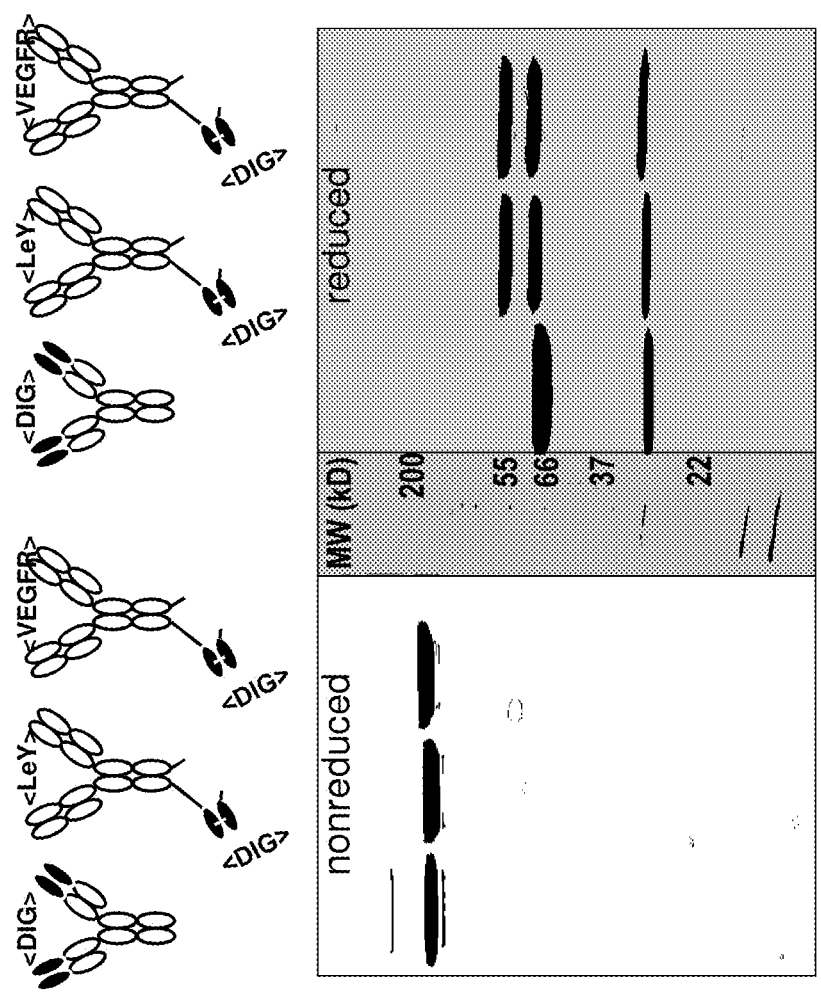
FIG. 12: Nonreducing and reducing SDS Page of protein preparations after Protein-A and SEC purification demonstrate homogeneity and correct composition after processing of the purified bispecific antibody derivatives.

The presence of the furin recognition site in one of the peptide connectors that fuses dsFv to the IgG backbone leads as desired to complete proteolytic processing during the expression process. This was demonstrated by reducing and non-reducing SDS-PAGE analyses: disulfide-bonded bispecific antibodies of large size are seen under nonreducing conditions, which separate into separate chains of expected molecular weight upon reduction (FIG. 12). Furin cleavage converts only one of the extended H chain (63 kD) to a H-chain of normal size (50 kD) and releases a protein fragment of 12 kD. Both products of this processing process are clearly detectable in the reducing gel.

Figure 13A:
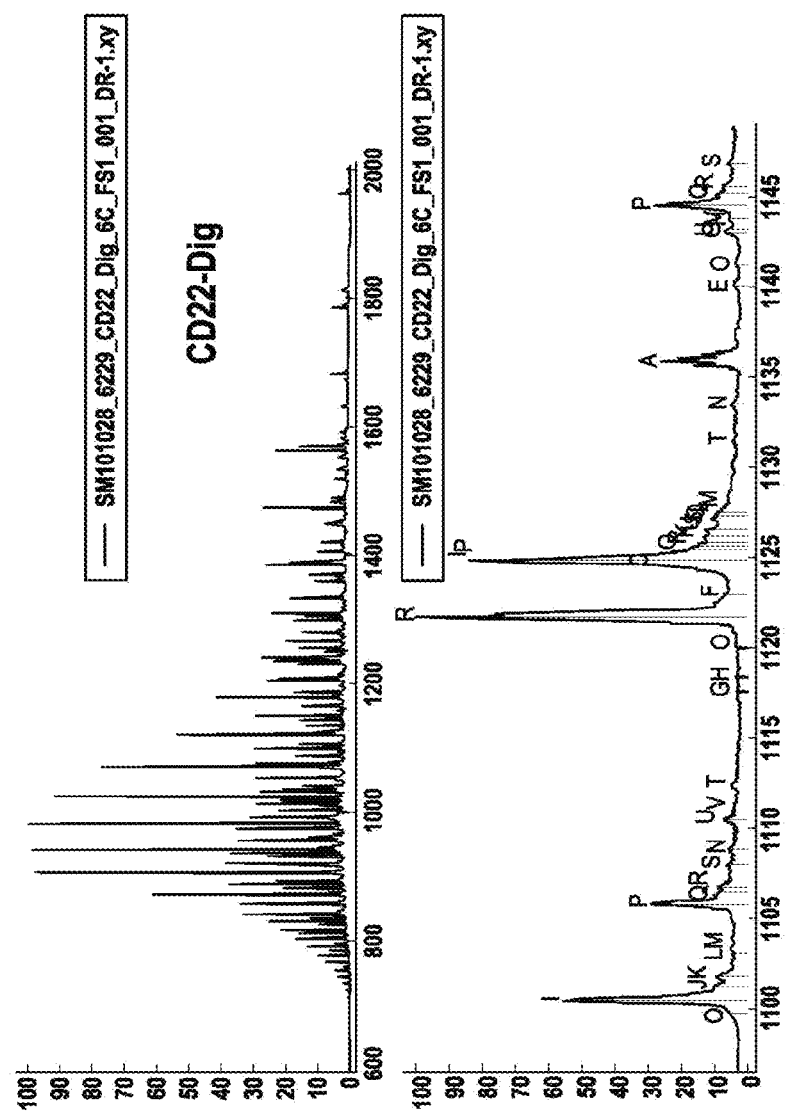
FIG. 13A-B: Mass spectrometric analyses of protein preparations after Protein-A and SEC purification demonstrate homogeneity and correct composition (complete in-process furin processing) after processing of the purified bispecific antibody derivatives CD22-Dig (FIG. 13A) and VEGFR-Dig (FIG. 13B).
Figure 13B:
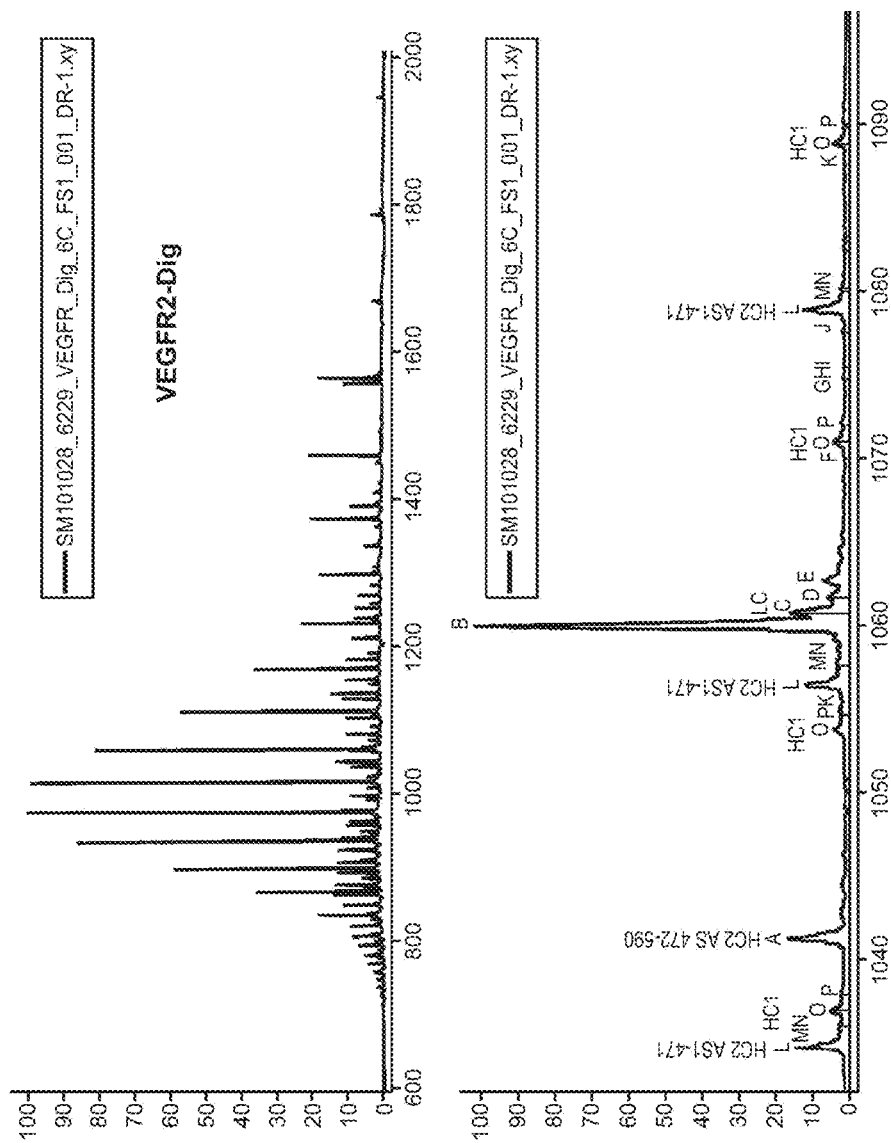

The defined composition and homogeneity of protein products was further confirmed by mass spectrometry (FIG. 13) to determine the exact molecular mass of proteins and protein fragments. Prior to the mass spectrometric analysis, the antibodies were deglycosylated applying standard protocols using N-Glycosidase F in order to decrease spectral complexity and facilitate data interpretation. As a further measure to facilitate data interpretation, molecules to be analyzed were cleaved by IdeS protease into disulfide-bridged Fc and F(ab)$_2$ fragments. The fragments were subsequently reduced with TCEP to separate their different components to facilitate identification and characterization as described above, thereafter desalted and subsequently subjected to electrospray ionization (ESI) mass spectrometry. The results of these analyses indicate that all analyzed bispecific antibody derivatives that are translated as precursor forms are thereafter processed by furine within the secretory pathway of producer cells. The protein preparations showed complete processing by furin (within detection limits) and unprocessed precursor fragments (extended IdeS-Fc fragments) were not detectable. In addition, our mass analyses indicated further carboxyterminal processing of the furin-cleaved protein modules. The arginine and/or lysine residues that preceded the cleavage site and formed part of the furine recognition sequence were quantitatively removed from the furin-processed products.

These results prove that our design and process of production of bispecific antibodies according to the invention is generalizable: various bispecific antibodies that contain furin recognition sites within connector peptides can be generated, produced and purified to homogeneity.

Example 4

Figure 14A:
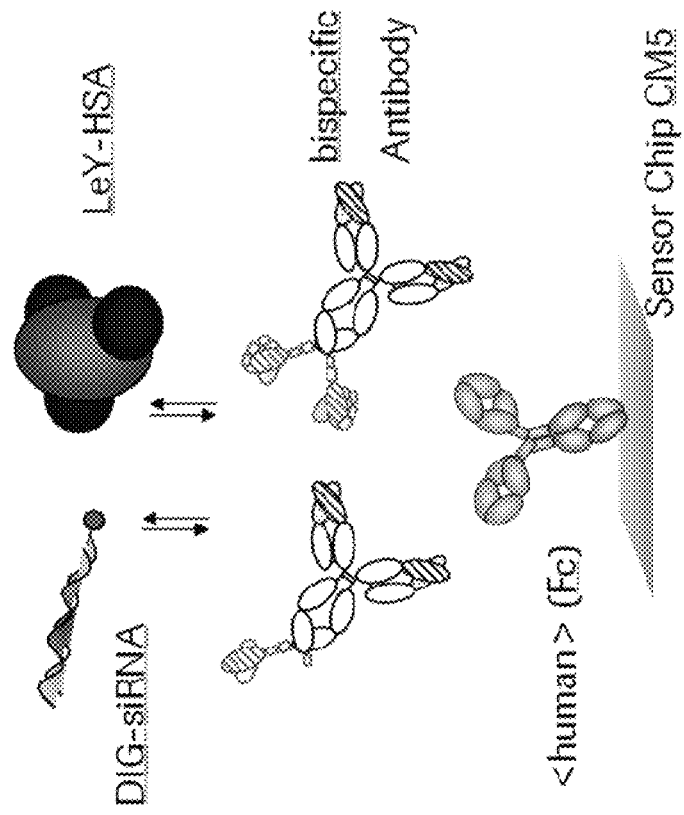
FIG. 14A-C: Binding analyses by Surface Plasmon Resonance of additional bispecific antibodies according to the invention.
Figure 14B:
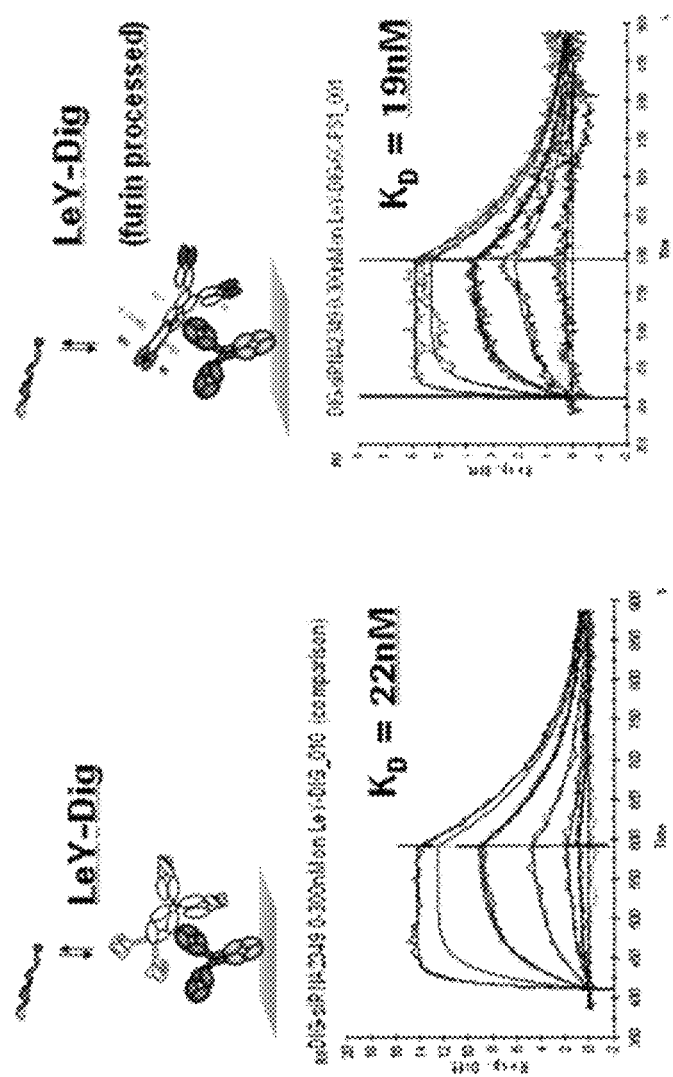
Figure 14C:
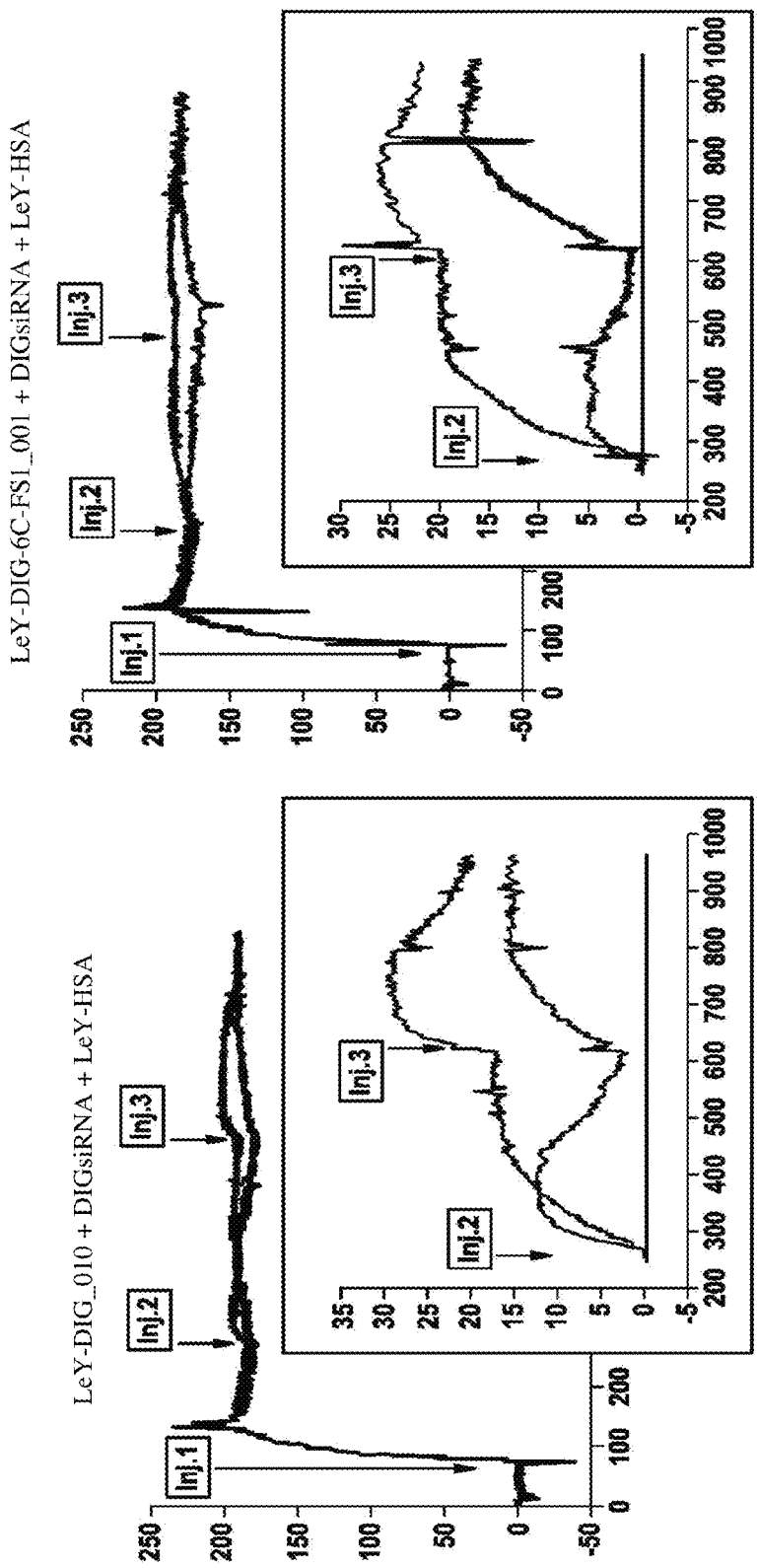
Figure 15A:
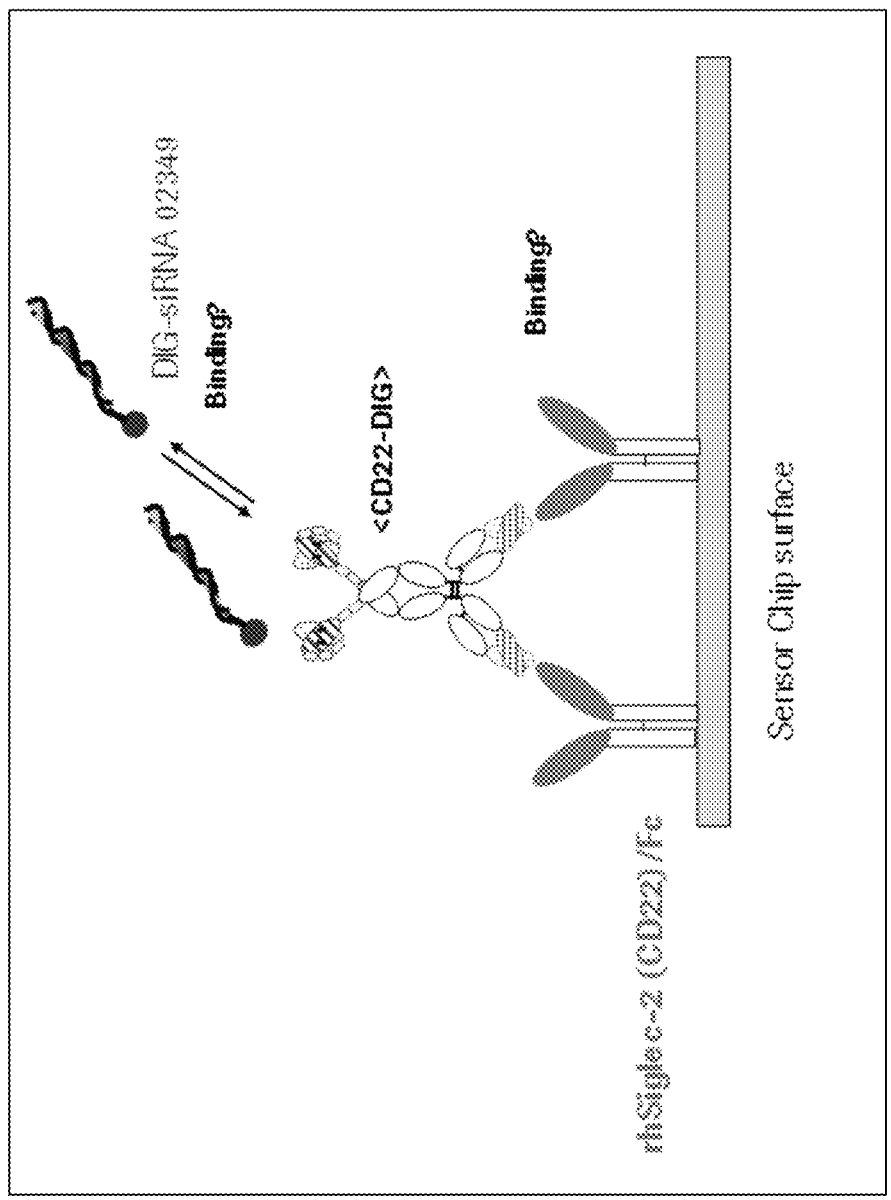
FIG. 15A-B: Binding analyses by Surface Plasmon Resonance of the additional furin-processed bispecific antibody CD22-Dig according to the invention.
Figure 15B:
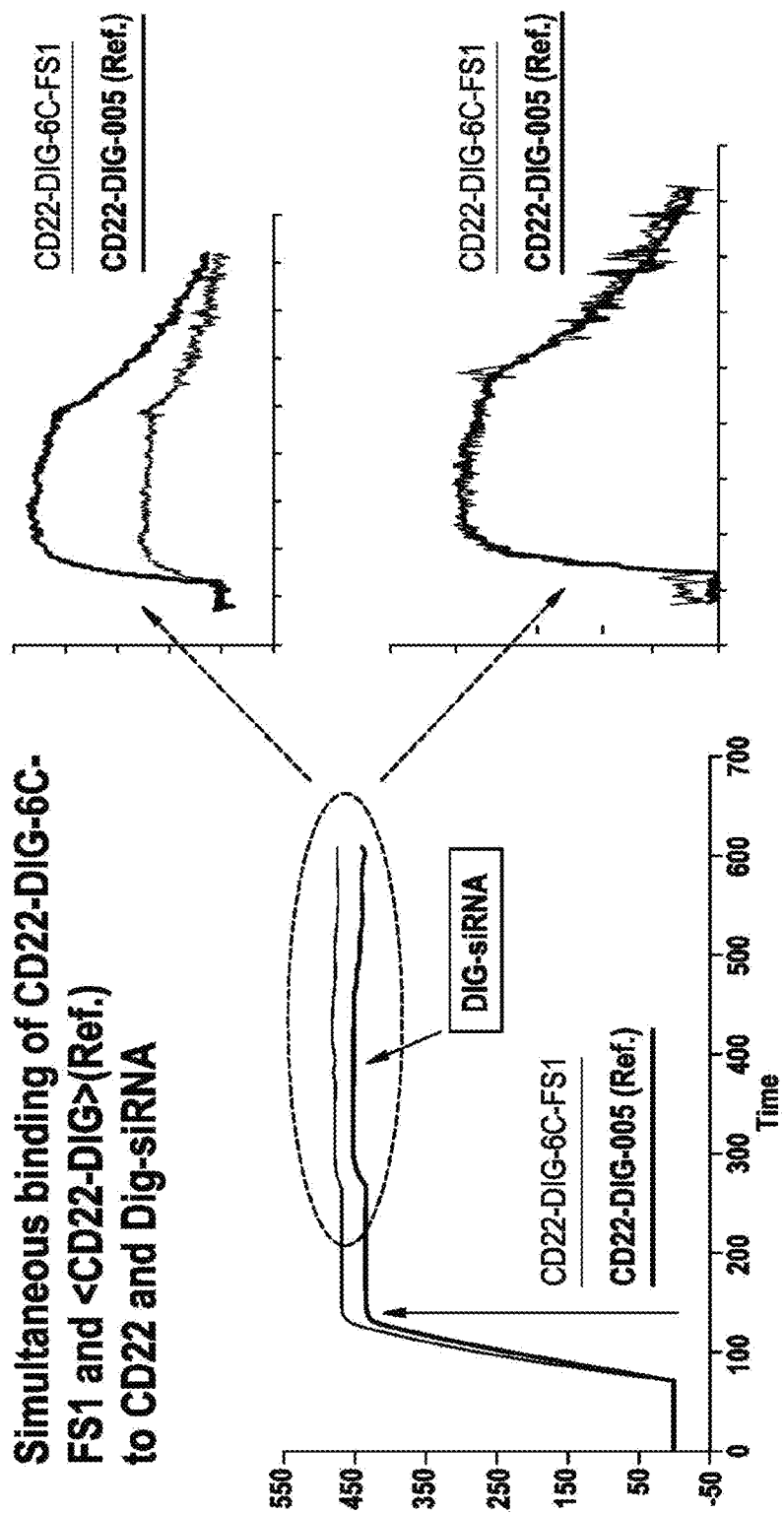

Functional Characterization of Additional Bispecific Antibodies that are Processed During Expression The functionality of additional bispecific antibodies (which are connected only via one domain of the disulfide-stabilized Fv fragment to the full length antibody) was investigated in binding assays via surface Plasmon resonance. Because the processing via Furin occurs during the expression process, the preparations obtained after purification should be composed of bispecific entities with fully active linkerless dsFvs. Full binding competency was confirmed by SPR analyses which showed that all binding entities of the bispecific antibody as well as the dsFv that binds Digoxigenin, have unrestricted binding capability. Their affinity to target antigen 1 and to the target antigen 2 Digoxigenin is comparable to that of unmodified antibodies or Fab. For example, the individual binding affinity for Digoxigeninylated payload of bispecific antibody derivatives according to the invention in comparison with parent antibodies were Kd 22 nM for the control molecule and 19 nM for the furin-processed molecule (FIG. 14). Furthermore, these SPR experiments in FIG. 14b and in FIG. 15b clearly demonstrated that the bispecific antibody derivatives simultaneously bind two different antigens. This was shown for target 1 antigen LeY as well as CD22 (FIG. 14 and in FIG. 15).

Figure 16A:
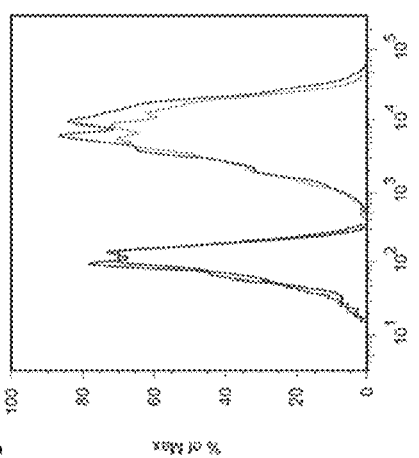
FIG. 16A-B: Binding of additional bispecific antibodies according to the invention to live cells. For FACS analyses, bispecific antibodies according to the invention were first incubated with target cells and subsequently incubated with either anti-huCkappa (to detect the bispecific antibody) (FIG. 16A) or to digoxigenated fluorophore (to detect the functionality of the $2^{nd}$ binding entity) (FIG. 16B). Thereby, binding functionality of both specificities can simultaneously be assessed. Cell associated signals are only detected when bispecifics bind to the cells (functionality towards target 1) and thereafter capture Dig-payload (functionality towards target 2). Bispecifics that do not recognize cell surface targets do not (as expected) generate significant cell associate signals in the same experimental setting.
Figure 16A:
Figure 16A:
Figure 16A:
Figure 16A:
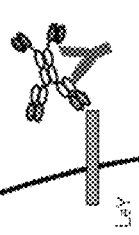
Figure 16A:
Figure 16A:
Figure 16A:
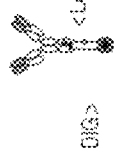
Figure 16B:
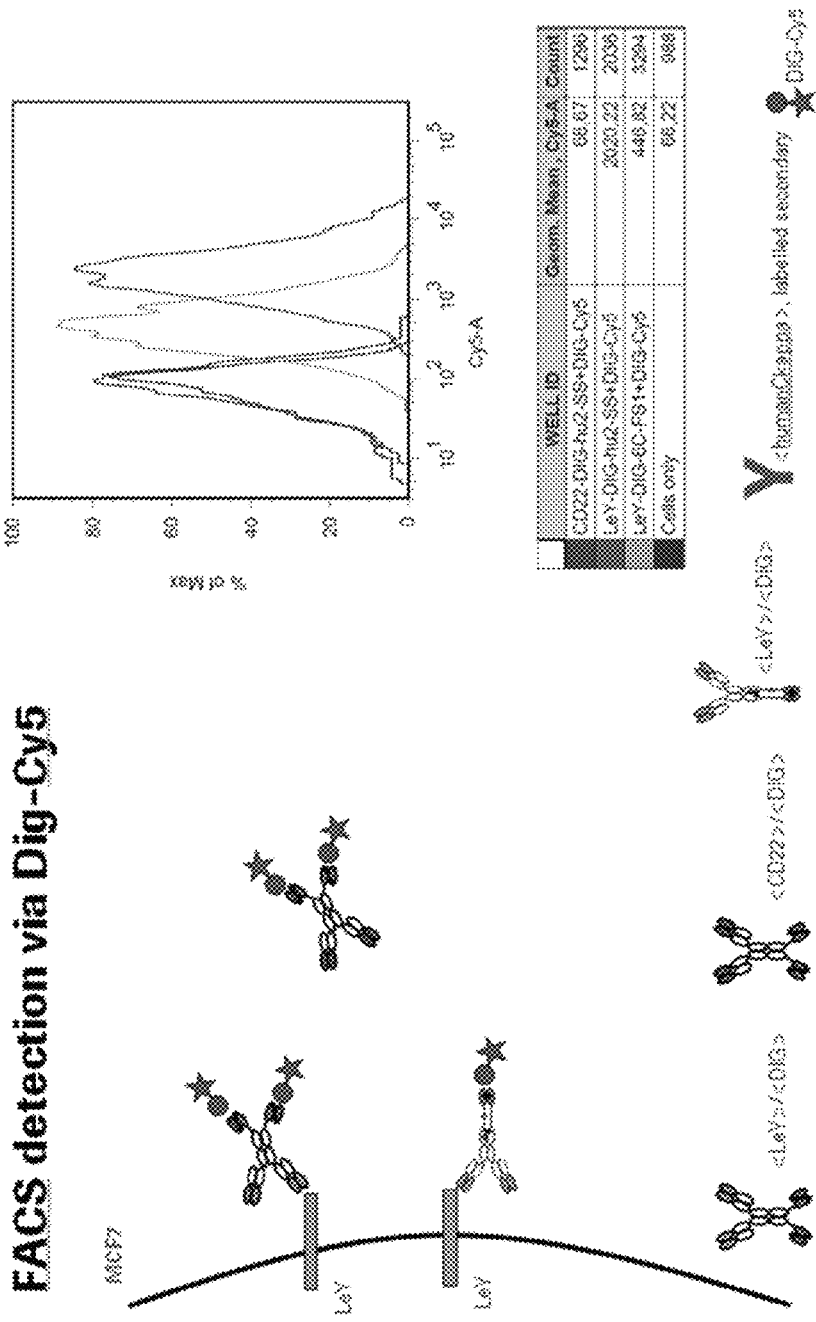

The functionality of the bispecific antibody that binds LeY as well as Dig (which are connected only via one domain of the disulfide-stabilized Fv fragment to the full length antibody) was further investigated in cellular assays: FACS experiments (FIG. 16) showed that the bispecific antibody that were designed and generated according to the invention bind specifically to LeY antigen expressing MCF7 target cells. This is shown via secondary antibodies (FIG. 16a), which demonstrate that the LeY-binding capability of the furin-processed bispecific antibodies is indistinguishable from the original LeY-binding antibody. Furthermore, these bispecific antibodies are able to direct fluorescent payloads that are bound by the 2nd specificity (Dig-Cy5) to these target cells, which is shown in FIG. 16b. Thereby, Dig-conjugated payloads are enriched on target cells but not on cells that do not express target antigen. Quantitative binding and cellular accumulation of Dig-Payload is further demonstrated by the fact that the targeted fluorescence on cells is twice as high for modules with two Dig-binding entities compared to bispecifics that possess only one Dig-binding entity.

These results prove that our design and process of production of bispecific antibodies according to the invention is generalizable: various bispecific antibodies that contain furin recognition sites within connector peptides can be generated, which retain full binding activity towards target 1 as well as towards target 2.

What is claimed is:

1. A bispecific antibody comprising
   a) a full length antibody specifically binding to a first antigen and consisting of two antibody heavy chains and two antibody light chains;
   b) a Fv fragment specifically binding to a second antigen comprising a $VH^2$ domain and a $VL^2$ domain, wherein the $VH^2$ and $VL^2$ domains are connected via a disulfide bridge,
   wherein only either the $VH^2$ domain or the $VL^2$ domain of the Fv fragment is fused via a peptide linker to the heavy or light chain of the full length antibody, and
   wherein the Fv fragment is fused to the full length antibody via a single peptide linker.

2. The bispecific antibody according to claim 1, wherein the bispecific antibody is trivalent and
   either the $VH^2$ domain or the $VL^2$ domain of the Fv fragment is fused via a peptide linker to the heavy chain of the full length antibody.

3. The bispecific antibody according to claim 2, wherein the $VH^2$ domain or the $VL^2$ domain of the Fv fragment is N-terminally fused via a peptide linker to the C-terminus of the full length antibody.

4. The bispecific antibody according to claim 2, wherein the $VH^2$ domain or $VL^2$ domain of the Fv fragment is C-terminally fused via a peptide linker to the N-terminus of the full length antibody.

5. The bispecific antibody according to claim 1, wherein the $VH^2$ domain or $VL^2$ domain of the Fv fragment is N-terminally fused via a peptide linker to the C-terminus of the heavy or light chain of the full length antibody.

6. The bispecific antibody according to claim 1, wherein the $VH^2$ domain or $VL^2$ domain of the Fv fragment is C-terminally fused via a peptide linker to the N-terminus of the heavy or light chain of the full length antibody.

7. The bispecific antibody according to claim 1, wherein the $VH^2$ domain and the $VL^2$ domain of the Fv fragment are connected via a disulfide bridge which is introduced between the following positions:
   i) $VH^2$ domain position 44 and $VL^2$ domain position 100,
   ii) $VH^2$ domain position 105 and $VL^2$ domain position 43, or
   iii) $VH^2$ domain position 101 and $VL^2$ domain position 100,
   wherein the numbering is according to Kabat.

8. The bispecific antibody according to claim 1, wherein the $VH^2$ domain and the $VL^2$ domain of the Fv fragment are connected via a disulfide bridge which is introduced between the
   $VH^2$ domain position 44 and $VL^2$ domain position 100,
   wherein the numbering is according to Kabat.

9. The bispecific antibody according to claim 1, wherein the full length antibody comprises a first CH3 domain and a second CH3 domain, and the first CH3 domain of the full length antibody and the second CH3 domain of the full length antibody each meet at an interface which comprises an alteration in the original interface between the first and second CH3 domains;
   wherein i) in the first CH3 domain,
      an amino acid residue is replaced with an amino acid residue having a larger side chain volume, thereby generating a protuberance within the interface of the first CH3 domain which is positionable in a cavity within the interface of the second CH3 and ii) in the second CH3 domain, an amino acid residue is replaced with an amino acid residue having a smaller side chain volume, thereby generating a cavity within the interface of the second CH3 domain within which a protuberance within the interface of the first CH3 domain is positionable.

10. The bispecific antibody according to claim 9, wherein said amino acid residue having a larger side chain volume is selected from the group consisting of arginine (R), phenylalanine (F), tyrosine (Y), and tryptophan (W) and said amino acid residue having a smaller side chain volume is selected from the group consisting of alanine (A), serine (S), threonine (T), and valine (V).

11. The bispecific antibody according to claim 9, wherein both the first and second CH3 domains are further altered by the introduction of a cysteine (C) residue in positions of the first and second CH3 domains such that a disulfide bridge between the CH3 domains can be formed.

12. A method for the preparation of the bispecific antibody according to claim 1 comprising the steps of
    A) expressing in a mammalian cell nucleic acids encoding a bispecific antibody comprising
        a) a full length antibody specifically binding to a first antigen and consisting of two antibody heavy chains and two antibody light chains;
        b) a Fv fragment specifically binding to a second antigen comprising a $VH^2$ domain and a $VL^2$ domain, wherein the $VH^2$ domain and a $VL^2$ domains are connected via a disulfide bridge,
    wherein the Fv fragment is fused
        via the N-termini of the $VH^2$ domain and the $VL^2$ domain to the both C-termini of the heavy chains of the full length antibody via a first and second peptide linker, or
        via the C-termini of the $VH^2$ domain and the $VL^2$ domain to the both N-termini of one heavy and one light chain of the full length antibody via a first and second peptide linker,
    and wherein
    one of the linkers comprises a protease cleavage site cleavable by furin, and the other linker does not comprise a protease cleavage site;
    B) cleaving the linker comprising the protease cleavage site; and
    C) recovering said antibody from said cell or a cell culture supernatant.

13. A method for the preparation of the trivalent, bispecific antibody according to claim 2 comprising the steps of
    A) expressing in a mammalian cell nucleic acids encoding a bispecific antibody comprising
        a) a full length antibody specifically binding to a first antigen and consisting of two antibody heavy chains and two antibody light chains;
        b) a Fv fragment specifically binding to a second antigen comprising a $VH^2$ domain and a $VL^2$ domain, wherein the $VH^2$ and $VL^2$ domains are connected via a disulfide bridge,
    wherein the Fv fragment is fused
        via the N-termini of the $VH^2$ domain and the $VL^2$ domain to the both C-termini of the heavy chains of the full length antibody via a first and second peptide linker, or
        via the C-termini of the $VH^2$ domain and the $VL^2$ domain to the both N-termini of the heavy chains of the full length antibody via a first and second peptide linker, and wherein
        one of the linkers comprises a protease cleavage site cleavable by Prescission protease, and the other linker does not comprise a protease cleavage site;
    B) cleaving the linker comprising the protease cleave site; and
    C) recovering said antibody from said cell or a cell culture supernatant.

14. The method according to claim 12, wherein the protease cleavage site cleavable by furin is SEQ ID NO:13 or SEQ ID NO:14.

15. The method according to claim 13, wherein the protease cleavage site cleavable by Prescission protease is SEQ ID NO:15.

16. The method according to claim 12, wherein the mammalian cell is a CHO cell, NS0 cell, SP2/0 cell, HEK293 cell, COS cell or PER.C6 cell.

17. A pharmaceutical composition comprising the bispecific antibody according to claim 1.

18. The method according to claim 12, wherein the $VH^2$ domain and the $VL^2$ domain of the Fv fragment are connected via a disulfide bridge which is introduced between the following positions:
    i) $VH^2$ domain position 44 and $VL^2$ domain position 100,
    ii) $VH^2$ domain position 105 and $VL^2$ domain position 43, or
    iii) $VH^2$ domain position 101 and $VL^2$ domain position 100,
    wherein the numbering is according to Kabat.

19. The method according to claim 13, wherein the $VH^2$ domain and the $VL^2$ domain of the Fv fragment are connected via a disulfide bridge which is introduced between the following positions:
    i) $VH^2$ domain position 44 and $VL^2$ domain position 100,
    ii) $VH^2$ domain position 105 and $VL^2$ domain position 43, or
    iii) $VH^2$ domain position 101 and $VL^2$ domain position 100,
    wherein the numbering is according to Kabat.

* * * * *